US006972298B2

(12) United States Patent
Baragi et al.

(10) Patent No.: US 6,972,298 B2
(45) Date of Patent: Dec. 6, 2005

(54) METHOD OF TREATING OR INHIBITING NEUTROPHIL CHEMOTAXIS BY ADMINISTERING A MEK INHIBITOR

(75) Inventors: Vijaykumar M. Baragi, Ann Arbor, MI (US); Madhav Narasimha Devalaraja, Ann Arbor, MI (US); Joseph Edwin Low, Brighton, MI (US); Vaishalee A. Padgaonkar, Livonia, MI (US)

(73) Assignee: Warner-Lambert Company, Ann Arbor, MI (US)

( * ) Notice: Subject to any disclaimer, the term of this patent is extended or adjusted under 35 U.S.C. 154(b) by 229 days.

(21) Appl. No.: 10/144,315

(22) Filed: May 9, 2002

(65) Prior Publication Data

US 2003/0055095 A1 Mar. 20, 2003

Related U.S. Application Data

(60) Provisional application No. 60/289,881, filed on May 9, 2001.

(51) Int. Cl.⁷ .................. A61K 31/41; A61K 31/35; A61K 31/165

(52) U.S. Cl. .................. 514/382; 514/453; 514/619

(58) Field of Search ................ 514/382, 453, 514/619

(56) References Cited

U.S. PATENT DOCUMENTS

| | | | | |
|---|---|---|---|---|
| 5,525,625 A | * | 6/1996 | Bridges et al. | ............ 514/456 |
| 5,962,265 A | | 10/1999 | Norris et al. | |
| 6,251,943 B1 | * | 6/2001 | Barrett et al. | ............... 514/564 |
| 6,440,966 B1 | * | 8/2002 | Barrett et al. | ........... 514/237.8 |
| 2003/0060469 A1 | | 3/2003 | Ludwig et al. | |

FOREIGN PATENT DOCUMENTS

| | | |
|---|---|---|
| WO | WO 98/37881 A1 | 9/1998 |
| WO | WO 99/01421 A1 | 1/1999 |
| WO | WO 99/01426 A1 | 1/1999 |
| WO | WO 99/34792 A1 | 7/1999 |
| WO | WO 00/35435 A1 | 6/2000 |
| WO | WO 00/35436 A2 | 6/2000 |
| WO | WO 00/37141 A1 | 6/2000 |
| WO | WO 00/40235 A2 | 7/2000 |
| WO | WO 00/40237 A1 | 7/2000 |
| WO | WO 01/05392 A2 | 1/2001 |
| WO | WO 02/06213 A2 | 1/2002 |
| WO | WO 02/069960 A2 | 9/2002 |
| WO | WO 02/076496 A1 | 10/2002 |

OTHER PUBLICATIONS

P. J. Barnes, "Future Advances in COPD Therapy", Respiration, vol. 68, pp 441–448 (2001).
Database WPI, Section Ch, Week 200213, Derwent Publications, Ltd., London, GB, An (2002)097426 Abstract Only.
T. Sasaki, et al., "Function of P13kGamma in Thymocyte Development, T Cell Activation, and Neutrophil Migration", Science, vol. 287, P. 1040–1046 (2000).
J. C. Lee, et al., "Inhibition of p38 MAP Kinase as a Therapeutic Strategy", Immunopharmacology, vol. 47, p. 185–201 (2000).
P. Scapini, et al., "The neutrophil as a cellular source of chemokines", Immunol. Rev., vol. 177, p. 195–203 (2000).
C. R. Mackay, "Chemokines: Immunology's high impact factors", Nat. Immunol. vol. 2(2), p. 95–101 (2001).
D. Rossi, et al., "The biology of chemokines and their receptors", Ann. Rev. Immunol., vol. 18, p. 217–242 (2000).
N.T. Luu, et al., "Differential ability of exogenous chemotactic agents to disrupt transendothelial migration of flowing neutrophils", J. Immunol. vol. 164, p. 5961–5969 (2000).
E. Sato, et al., "Reactive nitrogen and oxygen species attenuate interleukin–8–induced neutrophil chemotactic activity, in vitro", J. Biol. Chem., vol. 275, p. 10826–10830 (2000).
M.D. Becker, et al., "Reduced leukocyte migration, but normal rolling and arrest, in interleukin–8–receptor homologue knockout mice", Invest. Opthalmol. Vis. Sci., vol. 41, p. 1812–1817 (2000).
O. Tabary, et al., "High susceptibility for cystic fibrosis human airway gland cells to produce IL–8 through the I kappa B kinase alpha pathway in response to extracellular NaCl content", J. Immunol., vol. 164, p. 3377–3384 (2000).
R.A. Dumont, et al. "Systemic neutralization of interleukin–8 markedly reduces neutrophilic pleocytosis during experimental lipopolysaccharide–induced meningitis in rabbits", Infect. Immun., vol. 68, p. 5756–5763 (2000).
A. Ben–Baruch, et al., "Interleukin–8 receptor beta: The role of the carboxy terminus in signal transduction", J. Biol. Chem., vol. 270, p. 9121–9128 (1995).
V. Shyamala, et al., "Interleukin–8 Receptors R1 and R2 Activate Mitogen–Activated Protein Kinases and Induce c–fos, Independent of Ras and Raf–1 in Chinese Hamster Ovary Cells", Biochemistry, vol. 37, p. 15918–15924 (1998).
R.M. Richardson, et al., "Multiple signaling pathways of human interleukin–8 receptor A. Independent regulation by phosphorylation", J. Biol. Chem., vol. 273, p. 10690–10695 (1998).
C, Knall, et al., "Interleukin 8–stimulated phosphatidylinositol–3–kinase activity regulates the migration of human neutrophils independent of extracllular signal–regulated kinase and p38 mitogen–activated protein kinases", Proc. Natl. Acad. Sci., vol. 94, p. 3052–3057 (1997).
J.S. Sebolt–Leopold, et al., "Blockade of the Map kinase pathway suppresses growth of colon tumors in vivo", Nat. Med., vol. 5, p. 810–816 (1999).
C. Knall, et al., Interleukin–8 regulation of the Ras/Raf/mitogen–activated protein kinase pathway in human neutrophils, J. Biol. Chem., vol. 271, p. 2832–2838 (1996).

* cited by examiner

Primary Examiner—Raymond J. Henley, III
(74) Attorney, Agent, or Firm—Peter C. Richardson; Garth Butterfield

(57) ABSTRACT

The present invention provides a method of treating or preventing neutrophil chemotaxis. Specifically, the present invention provides a method of treating or preventing neutrophil migration by administering to a patient a MEK inhibitor.

17 Claims, 7 Drawing Sheets

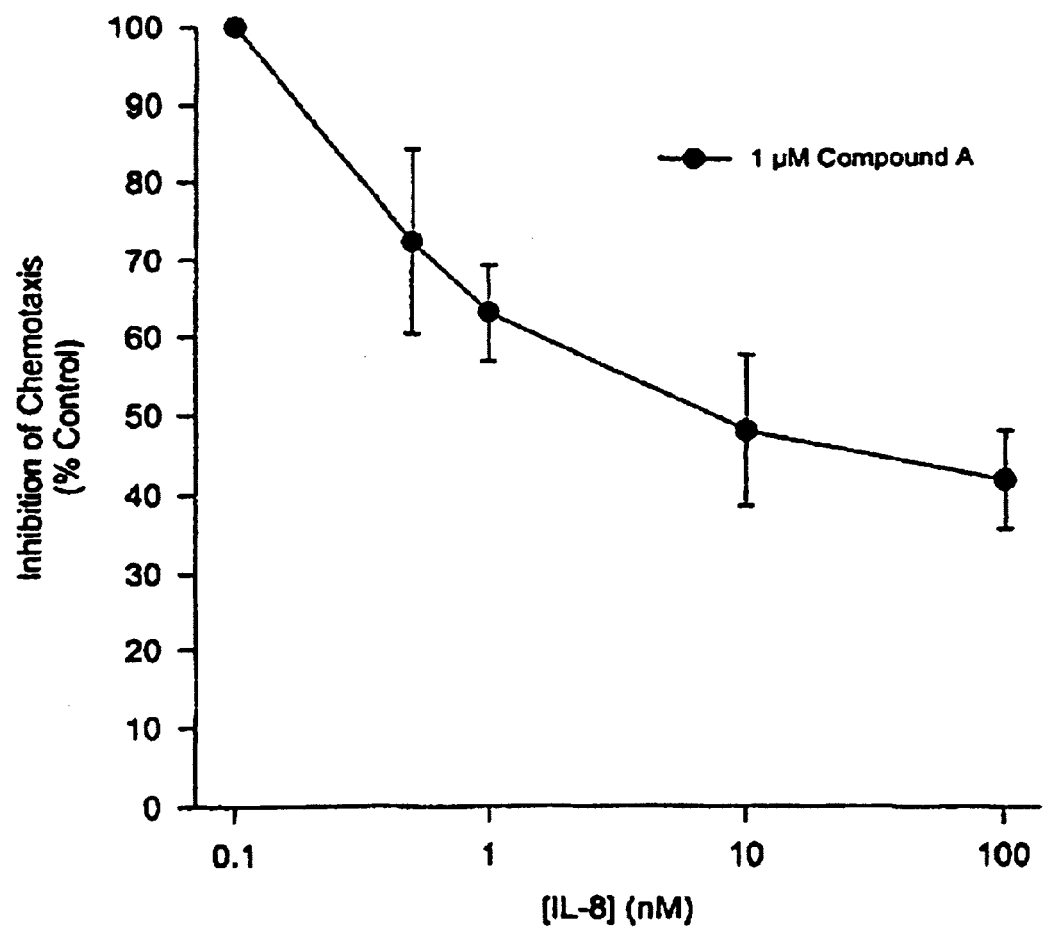

METHOD OF TREATING OR INHIBITING NEUTROPHIL CHEMOTAXIS BY ADMINISTERING A MEK INHIBITOR

This application claims the benefit of priority to U.S. provisional application Serial No. 60/289,881 filed May 9, 2001.

FIELD OF THE INVENTION

The present invention relates to a method of treating or inhibiting neutrophil migration or chemotaxis in a patient by administering to the patient a compound that is an MEK inhibitor alone or in combination with PI3K inhibitors.

BACKGROUND OF THE INVENTION

Neutrophils play a critical role in an inflammatory response and constitute the initial host defense strategy (Scapini P., Lapinet Vera J. A., Gasperini S., Calzetti F., Bazzoni F., Cassatella M. A. The neutrophil as a cellular source of chemokines. *Immunol. Rev.* 2000; 177:195–203). In response to an inflammatory C stimulus, neutrophils are sequestered in the microvasculature, traverse the vascular barriers, and finally converge to the site of inflammation. While chronic diseases are generally characterized by excessive monocyte/macrophage or lymphocyte infiltration, acute conditions are characterized by massive neutrophil influx. Neutrophils are key immune effector cells in a number of diseases including ischemia-reperfusion injury, chronic obstructive pulmonary disease, acute respiratory disease syndrome, cystic fibrosis, idiopathic pulmonary fibrosis, sepsis, endotoxemia, emphysema, or asbestosis (Mackay R. Chemokines: Immunology's high impact factors. *Nat. Immunol.* 2001;2(2):95–101). Various studies clearly demonstrate that chemoattractants, such as IL-8, f-MLP, and C5a activate neutrophils and induce various functional responses such as chemotaxis, respiratory burst, and phagocytosis.

Chemotactic cytokines are small, inducible, secreted, pro-inflammatory cytokines that primarily aid in recruitment of leukocytes to the site of inflammation. The members of the chemokine superfamily are divided into four subgroups based on arrangement of the first two of the conserved four cysteine residues (Rossi D., Zlotnik A. The biology of chemokines and their receptors. *Ann. Rev. Immunol.* 2000;18:217–242). IL-8 is the predominant member of the CXC class of chemokines that primarily aid in recruitment of neutrophils. Chemokines mediate their biological responses by binding to target cell-surface chemokine receptors that belong to the family of G-protein coupled, seven transmembrane-domain receptors. The receptors that bind the CXC chemokines are designated as CXCRs. IL-8 binds with similar affinities to both CXCR1 and CXCR2. Several studies demonstrate the IL-8-specific neutrophil migration/ chemotaxis both in vitro and in vivo (Luu N. T., Rainger G. E., Nash G. B. Differential ability of exogenous chemotactic agents to disrupt transendothelial migration of flowing neutrophils. *J. Immunol.* 2000;164:5961–5969; Sato E., Simpson K. L., Grisham M. B., Koyoma S., Robbins R. A. Reactive oxygen and nitrogen species attenuate interleukin-8-induced neutrophil chemotactic activity, in vitro. *J. Biol. Chem.* 2000;275:10826–10830; and Rennekampff H. O., Hansbrough J. F., Kiessig V., Dore C., Sticherling M., Schroder J. M. Bioactive interleukin-8 is expressed in wounds and enhances wound healing. *J. Surg. Res.* 2000;93:41–54). In addition, neutrophils from IL-8 receptor homologue –/– mouse exhibit normal degranulation but lack the ability to migrate to the site of injury (Becker M. D., O'Rourke L. M., Blackman W. S., Planck S. R., Rosenbaum J. T. Reduced leukocyte migration, but normal rolling and arrest, in interleukin-8 receptor homologue knockout mice. *Invest. Opthalmol. Vis. Sci.* 2000;41:1812–1817). Apparently this process cannot be substituted by other chemoattractants such as f-MLP or C5a. In various diseases, increased neutrophil infiltration correlates well with increased local IL-8 levels (Aggarwal A., Baker C. S., Evans T. W., Haslam P. L. G-CSF and IL-8 but not GM-CSF correlate with severity of pulmonary neutrophilia in acute respiratory distress syndrome. *Eur Resp. J.* 2000;15:895–901; Lin K. J., Lin J., Hanasawa K., Tani T., Kodama M. Interleukin-8 as a predictor of the severity of bacteremia and infectious disease. *Shock* 2000;14:95–100; and Tabary O., Escotte S., Couetil J. P., Hubert D., Dusser D., Puchelle E., Jacquot J. High susceptibility for cystic fibrosis human airway gland cells to produce IL-8 through the I kappa B kinase alpha pathway in response to extracellular NaCl content. *J. Immunol.* 2000;164:3377–3384) and conversely, an antibody to IL-8 decreases the neutrophil recruitment to the site of injury (Dumont R. A., Car B. D., Voitenok N. N., Junker U., Moser B., Zak O., O'Reilly T. Systemic neutralization of interleukin-8 markedly reduces neutrophilic pleocytosis during experimental lipopolysaccharide-induced meningitis in rabbits. *Infect. Immun.* 2000;68:5756–5763).

Although the effector functions of IL-8 are fairly well-characterized, the signaling mechanisms induced by IL-8 receptors that mediate these functions are just beginning to be understood. It was shown previously that IL-8 induces calcium flux; however, it does not have a direct role in mediation of the chemotaxis (Ben-Baruch A., Bengali K. M., Biragyn A., Johnston J. J., Wang J. M., Kim J., Chunthrapi A., et al. Interleukin-8 receptor beta: The role of the carboxy terminus in signal transduction. *J. Biol. Chem.* 1995;270:9121–9128). Previous studies show that IL-8 activates phosphoinositide-3 kinase (PI3K) and also the Ras/ Raf/MAPK pathway and in turn activate extracellular regulated kinases (ERK) and p38, but not JNK (Yaffe M. B., Xu J., Burke P. A., Brown G. E. Priming of the neutrophil respiratory burst is species dependent and involves mitogen-activated protein kinase (MAPK) activation. *Surgery* 1999; 126:248–254; Shyamala V., Khoja H. Interleukin-8 receptors R1 and R2 activate mitogen-activated protein kinases and induce c-fos, independent of Ras and Raf-1 in Chinese hamster ovary cells. Biochemistry 1998;37:15918–15924; and Richardson R. M., Ali H., Pridgen B. C., Haribabu B., Snyderman R. Multiple signaling pathways of human interleukin-8 receptor A. Independent regulation by phosphorylation. *J. Biol. Chem.* 1998;273:10690–10695). Both small molecule inhibitors and knock out mice demonstrate a primary role for PI3K in chemokine-induced chemotaxis. However, the role of ERK is controversial. Previous studies that utilized 2-(2-amino-3-methoxy-phenyl)-chromen-4-one demonstrated a lack of inhibition of IL-8-induced chemotaxis (Knoll C., Worthen G. S., Johnson G. L. Interleukin 8-stimulated phosphatidylinositol-3-kinase activity regulates the migration of human neutrophils independent of extracellular signal-regulated kinase and p38 mitogen-activated protein kinases. *Proc. Natl. Acad. Sci.* 1997;94:3052–3057). Discovery efforts clearly show that 2-(2-amino-3-methoxy-phenyl)-chromen-4-one is much less efficacious and a orally nonbioavailable compound compared to recently developed compounds, such as 2-(2-chloro-4-iodo-phenylamino)-N-cyclopropylmethoxy-3,4-difluoro-benzamide. Hence, to address the potential role of ERK and PI3K in the IL-8-induced chemotaxis, a recently described (Sebolt-Leopold J. S., Dudley D. T., Herrera R., Van Becelaere K., Wiland A., Gowan R. C., Tecle H., et al. Blockade of the MAP kinase pathway suppresses growth of colon tumors in vivo. *Nat. Med.* 1999;5:810–816) bioavailable MEK inhibitor, 2-(2-chloro-4-iodo-phenylamino)-N-cyclopropylmethoxy-3,4-difluoro-benzamide, and Wortmannin were used. The results clearly demonstrate that IL-8 activates ERK in a time-dependent fashion and this can be clearly blocked by 2-(2-chloro-4-iodo-phenylamino)-N-cyclopropylmethoxy-3,4-difluoro-benzamide or Wortmannin. While Wortmannin can block 100% of the chemotaxis, 2-(2-chloro-4-iodo-phenylamino)-N-cyclopropylmethoxy-3,4-difluoro-benzamide blocks only 60% of the chemotaxis. The combination of Wortmannin and 2-(2-chloro-4-iodo-phenylamino)-N-cyclopropylmethoxy-3,4-difluoro-benzamide exhibit an additive inhibitory effect suggesting the possibility of two independent pathways leading to IL-8-induced chemotaxis. In a rabbit neutrophil, intradermal recruitment assay applicants demonstrate that IL-8-induced in vivo chemotaxis was blocked by ~50% after oral administration of 2-(2-chloro-4-iodo-phenylamino)-N-cyclopropylmethoxy-3,4-difluoro-benzamide. Accordingly, MEK is an important pathway responsible for IL-8 mediated chemotaxis, and blocking the MEK pathway could serve as an alternate strategy to combat neutrophil mediated diseases.

SUMMARY OF THE INVENTION

The present invention provides a method of inhibiting neutrophil migration/chemotaxis. The method comprises administering to a patient having a disease or condition including or characterized at least in part by neutrophil migration/chemotaxis or at risk of having neutrophil migration/chemotaxis, a therapeutically acceptable amount of a compound that is a MEK inhibitor. The method includes the further step of administering a therapeutically effective amount of a compound that is a PI3K inhibitor.

In an embodiment of the invention, the compound that is the MEK inhibitor is 2-(2-chloro-4-iodo-phenylamino)-N-cyclopropylmethoxy-3,4-difluoro-benzamide.

In another embodiment of the invention, the compound that is the MEK inhibitor is 2-(2-amino-3-methoxyphenyl)-4-oxo-4H-[1]benzopyran.

In a further embodiment of the invention, a therapeutically effective amount of a compound that is a PI3K inhibitor is also administered to the patient.

In another embodiment of the invention, the compound that is the PI3K inhibitor is Wortmannin.

The invention also provides a method of treating or preventing neutrophil migration/chemotaxis, the method comprising administering to a patient having neutrophil migration/chemotaxis, or at risk of having neutrophil migration/chemotaxis, a therapeutically acceptable amount of 2-(2-chloro-4-iodo-phenylamino)-N-cyclopropylmethoxy-3,4-difluoro-benzamide and Wortmannin.

Also provided in a preferred embodiment of the invention, the MEK inhibitor is a compound of Formula I

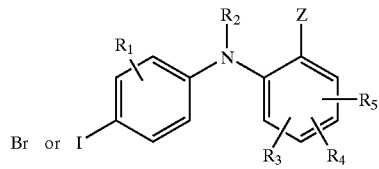

wherein:

$R_1$ is hydrogen, hydroxy, $C_1$–$C_8$ alkyl, $C_1$–$C_8$ alkoxy, halo, trifluoromethyl, or CN;

$R_2$ is hydrogen;

$R_3$, $R_4$, and $R_5$ independently are hydrogen, hydroxy, halo, trifluoromethyl, $C_1$–$C_8$ alkyl, $C_1$–$C_8$ alkoxy, nitro, CN, or —(O or NH)$_m$—(CH$_2$)$_n$—$R_9$, where $R_9$ is hydrogen, hydroxy, COOH, or $NR_{10}R_{11}$;

n is 0 to 4;

m is 0 or 1;

$R_{10}$ and $R_{11}$ independently are hydrogen or $C_1$–$C_8$ alkyl, or taken together with the nitrogen to which they are attached can complete a 3- to 10-member cyclic ring optionally containing 1, 2, or 3 additional heteroatoms selected from O, S, NH, or N—$C_1$–$C_8$ alkyl;

Z is $COOR_7$, tetrazolyl, $CONR_6R_7$, $CONHNR_{10}R_{11}$, or $CH_2OR_7$;

$R_6$ and $R_7$ independently are hydrogen, $C_1$–$C_8$ alkyl, $C_2$–$C_8$ alkenyl, $C_2$–$C_8$ alkynyl,

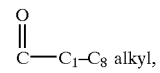

aryl, heteroaryl, $C_3$–$C_{10}$ cycloalkyloptionally containing one, two, or three heteroatoms selected from O, S, NH, or N alkyl; or $R_6$ and $R_7$ together with the nitrogen to which they are attached complete a 3- to 10-member cyclic ring optionally containing 1, 2, or 3 additional heteroatoms selected from O, S, NH, or N alkyl; and wherein any of the foregoing alkyl, alkenyl, and alkynyl groups can be unsubstituted or substituted by halo, hydroxy, alkoxy, amino, alkylamino, dialkylamino, cycloalkyl, aryl, aryloxy, heteroaryl, or heteroaryloxy, and the pharmaceutically acceptable salts, esters, amides, or prodrugs thereof.

In a more preferred embodiment, the MEK inhibitor is

[4-Chloro-2-(1H-tetrazol-5-yl)-(4-iodo-2-methyl-phenyl)-amine;
(4-iodo-2-methyl-phenyl)-[2-(1H-tetrazol-5-yl)-phenyl]amine;
[4-nitro-2-(1H-tetrazol-5-yl)-(4-iodo-2-methyl-phenyl)-amine;
4-Fluoro-2-(4-iodo-2-methylphenylamino)benzoic acid;
3,4,5-Trifluoro-2-(4-iodo-2-methyl-phenylamino)-benzoic acid;
3,4-Difluoro-2-(4-iodo-2-methyl-phenylamino)-benzoic acid;
5-Bromo-3,4-difluoro-2-(4-iodo-2-methyl-phenylamino)-benzoic acid;
5-Chloro-2-(4-iodo-2-methyl-phenylamino)-benzoic acid;
Sodium 5-Chloro-2-(4-iodo-2-methyl-phenylamino)-benzoate;
5-Bromo-2-(4-iodo-2-methyl-phenylamino)-benzoic acid;
2-(4-Iodo-2-methyl-phenylamino)-5-nitro-benzoic acid;

4-Chloro-2-(4-iodo-2-methyl-phenylamino)-benzoic acid;
2-(4-Iodo-2-methyl-phenylamino)-benzoic acid;
5-Fluoro-2-(4-iodo-2-methyl-phenylamino)-benzoic acid;
5-Iodo-2-(4-iodo-2-methyl-phenylamino)-benzoic acid;
2,3,5-Trifluoro-4-(4-iodo-2-methyl-phenylamino)-benzoic acid;
2-(4-Iodo-phenylamino)-5-methoxy-benzoic acid;
5-Methyl-2-(4-iodo-2-methyl-phenylamino)-benzoic acid;
2-(4-Iodo-2-methyl-phenylamino)-4-nitro-benzoic acid;
2-(4-Bromo-2-methyl-phenylamino)-4-fluoro-benzoic acid;
2-(2-Bromo-4-iodo-phenylamino)-5-nitro-benzoic acid;
2-(4-Bromo-2-methyl-phenylamino)-3,4-difluoro-benzoic acid;
5-Chloro-N-(2-hydroxyethyl)-2-(4-iodo-2-methyl-phenylamino)-benzamide;
4-Fluoro-2-(4-iodo-2-methyl-phenylamino)-benzamide;
4-Fluoro-2-(4-iodo-2-methyl-phenylamino)-N-methyl-benzamide;
N-Ethyl-4-fluoro-2-(4-iodo-2-methyl-phenylamino)-benzamide;
4-Fluoro-2-(4-iodo-2-methyl-phenylamino)-N,N-dimethyl-benzamide;
4-Fluoro-2-(4-iodo-2-methyl-phenylamino)-N-(11H-tetrazol-5-yl)-benzamide;
5-Bromo-2-(4-iodo-2-methyl-phenylamino)-benzamide;
5-Chloro-2-(4-iodo-2-methyl-phenylamino)-N,N-dimethyl-benzamide;
[5-Chloro-2-(4-iodo-2-methyl-phenylamino)-benzoylamino]-acetic acid;
4-Fluoro-2-(4-iodo-2-methyl-phenylamino)-N-propyl-benzamide;
5-Bromo-N-(2-hydroxy-ethyl)-2-(4-iodo-2-methyl-phenylamino)-benzamide;
N,N-Diethyl-4-fluoro-2-(4-iodo-2-methyl-phenylamino)-benzamide;
4-Fluoro-N-{3-[4-(2-hydroxy-ethyl)-piperazin-1-yl]-propyl}-2-(4-iodo-2-methyl-phenylamino)-benzamide;
N,N-Diethyl-2-(4-iodo-2-methyl-phenylamino)-5-nitro-benzamide;
N-Butyl-4-fluoro-2-(4-iodo-2-methyl-phenylamino)-benzamide;
5-Chloro-N,N-diethyl-2-(4-iodo-2-methyl-phenylamino)-benzamide;
5-Bromo-2-(4-iodo-2-methyl-phenylamino)-N,N-dimethyl-benzamide;
5-Bromo-3,4-difluoro-N-(2-hydroxy-ethyl)-2-(4-iodo-2-methyl-phenylamino)-benzamide;
N-(2,3-Dihydroxy-propyl)-3,4-difluoro-2-(4-iodo-2-methyl-phenylamino)-benzamide;
5-Bromo-3,4-difluoro-2-(4-iodo-2-methyl-phenylamino)-N-(2-piperidin-1-yl-ethyl)-benzamide;
3,4-Difluoro-N-(2-hydroxy-ethyl)-2-(4-iodo-2-methyl-phenylamino)-benzamide;
N-(2,3-Dihydroxy-propyl)-4-fluoro-2-(4-iodo-2-methyl-phenylamino)-benzamide;
3,4-Difluoro-N-(3-hydroxy-propyl)-2-(4-iodo-2-methyl-phenylamino)-benzamide;
5-Bromo-3,4-difluoro-2-(4-iodo-2-methyl-phenylamino)-N-(2-pyrrolidin-1-yl-ethyl)-benzamide;
5-Bromo-3,4-difluoro-2-(4-iodo-2-methyl-phenylamino)-N-(2-pyridin-4-yl-ethyl)-benzamide;
4-Fluoro-N-(2-hydroxy-ethyl)-2-(4-iodo-2-methyl-phenylamino)-benzamide;
5-Bromo-N-(3-dimethylamino-propyl)-3,4-difluoro-2-(4-iodo-2-methyl-phenylamino)-benzamide;
5-Bromo-3,4-difluoro-2-(4-iodo-2-methyl-phenylamino)-N-(2-morpholin-4-yl-ethyl)-benzamide;
3,4-Difluoro-2-(4-iodo-2-methyl-phenylamino)-N-(2-morpholin-4-yl-ethyl)-benzamide;
3,4-Difluoro-2-(4-iodo-2-methyl-phenylamino)-N-(2-pyrrolidin-1-yl-ethyl)-benzamide;
3,4-Difluoro-2-(4-iodo-2-methyl-phenylamino)-N-(2-pyridin-4-yl-ethyl)-benzamide;
N-(3-Dimethylamino-propyl)-3,4-difluoro-2-(4-iodo-2-methyl-phenylamino)-benzamide;
N-Benzyl-4-fluoro-2-(4-iodo-2-methyl-phenylamino)-benzamide;
2-(4-Bromo-2-methyl-phenylamino)-3,4-difluoro-N-(2-hydroxy-ethyl)-benzamide;
4-Fluoro-2-(4-iodo-2-methyl-phenylamino)-N-(2-morpholin-4-yl-ethyl)-benzamide;
4-Fluoro-2-(4-iodo-2-methyl-phenylamino)-N-(3-piperidin-1-yl-propyl)-benzamide;
3,4-Difluoro-2-(4-iodo-2-methyl-phenyl amino)-N-(3-piperidin-1-yl-propyl)-benzamide;
4-Fluoro-2-(4-iodo-2-methyl-phenylamino)-N-(2-thiophen-2-yl-ethyl)-benzamide;
4-Fluoro-2-(4-iodo-2-methyl-phenylamino)-N-(2-pyrrolidin-1-yl-ethyl)-benzamide;
2-(4-Bromo-2-methyl-phenylamino)-3,4-difluoro-N-(2-morpholin-4-yl-ethyl)-benzamide;
5-Bromo-3,4-difluoro-2-(4-iodo-2-methyl-phenylamino)-N-pyridin-4-ylmethyl-benzamide;
3,4-Difluoro-2-(4-iodo-2-methyl-phenylamino)-N-pyridin-4-ylmethyl-benzamide;
2-(4-Bromo-2-methyl-phenylamino)-N-(3-dimethylamino-propyl)-3,4-difluoro-benzamide;
4-Fluoro-2-(4-iodo-2-methyl-phenylamino)-N-pyridin-4-ylmethyl-benzamide;
4-Fluoro-2-(4-iodo-2-methyl-phenylamino)-N-(2-pyridin-4-yl-ethyl)-benzamide;
2-(4-Bromo-2-methyl-phenylamino)-3,4-difluoro-N-(2-pyridin-4-yl-ethyl)-benzamide;
2-(4-Bromo-2-methyl-phenylamino)-3,4-difluoro-N-(3-hydroxy-propyl)-benzamide;
2-(4-Bromo-2-methyl-phenylamino)-3,4-difluoro-N-(2-pyrrolidin-1-yl-ethyl)-benzamide;
4-Fluoro-2-(4-iodo-2-methyl-phenylamino)-N-phenethyl-benzamide;
2-(4-Bromo-2-methyl-phenylamino)-3,4-difluoro-N-(2-thiophen-2-yl-ethyl)-benzamide;
2-(4-Bromo-2-methyl-phenylamino)-3,4-difluoro-N-pyridin-4-ylmethyl-benzamide;
2-(4-Bromo-2-methyl-phenylamino)-3,4-difluoro-N-phenethyl-benzamide;
2-(4-Bromo-2-methyl-phenylamino)-3,4-difluoro-N-(2-piperidin-1-yl-ethyl)-benzamide;
5-Chloro-N-{3-[4-(2-hydroxy-ethyl)-piperazin-1-yl]-propyl}-2-(4-iodo-2-methyl-phenylamino)-benzamide;
5-Fluoro-N-{3-[4-(2-hydroxy-ethyl)-piperazin-1-yl]-propyl}-2-(4-iodo-2-methyl-phenylamino)-benzamide;
2-(4-Iodo-2-methyl-phenylamino)-5-nitro-N-pyridin-4-yl methyl-benzamide;
5-Bromo-N-{3-[4-(2-hydroxy-ethyl)-piperazin-1-yl]-propyl}-2-(4-iodo-2-methyl-phenylamino)-benzamide;
5-Chloro-N-(2-diethylamino-ethyl)-2-(4-iodo-2-methyl-phenylamino)-benzamide;
5-Chloro-2-(4-iodo-2-methyl-phenylamino)-N-(2-piperidin-1-yl-ethyl)-benzamide;
(3-Hydroxy-pyrrolidin-1-yl)-[2-(4-iodo-2-methyl-phenylamino)-5-nitro-phenyl];
5-Chloro-2-(4-iodo-2-methyl-phenylamino)-N-(2-pyrrolidin-1-yl-ethyl)-benzamide;
5-Bromo-N-(2-diethylamino-ethyl)-2-(4-iodo-2-methyl-phenylamino)-benzamide;

N-{2-[Bis-(2-hydroxy-ethyl)-amino]-ethyl}-5-chloro-2-(4-iodo-2-methyl-phenylamino)-benzamide;
N-{2-[Bis-(2-hydroxy-ethyl)-amino]-ethyl}-5-bromo-2-(4-iodo-2-methyl-phenylamino)-benzamide;
N-{3-[4-(2-Hydroxy-ethyl)-piperazin-1-yl]-propyl}-2-(4-iodo-2-methyl-phenylamino)-benzamide;
5-Fluoro-2-(4-iodo-2-methyl-phenylamino)-N-pyridin-4-ylmethyl-benzamide;
5-Bromo-2-(4-iodo-2-ethyl-phenylamino)-N-(2-pyrrolidin-1-yl-ethyl)-benzamide;
5-Bromo-2-(4-iodo-2-methyl-phenylamino)-N-(2-piperidin-1-yl-ethyl)-benzamide;
5-Fluoro-2-(4-iodo-2-methyl-phenylamino)-N-(2-pyrrolidin-1-yl-ethyl)-benzamide;
5-Chloro-N-(3-dimethylamino-propyl)-2-(4-iodo-2-methyl-phenylamino)-benzamide;
N-{2-[Bis-(2-hydroxy-ethyl)-amino]-ethyl}-5-fluoro-2-(4-iodo-2-methyl-phenylamino)-benzamide;
5-Chloro-N-(3-hydroxy-propyl)-2-(4-iodo-2-methyl-phenylamino)-benzamide;
5-Chloro-N-(3-diethylamino-2-hydroxy-propyl)-2-(4-iodo-2-methyl-phenylamino)-benzamide;
5-Fluoro-2-(4-iodo-2-methyl-phenylamino)-N-(2-piperidin-1-yl-ethyl)-benzamide;
5-Bromo-N-(3-hydroxy-propyl)-2-(4-iodo-2-methyl-phenylamino)-benzamide;
5-Bromo-2-(4-iodo-2-methyl-phenylamino)-N-(3-piperidin-1-yl-propyl)-benzamide;
N-{2-[Bis-(2-hydroxy-ethyl)-amino]-ethyl}-2-(4-iodo-2-methyl-phenylamino)-5-nitro-benzamide;
5-Chloro-2-(4-iodo-2-methyl-phenylamino)-N-(2-morpholin-4-yl-ethyl)-benzamide;
5-Chloro-N-(3-diethylamino-propyl)-2-(4-iodo-2-methyl-phenylamino)-benzamide;
5-Chloro-N-(2-diisopropylamino-ethyl)-2-(4-iodo-2-methyl-phenylamino)-benzamide;
5-Chloro-2-(4-iodo-2-methyl-phenylamino)-N-(3-piperidin-1-yl-propyl)-benzamide;
2-(4-Iodo-2-methyl-phenylamino)-5-nitro-N-(2-piperidin-1-yl-ethyl)-benzamide;
5-Bromo-2-(4-iodo-2-methyl-phenylamino)-N-(2-piperazin-1-yl-ethyl)-benzamide;
N-(2-Diethylamino-ethyl)-5-fluoro-2-(4-iodo-2-methyl-phenylamino)-benzamide;
5-Bromo-N-(3-dimethylamino-propyl)-2-(4-iodo-2-methyl-phenylamino)-benzamide;
N-(3-Hydroxy-propyl)-2-(4-iodo-2-methyl-phenylamino)-5-nitro-benzamide;
5-Fluoro-N-(3-hydroxy-propyl)-2-(4-iodo-2-methyl-phenylamino)-benzamide;
N-(3-Diethylamino-propyl)-5-fluoro-2-(4-iodo-2-methyl-phenylamino)-benzamide;
N-(3-Diethylamino-propyl)-2-(4-iodo-2-methyl-phenylamino)-5-nitro-benzamide;
5-Bromo-2-(4-iodo-2-methyl-phenylamino)-N-(2-morpholin-4-yl-ethyl)-benzamide;
2-(4-Iodo-2-methyl-phenylamino)-5-nitro-N-(3-piperidin-1-yl-propyl)-benzamide;
[5-Fluoro-2-(4-iodo-2-methyl-phenylamino)-phenyl]-(3-hydroxy-pyrrolidin-1-yl)-;
5-Bromo-N-(2-diisopropylamino-ethyl)-2-(4-iodo-2-methyl-phenylamino)-benzamide;
5-Fluoro-2-(4-iodo-2-methyl-phenylamino)-N-(2-morpholin-4-yl-ethyl)-benzamide;
5-Fluoro-2-(4-iodo-2-methyl-phenylamino)-N-(3-piperidin-1-yl-propyl)-benzamide;
[5-Fluoro-2-(4-iodo-2-methyl-phenylamino)-phenyl]-[4-(2-hydroxy-ethyl)-piperazin-1-;
N-(3-Diethylamino-2-hydroxy-propyl)-5-fluoro-2-(4-iodo-2-methyl-phenylamino)-benzamide;
N-Cyclopropyl-5-fluoro-2-(4-iodo-2-methyl-phenylamino)-benzamide;
5-Chloro-N-(2-hydroxy-ethyl)-2-(4-iodo-2-methyl-phenylamino)-benzamide;
5-Fluoro-N-(2-hydroxy-ethyl)-2-(4-iodo-2-methyl-phenylamino)-benzamide;
N-Benzyloxy-5-fluoro-2-(4-iodo-2-methyl-phenylamino)-benzamide;
N-Benzyloxy-5-bromo-2-(4-iodo-2-methyl-phenylamino)-benzamide;
2-(4-Iodo-2-methyl-phenylamino)-5-nitro-N-(4-sulfamoyl-benzyl)-benzamide;
5-Bromo-N-(2-hydroxy-ethyl)-2-(4-iodo-2-methyl-phenylamino)-benzamide;
N-(2-Hydroxy-ethyl)-5-iodo-2-(4-iodo-2-methyl-phenylamino)-benzamide;
N-(2-Hydroxy-ethyl)-2-(4-iodo-2-ethyl-phenylamino)-5-nitro-benzamide;
2-(4-Iodo-2-methyl-phenylamino)-N-methyl-5-nitro-N-phenyl-benzamide;
5-Chloro-N-cyclopropyl-2-(4-iodo-2-methyl-phenylamino)-benzamide;
5-Fluoro-2-(4-iodo-2-methyl-phenylamino)-N-methyl-N-phenyl-benzamide;
N-Allyl-5-fluoro-2-(4-iodo-2-methyl-phenylamino)-benzamide;
N-Benzyloxy-5-iodo-2-(4-iodo-2-methyl-phenylamino)-benzamide;
5-Fluoro-2-(4-iodo-2-methyl-phenylamino)-N-(4-sulfamoyl-benzyl)-benzamide;
N-Allyl-5-chloro-2-(4-iodo-2-methyl-phenylamino)-benzamide;
N-Cyclopropyl-2-(4-iodo-2-methyl-phenylamino)-5-nitro-benzamide;
5-Bromo-N-cyclopropyl-2-(4-iodo-2-methyl-phenylamino)-benzamide;
5-Chloro-2-(4-iodo-2-methyl-phenylamino)-N-methyl-N-phenyl-benzamide;
5-Iodo-2-(4-iodo-2-methyl-phenylamino)-N-(4-sulfamoyl-benzyl)-benzamide;
5-Bromo-2-(4-iodo-2-methyl-phenylamino)-N-(4-sulfamoyl-benzyl)-benzamide;
N-Allyl-2-(4-iodo-2-methyl-phenylamino)-5-nitro-benzamide;
2-(4-Iodo-2-methyl-phenylamino)-5-nitro-N-(4-sulfamoyl-benzyl)-benzamide;
N-Allyl-5-bromo-2-(4-iodo-2-methyl-phenylamino)-benzamide;
5-Fluoro-2-(4-iodo-2-methyl-phenylamino)-N-(3-methyl-benzyl)-benzamide;
N-Cyclopropyl-5-iodo-2-(4-iodo-2-methyl-phenylamino)-benzamide;
5-Bromo-2-(4-iodo-2-methyl-phenylamino)-N-methyl-N-phenyl-benzamide;
N-Benzyloxy-2-(4-iodo-2-methyl-phenylamino)-5-nitro-benzamide;
N-Cyclohexyl-5-iodo-2-(4-iodo-2-methyl-phenylamino)-benzamide;
N-Allyl-5-iodo-2-(4-iodo-2-methyl-phenylamino)-benzamide;
5-Iodo-2-(4-iodo-2-methyl-phenylamino)-N-(3-methyl-benzyl)-benzamide;
2-(4-Iodo-2-methyl-phenylamino)-N-(3-methyl-benzyl)-5-nitro-benzamide;
5-Iodo-2-(4-iodo-2-methyl-phenylamino)-N-methyl-N-phenyl-benzamide;

N-Cyclohexyl-5-fluoro-2-(4-iodo-2-methyl-phenylamino)-benzamide;
5-Chloro-N-cyclohexyl-2-(4-iodo-2-methyl-phenylamino)-benzamide;
5-Bromo-2-(4-iodo-2-methyl-phenylamino)-N-(3-methyl-benzyl)-benzamide;
5-Bromo-N-cyclohexyl-2-(4-iodo-2-methyl-phenylamino)-benzamide;
5-Chloro-2-(4-iodo-2-methyl-phenylamino)-N-(3-methyl-benzyl)-benzamide;
N-Cyclohexyl-2-(4-iodo-2-methyl-phenylamino)-5-nitro-benzamide;
N-Benzyloxy-5-bromo-2-(4-iodo-2-methyl-phenylamino)-benzamide;
N-Benzyloxy-5-fluoro-2-(4-iodo-2-methyl-phenylamino)-benzamide;
5-Chloro-N-(2-hydroxy-ethyl)-2-(4-iodo-2-methyl-phenylamino)-benzamide;
5-Bromo-N-(2-hydroxy-ethyl)-2-(4-iodo-2-methyl-phenylamino)-benzamide;
2-(4-Iodo-2-methyl-phenylamino)-N-methyl-5-nitro-N-phenyl-benzamide;
5-Chloro-2-(4-iodo-2-methyl-phenylamino)-N-methyl-N-phenyl-benzamide;
N-(2-Hydroxy-ethyl)-5-iodo-2-(4-iodo-2-methyl-phenylamino)-benzamide;
5-Chloro-N-cyclopropyl-2-(4-iodo-2-methyl-phenylamino)-benzamide;
N-Allyl-5-chloro-2-(4-iodo-2-methyl-phenylamino)-benzamide;
5-Fluoro-2-(4-iodo-2-methyl-phenylamino)-N-methyl-N-phenyl-benzamide;
N-(2-Hydroxy-ethyl)-2-(4-iodo-2-methyl-phenylamino)-5-nitro-benzamide;
5-Fluoro-N-(2-hydroxy-ethyl)-2-(4-iodo-2-methyl-phenylamino)-benzamide;
5-Bromo-N-cyclopropyl-2-(4-iodo-2-methyl-phenylamino)-benzamide;
N-Cyclopropyl-5-fluoro-2-(4-iodo-2-methyl-phenylamino)-benzamide;
5-Fluoro-2-(4-iodo-2-methyl-phenylamino)-N-(4-sulfamoyl-benzyl)-benzamide;
N-Cyclopropyl-2-(4-iodo-2-methyl-phenylamino)-5-nitro-benzamide;
N-Allyl-5-fluoro-2-(4-iodo-2-methyl-phenylamino)-benzamide;
N-Benzyloxy-5-iodo-2-(4-iodo-2-methyl-phenylamino)-benzamide;
N-Allyl-5-bromo-2-(4-iodo-2-methyl-phenylamino)-benzamide;
5-Bromo-2-(4-iodo-2-methyl-phenylamino)-N-(4-sulfamoyl-benzyl)-benzamide;
5-Bromo-2-(4-iodo-2-methyl-phenylamino)-N-methyl-N-phenyl-benzamide;
N-Allyl-2-(4-iodo-2-methyl-phenylamino)-5-nitro-benzamide;
4-Fluoro-2-(4-iodo-2-methyl-phenylamino)-benzyl alcohol;
[5-Chloro-2-(4-iodo-2-methyl-phenylamino)-phenyl]-methanol;
[2-(4-Iodo-2-methyl-phenylamino)-5-nitro-phenyl]-methanol;
[5-Bromo-2-(4-iodo-2-methyl-phenylamino)-phenyl]-methanol; or
N-Allyl-2-(4-iodo-2-methyl-phenylamino)-5-nitro-benzamide.

In another embodiment, the MEK inhibitor is a compound of Formula II

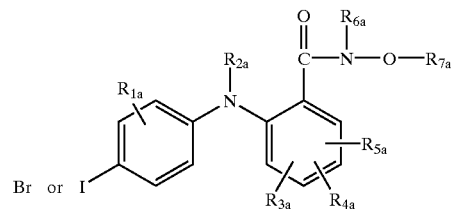

wherein:

$R_{1a}$ is hydrogen, hydroxy, $C_1$–$C_8$ alkyl, $C_1$–$C_8$ alkoxy, halo, trifluoromethyl, or CN;
R2a is hydrogen;
$R_{3a}$, $R_{4a}$, and $R_{5a}$ independently are hydrogen, hydroxy, halo, trifluoromethyl, $C_1$–$C_8$ alkyl, $C_1$–$C_8$ alkoxy, nitro, CN, or (O or NH)$_m$—(CH$_2$)$_n$—$R_{9a}$, where $R_{9a}$ is hydrogen, hydroxy, $CO_2H$ or $NR_{10a}R_{11a}$;
n is 0 to 4;
m is 0 or 1;
$R_{10a}$ and $R_{11a}$ independently are hydrogen or $C_1$–$C_8$ alkyl, or taken together with the nitrogen to which they are attached can complete a 3- to 10-member cyclic ring optionally containing one, two, or three additional heteroatoms selected from O, S, NH, or N—$C_1$–$C_8$ alkyl;
$R_{6a}$ is hydrogen, $C_1$–$C_8$ alkyl,

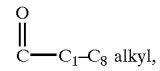

aryl, aralkyl, or $C_3$–$C_{10}$ cycloalkyl;
$R_{7a}$ is hydrogen, $C_1$–$C_8$ alkyl, $C_2$–$C_8$ alkenyl, $C_2$–$C_8$ alkynyl, $C_3$–$C_{10}$ cycloalkyl optionally containing a heteroatom selected from O, S, or $NR_{9a}$; and
wherein any of the foregoing alkyl, alkenyl, and alkynyl groups can be unsubstituted or substituted by cycloalkyl, aryl, aryloxy, heteroaryl, or heteroaryloxy; or $R_{6a}$ and $R_{7a}$ taken together with the N to which they are attached can complete a 5- to 10-membered cyclic ring, optionally containing one, two, or three additional heteroatoms selected from O, S, or $NR_{10a}R_{11a}$, and the pharmaceutically acceptable salts, esters, amides or prodrugs thereof.

In a further embodiment the MEK inhibitor is

4-Fluoro-N-hydroxy-2-(4-iodo-2-methyl-phenylamino)-benzamide;
4-Fluoro-2-(4-iodo-2-methyl-phenylamino)-N-(methoxy)-benzamide;
4-Fluoro-2-(4-iodo-2-methyl-phenylamino)-N-(prop-2-ynyloxy)-benzamide;
4-Fluoro-2-(4-iodo-2-methyl-phenylamino)-N-(2-phenoxyethoxy)-benzamide;
4-Fluoro-2-(4-iodo-2-methyl-phenylamino)-N-(2-thienylmethoxy)-benzamide;
4-Fluoro-2-(4-iodo-2-methyl-phenylamino)-N-(prop-2-enyloxy)-benzamide;
4-Fluoro-2-(4-iodo-2-methyl-phenylamino)-N-(cyclopropylmethoxy)-benzamide;
4-Fluoro-2-(4-iodo-2-methyl-phenylamino)-N-(cyclopentoxy)-benzamide;
3,4-Difluoro-2-(4-iodo-2-methyl-phenylamino)-N-(3-furylmethoxy)-benzamide;
3,4-Difluoro-2-(4-iodo-2-methyl-phenylamino)-N-ethoxy-benzamide;

3,4-Difluoro-2-(4-iodo-2-methyl-phenylamino)-N-(but-2-enyloxy)-benzamide;
3,4-Difluoro-2-(4-iodo-2-methyl-phenylamino)-N-(cyclopropylmethoxy)-benzamide;
3,4-Difluoro-2-(4-iodo-2-methyl-phenylamino)-N-(1-methylprop-2-ynyloxy)-benzamide;
3,4-Difluoro-2-(4-iodo-2-methyl-phenylamino)-N-(3-phenylprop-2-ynyloxy)-benzamide;
3,4-Difluoro-2-(4-iodo-2-methyl-phenylamino)-N-(3-methyl-5-phenylpent-2-en-4-ynyloxy)-benzamide;
3,4-Difluoro-2-(4-iodo-2-methyl-phenylamino)-N-(prop-2-ynyloxy)-benzamide;
3,4-Difluoro-2-(4-iodo-2-methyl-phenylamino)-N-(propoxy)-benzamide;
3,4-Difluoro-2-(4-iodo-2-methyl-phenylamino)-N-(cyclobutyloxy)-benzamide;
3,4-Difluoro-2-(4-iodo-2-methyl-phenylamino)-N-(2-thienylmethoxy)-benzamide;
3,4-Difluoro-2-(4-iodo-2-methyl-phenylamino)-N-(2-methyl-prop-2-enyloxy)-benzamide;
3,4-Difluoro-2-(4-iodo-2-methyl-phenylamino)-N-(2-phenoxyethoxy)-benzamide;
3,4-Difluoro-2-(4-iodo-2-methyl-phenylamino)-N-(but-2-enyloxy)-benzamide;
3,4-Difluoro-2-(4-iodo-2-methyl-phenylamino)-N-(but-3-ynyloxy)-benzamide;
3,4-Difluoro-2-(4-iodo-2-methyl-phenylamino)-N-(cyclopentyloxy)-benzamide;
3,4-Difluoro-2-(4-iodo-2-methyl-phenylamino)-N-(3-(2-fluorophenyl)-prop-2-ynyloxy)-benzamide;
5-Bromo-3,4-difluoro-N-hydroxy-2-(4-iodo-2-methyl-phenylamino)-benzamide;
5-Bromo-3,4-difluoro-2-(4-iodo-2-methyl-phenylamino)-N-(n-propoxy)-benzamide;
5-Bromo-3,4-difluoro-N-(furan-3-ylmethoxy)-2-(4-iodo-2-methyl-phenylamino)-benzamide;
5-Bromo-N-(but-2-enyloxy)-3,4-difluoro-2-(4-iodo-2-methyl-phenylamino)-benzamide
5-Bromo-N-butoxy-3,4-difluoro-2-(4-iodo-2-methyl-phenylamino)-benzamide;
5-Bromo-3,4-difluoro-2-(4-iodo-2-methyl-phenylamino)-N-(3-methyl-but-2-enyloxy)-benzamide;
5-Bromo-3,4-difluoro-2-(4-iodo-2-methyl-phenylamino)-N-(3-methyl-pent-2-en-4-ynyloxy)-benzamide;
5-Bromo-3,4-difluoro-2-(4-iodo-2-methyl-benzyl)-N-[5-(3-methoxy-phenyl)-3-methyl-pent-2-en-4-ynyloxy]-benzamide;
5-Bromo-3,4-difluoro-2-(4-iodo-2-methyl-phenylamino)-N-(prop-2-ynyloxy)-benzamide;
5-Bromo-3,4-difluoro-2-(4-iodo-2-methyl-phenylamino)-N-[3-(3-methoxy-phenyl)-prop-2-ynyloxy]-benzamide;
5-Bromo-3,4-difluoro-2-(4-iodo-2-methyl-phenylamino)-N-(thiopen-2-ylmethoxy)-benzamide;
5-Bromo-3,4-difluoro-2-(4-iodo-2-methyl-phenylamino)-N-(pyridin-3-ylmethoxy)-benzamide;
5-Bromo-3-4-difluoro-2-(4-iodo-2-methyl-phenylamino)-N-(3-(2-fluorophenyl)-prop-2-ynyloxy)-benzamide;
5-Bromo-3,4-difluoro-2-(4-iodo-2-methyl-phenylamino)-N-(ethoxy)-benzamide;
5-Bromo-3,4-difluoro-2-(4-iodo-2-methyl-phenylamino)-N-(cyclopropylmethoxy)-benzamide;
5-Bromo-3,4-difluoro-2-(4-iodo-2-methyl-phenylamino)-N-(isopropoxy)-benzamide;
5-Bromo-3,4-difluoro-2-(4-iodo-2-methyl-phenylamino)-N-but-3-ynyloxy)-benzamide;
5-Chloro-N-hydroxy-2-(4-iodo-2-methyl-phenylamino)-benzamide;
5-Chloro-2-(4-iodo-2-methyl-phenylamino)-N-(tetrahydropyran-2-yloxy)-benzamide;
5-Chloro-2-(4-iodo-2-methyl-phenylamino)-N-methoxy-benzamide;
4-Bromo-2-(4-iodo-2-methyl-phenylamino)-N-phenylmethoxy-benzamide;
4-Fluoro-2-(4-iodo-2-methyl-phenylamino)-N-phenylmethoxy-benzamide;
5-Fluoro-N-hydroxy-2-(4-iodo-2-methyl-phenylamino)-benzamide;
5-Iodo-2-(4-iodo-2-methyl-phenylamino)-N-phenylmethoxy-benzamide;
5-Fluoro-2-(4-iodo-2-methyl-phenylamino)-N-(tetrahydropyran-2-yloxy)-benzamide;
3,4-Difluoro-2-(4-bromo-2-methyl-phenylamino)-N-(3-phenylprop-2-ynyloxy)-benzamide;
3,4-Difluoro-2-(4-bromo-2-methyl-phenylamino)-N-(3-furylmethoxy)-benzamide;
3,4-Difluoro-2-(4-bromo-2-methyl-phenylamino)-N-(2-thienylmethoxy)-benzamide;
3,4-Difluoro-2-(4-bromo-2-methyl-phenylamino)-N-(but-3-ynyloxy)-benzamide;
3,4-Difluoro-2-(4-bromo-2-methyl-phenylamino)-N-(2-methyl-prop-2-enyloxy)-benzamide;
3,4-Difluoro-2-(4-bromo-2-methyl-phenylamino)-N-(but-2-enyloxy)-benzamide;
3,4-Difluoro-2-(4-bromo-2-methyl-phenylamino)-N-(methoxy)-benzamide;
3,4-Difluoro-2-(4-bromo-2-methyl-phenylamino)-N-(ethoxy)-benzamide;
3,4-Difluoro-2-(4-bromo-2-methyl-phenylamino)-N-(cyclobutoxy)-benzamide;
3,4-Difluoro-2-(4-bromo-2-methyl-phenylamino)-N-(isopropoxy)-benzamide;
3,4-Difluoro-2-(4-bromo-2-methyl-phenylamino)-N-(2-phenoxyethoxy)-benzamide;
3,4-Difluoro-2-(4-bromo-2-methyl-phenylamino)-N-(cyclopropylmethoxy)-benzamide;
3,4-Difluoro-2-(4-bromo-2-methyl-phenylamino)-N-(n-propoxy)-benzamide;
3,4-Difluoro-2-(4-bromo-2-methyl-phenylamino)-N-(1-methyl-prop-2-ynyloxy)-benzamide;
3,4-Difluoro-2-(4-bromo-2-methyl-phenylamino)-N-(3-(3-fluorophenyl)-prop-2-ynyloxy)-benzamide;
3,4-Difluoro-2-(4-bromo-2-methyl-phenylamino)-N-(4,4-dimethylpent-2-ynyloxy)-benzamide;
3,4-Difluoro-2-(4-bromo-2-methyl-phenylamino)-N-(cyclopentoxy)-benzamide;
3,4,5-Trifluoro-N-hydroxy-2-(4-iodo-2-methyl-phenyl amino)-benzamide;
5-Chloro-3,4-difluoro-N-hydroxy-2-(4-iodo-2-methyl-phenylamino)-benzamide;
5-Bromo-3,4-difluoro-2-(2-fluoro-4-iodo-phenylamino)-N-hydroxy-benzamide;
N-Hydroxy-2-(4-iodo-2-methyl-phenylamino)-4-nitro-benzamide;
3,4,5-Trifluoro-2-(2-fluoro-4-iodo-phenylamino)-N-hydroxy-benzamide;
5-Chloro-3,4-difluoro-2-(2-fluoro-4-iodo-phenylamino)-N-hydroxy-benzamide;
5-Bromo-2-(2-chloro-4-iodo-phenylamino)-3,4-difluoro-N-hydroxy-benzamide;
2-(2-Fluoro-4-iodo-phenylamino)-N-hydroxy-4-nitro-benzamide;
2-(2-Chloro-4-iodo-phenylamino)-3,4,5-trifluoro-N-hydroxy-benzamide;
5-Chloro-2-(2-chloro-4-iodo-phenylamino)-3,4-difluoro-N-hydroxy-benzamide;

5-Bromo-2-(2-bromo-4-iodo-phenylamino)-3,4-difluoro-N-hydroxy-benzamide;
2-(2-Chloro-4-iodo-phenylamino)-N-hydroxy-4-methyl-benzamide;
2-(2-Bromo-4-iodo-phenylamino)-3,4,5-trifluoro-N-hydroxy-benzamide;
2-(2-Bromo-4-iodo-phenylamino)-5-chloro-3,4-difluoro-N-hydroxy-benzamide;
2-(2-Bromo-4-iodo-phenylamino)-N-hydroxy-4-nitro-benzamide;
4-Fluoro-2-(2-fluoro-4-iodo-phenylamino)-N-hydroxy-benzamide;
3,4-Difluoro-2-(2-fluoro-4-iodo-phenylamino)-N-hydroxy-benzamide;
2-(2-Chloro-4-iodo-phenylamino)-4-fluoro-N-hydroxy-benzamide;
2-(2-Chloro-4-iodo-phenylamino)-3,4-difluoro-N-hydroxy-benzamide;
2-(2-Bromo-4-iodo-phenylamino)-4-fluoro-N-hydroxy-benzamide;
2-(2-Bromo-4-iodo-phenylamino)-3,4-difluoro-N-hydroxy-benzamide;
N-Cyclopropylmethoxy-3,4,5-trifluoro-2-(4-iodo-2-methyl-phenylamino)-benzamide;
5-Chloro-N-cyclopropylmethoxy-3,4-difluoro-2-(4-iodo-2-methyl-phenylamino)-benzamide;
5-Bromo-N-cyclopropylmethoxy-3,4-difluoro-2-(2-fluoro-4-iodo-phenylamino)-benzamide;
N-Cyclopropylmethoxy-2-(4-iodo-2-methyl-phenylamino)-4-nitro-benzamide;
N-Cyclopropylmethoxy-3,4,5-trifluoro-2-(2-fluoro-4-iodo-phenylamino)-benzamide;
5-Chloro-N-cyclopropylmethoxy-3,4-difluoro-2-(2-fluoro-4-iodo-phenylamino)-benzamide;
5-Bromo-2-(2-chloro-4-iodo-phenylamino)-N-cyclopropylmethoxy-3,4-difluoro-benzamide;
N-Cyclopropylmethoxy-2-(2-fluoro-4-iodo-phenylamino)-4-nitro-benzamide;
2-(2-Chloro-4-iodo-phenylamino)-N-cyclopropylmethoxy-3,4,5-trifluoro-benzamide;
5-Chloro-2-(2-chloro-4-iodo-phenylamino)-N-cyclopropylmethoxy-3,4-difluoro-benzamide;
5-Bromo-2-(2-bromo-4-iodo-phenylamino)-N-ethoxy-3,4-difluoro-benzamide;
2-(2-Chloro-4-iodo-phenylamino)-N-ethoxy-4-nitro-benzamide;
2-(2-Bromo-4-iodo-phenylamino)-N-cyclopropylmethoxy-3,4,5-trifluoro-benzamide;
2-(2-Bromo-4-iodo-phenylamino)-5-chloro-N-cyclopropylmethoxy-3,4-difluoro-benzamide
2-(2-Bromo-4-iodo-phenylamino)-N-cyclopropylmethoxy-4-nitro-benzamide;
N-Cyclopropylmethoxy-4-fluoro-2-(2-fluoro-4-iodo-phenylamino)-benzamide;
N-Cyclopropylmethoxy-3,4-difluoro-2-(2-fluoro-4-iodo-phenylamino)-benzamide;
2-(2-Chloro-4-iodo-phenylamino)-N-cyclopropylmethoxy-4-fluoro-benzamide;
2-(2-Chloro-4-iodo-phenylamino)-N-cyclopropylmethoxy-3,4-difluoro-benzamide;
2-(2-Bromo-4-iodo-phenylamino)-N-cyclopropylmethoxy-4-fluoro-benzamide; or
2-(2-Bromo-4-iodo-phenylamino)-N-cyclopropylmethoxy-3,4-difluoro-benzamide.

In a further embodiment, the present invention provides a compound of formula

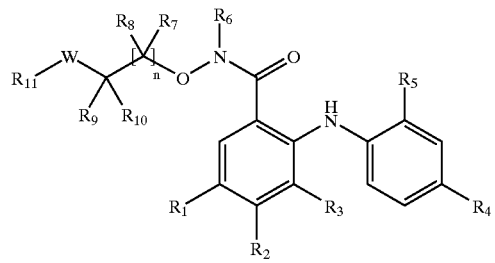

III wherein $R_1$ is hydrogen, halogen, or nitro;
$R_2$ is hydrogen or fluorine;
$R_3$ is hydrogen or fluorine;
$R_4$ is hydrogen, iodine, bromine, chlorine, or fluorine;
$R_5$ is hydrogen, halogen, hydroxy, $C_{1-8}$ alkyl, $C_{1-8}$ alkoxy, trifluoromethyl, or cyano;
n is 1 to 5;
$R_6$, $R_7$, $R_8$, $R_9$, and $R_{10}$ are independently hydrogen, $C_{1-8}$ alkyl, $C_{3-8}$ cycloalkyl, hydroxy, $C_{1-8}$ alkoxy, perhalo($C_{1-3}$)alkyl, hydroxy($C_{1-8}$)alkyl, $(C_{1-5})$alkoxy($C_{1-5}$) alkyl, $[(C_{1-4})alkyl]_2$aminomethyl, $(C_{2-7})$ heterocycle($C_{1-5}$) alkyl, or aryloxy($C_{1-5}$)alkyl, or may be independently joined to complete a 3–10 member cyclic ring optionally containing additional heteroatoms selected from the group consisting of O, S, NH, and N-alkyl, wherein $R_7$ and $R_8$ are independently selected for n>1;
Ra and Rb are independently hydrogen or $C_{1-4}$ alkyl;
W is O or NRa;
$R_{11}$ is hydrogen, $C_{1-8}$ alkyl, $C_{2-6}$ alkenyl, $C_{3-8}$ cycloalkyl, hydroxy($C_{1-8}$)alkyl, $(C_{1-5})$alkoxy($C_{1-5}$)alkyl, phenyl, $C_{2-7}$ heteroaryl, $(C_{1-8})$alkylcarbonyl, (phenyl)carbonyl, (phenyl)($C_{1-3}$ alkyl)carbonyl, or trifluoro($C_{1-6}$)alkyl;
wherein the above alkyl, alkoxy, cycloalkyl, heteroaryl, and phenyl groups can be optionally substituted with between 1 and 5 substituents independently selected from the group consisting of hydroxy, amino, monoalkylamino, dialkylamino, halogen, cyano, $(C_{1-3})$alkoxy, COOR, OCORa, CONRaRb, NRaCORb, SO, $SO_2$, $SO_4$, and $SO_2$NRaRb;

and pharmaceutically acceptable salts, $(C_{1-6})$ amides and $(C_{1-6})$ esters thereof.
Specific MEK inhibitors provided by the invention include:

5-Chloro-2-(2-chloro-4-iodo-phenylamino)-N-(2,3-dihydroxy-propoxy)-3,4-difluoro-benzamide;
3,4-Difluoro-2-(2-fluoro-4-iodo-phenylamino)-N-(2-hydroxy-ethoxy)-benzamide;
N-(2,3-Dihydroxy-propoxy)-3,4-difluoro-2-(2-fluoro-4-iodo-phenylamino)-benzamide;
5-Chloro-N-(2,3-dihydroxy-propoxy)-3,4-difluoro-2-(2-fluoro-4-iodo-phenylamino)-benzamide;
5-Chloro-N-((R)-2,3-dihydroxy-propoxy)-3,4-difluoro-2-(2-fluoro-4-iodo-phenylamino)-benzamide;
3,4-Difluoro-2-(2-fluoro-4-iodo-phenylamino)-N-(2-methylamino-ethoxy)-benzamide; hydrochloride;
N-((R)-2,3-Dihydroxy-propoxy)-3,4-difluoro-2-(2-fluoro-4-iodo-phenylamino)-benzamide;
N-((S)-2,3-Dihydroxy-propoxy)-3,4-difluoro-2-(2-fluoro-4-iodo-phenylamino)-benzamide;

5-Chloro-2-(2-chloro-4-iodo-phenylamino)-N-((S)-2,3-dihydroxy-propoxy)-3,4-difluoro-benzamide;
5-Chloro-2-(2-chloro-4-iodo-phenylamino)-N-((R)-2,3-dihydroxy-propoxy)-3,4-difluoro-benzamide;
5-Chloro-N-((S) 2,3-dihydroxy-propoxy)-3,4-difluoro-2-(2-fluoro-4-iodo-phenylamino)-benzamide;
3,4-Difluoro-2-(2-fluoro-4-iodo-phenylamino)-N-(2-hydroxy-1-hydroxymethyl-ethoxy)-benzamide; and
5-Chloro-3,4-difluoro-2-(2-fluoro-4-iodo-phenylamino)-N-(2-hydroxy-1-hydroxymethyl-ethoxy)-benzamide.

Additional MEK inhibitors provided by the invention include:

3,4,5-Trifluoro-N-(2-hydroxy-ethoxy)-2-(4-iodo-2-methyl-phenylamino)-benzamide;
3,4-Difluoro-N-(2-hydroxy-ethoxy)-2-(4-iodo-2-methyl-phenylamino)-benzamide;
2-(2-Chloro-4-iodo-phenylamino)-3,4-difluoro-N-(2-hydroxy-ethoxy)-benzamide;
2-(2-Chloro-4-iodo-phenylamino)-4-fluoro-N-(2-hydroxy-ethoxy)-benzamide;
4-Fluoro-N-(2-hydroxy-ethoxy)-2-(4-iodo-2-methyl-phenylamino)-benzamide;
2-(2-Chloro-4-iodo-phenylamino)-3,4,5-trifluoro-N-(2-hydroxy-ethoxy)-benzamide;
5-Chloro-3,4-difluoro-N-(2-hydroxy-ethoxy)-2-(4-iodo-phenylamino)-benzamide;
4-Fluoro-2-(2-fluoro-4-iodo-phenylamino)-N-(2-hydroxy-ethoxy)-benzamide;
3,4-Difluoro-2-(2-fluoro-4-iodo-phenylamino)-N-(2-hydroxy-ethoxy)-benzamide;
5-Chloro-3,4-difluoro-2-(2-fluoro-4-iodo-phenylamino)-N-(2-hydroxy-ethoxy)-benzamide;
5-Bromo-3,4-difluoro-2-(2-fluoro-4-iodo-phenylamino)-N-(2-hydroxy-ethoxy)-benzamide;
4,5-Difluoro-N-(2-hydroxy-ethoxy)-2-(4-iodo-2-methyl-phenylamino)-benzamide;
5-Bromo-3,4-difluoro-N-(2-hydroxy-ethoxy)-2-(4-iodo-2-methyl-phenylamino)-benzamide;
5-Bromo-2-(2-chloro-4-iodo-phenylamino)-3,4-difluoro-N-(2-hydroxy-ethoxy)-benzamide;
5-Chloro-3,4-difluoro-N-(2-hydroxy-ethoxy)-2-(4-iodo-2-methyl-phenylamino)-benzamide;
5-Bromo-4-fluoro-N-(2-hydroxy-ethoxy)-2-(4-iodo-2-methyl-phenylamino)-benzamide;
2-(2-Chloro-4-iodo-phenylamino)-4,5-difluoro-N-(2-hydroxy-ethoxy)-benzamide;
4,5-Difluoro-2-(2-fluoro-4-iodo-phenylamino)-N-(2-hydroxy-ethoxy)-benzamide;
5-Bromo-4-fluoro-2-(2-fluoro-4-iodo-phenylamino)-N-(2-hydroxy-ethoxy)-benzamide;
5-Chloro-2-(2-chloro-4-iodo-phenylamino)-3,4-difluoro-N-(2-hydroxy-ethoxy)-benzamide;
3,4,5-Trifluoro-2-(2-fluoro-4-iodo-phenylamino)-N-(2-hydroxy-ethoxy)-benzamide;
2-(4-Bromo-2-fluoro-phenylamino)-3,4-difluoro-N-(2-hydroxy-ethoxy)-benzamide;
2-(4-Bromo-2-fluoro-phenylamino)-4,5-difluoro-N-(2-hydroxy-ethoxy)-benzamide;
2-(4-Chloro-2-fluoro-phenylamino)-3,4-difluoro-N-(2-hydroxy-ethoxy)-benzamide;
3,4-Difluoro-2-(2-fluoro-phenylamino)-N-(2-hydroxy-ethoxy)-benzamide;
5-Chloro-2-(2,4-difluoro-phenylamino)-3,4-difluoro-N-(2-hydroxy-ethoxy)-benzamide;
2-(2,4-Difluoro-phenylamino)-3,4-difluoro-N-(2-hydroxy-ethoxy)-benzamide;
4-Fluoro-N-(3-hydroxy-propoxy)-2-(4-iodo-2-methyl-phenylamino)-benzamide;
5-Chloro-3,4-difluoro-N-(3-hydroxy-propoxy)-2-(4-iodo-2-methyl-phenylamino)-benzamide;
2-(2-Chloro-4-iodo-phenylamino)-4-fluoro-N-(3-hydroxy-propoxy)-benzamide;
5-Bromo-2-(2-chloro-4-iodo-phenylamino)-3,4-difluoro-N-(3-hydroxy-propoxy)-benzamide;
3,4-Difluoro-2-(2-fluoro-4-iodo-phenylamino)-N-(3-hydroxy-propoxy)-benzamide;
3,4-Difluoro-2-(2-fluoro-4-iodo-phenylamino)-N-(4-hydroxy-butoxy)-benzamide;
5-Chloro-2-(2-chloro-4-iodo-phenylamino)-N-(2,3-dihydroxy-propoxy)-3,4-difluoro-benzamide;
5-Chloro-N-(2,3-dihydroxy-propoxy)-3,4-difluoro-2-(4-iodo-2-methyl-phenylamino)-benzamide;
5-Chloro-N-(3,4-dihydroxy-butoxy)-3,4-difluoro-2-(4-iodo-2-methyl-phenylamino)-benzamide;
5-Chloro-2-(2-chloro-4-iodo-phenylamino)-N-(3,4-dihydroxy-butoxy)-3,4-difluoro-benzamide;
N-(2,2-Dimethyl-1,3-dioxolan-4-ylmethoxy)-3,4-difluoro-2-(2-fluoro-4-iodo-phenyl amino)-benzamide;
N-(2,3-Dihydroxy-propoxy)-3,4-difluoro-2-(2-fluoro-4-iodo-phenylamino)-benzamide;
5-Bromo-N-(2,3-dihydroxy-propoxy)-3,4-difluoro-2-(2-fluoro-4-iodo-phenylamino)-benzamide;
5-Chloro-N-(2,3-dihydroxy-propoxy)-3,4-difluoro-2-(2-fluoro-4-iodo-phenylamino)-benzamide;
N-(2,3-Dihydroxy-propoxy)-4-fluoro-2-(2-fluoro-4-iodo-phenylamino)-benzamide;
N-(2,3-Dihydroxy-propoxy)-3,4,5-trifluoro-2-(2-fluoro-4-iodo-phenylamino)-benzamide;
2-(4-Bromo-2-fluoro-phenylamino)-N-(2,3-dihydroxy-propoxy)-3,4-difluoro-benzamide;
2-(4-Chloro-2-fluoro-phenylamino)-N-(2,3-dihydroxy-propoxy)-3,4-difluoro-benzamide;
N-(2,2-Dimethyl-1,3-dioxinan-5-yloxy)-3,4-difluoro-2-(2-fluoro-4-iodo-phenylamino)-benzamide;
3,4-Difluoro-2-(2-fluoro-4-iodo-phenylamino)-N-(2-hydroxy-1-hydroxymethyl-ethoxy)-benzamide;
5-Chloro-3,4-difluoro-2-(2-fluoro-4-iodo-phenylamino)-N-(2-hydroxy-1-hydroxymethyl-ethoxy)-benzamide;
N-((R)-2,3-Dihydroxy-propoxy)-3,4-difluoro-2-(2-fluoro-4-iodo-phenylamino)-benzamide;
N-((S)-2,3-Dihydroxy-propoxy)-3,4-difluoro-2-(2-fluoro-4-iodo-phenylamino)-benzamide;
5-Chloro-2-(2-chloro-4-iodo-phenylamino)-N-((R)-2,3-dihydroxy-propoxy)-3,4-difluoro-benzamide;
5-Chloro-2-(2-chloro-4-iodo-phenylamino)-N-((S)-2,3-dihydroxy-propoxy)-3,4-difluoro-benzamide;
5-Chloro-N-((R)-2,3-dihydroxy-propoxy)-3,4-difluoro-2-(2-fluoro-4-iodo-phenylamino)-benzamide;
5-Chloro-N-((S) 2,3-dihydroxy-propoxy)-3,4-difluoro-2-(2-fluoro-4-iodo-phenylamino)-benzamide;
2-(4-Bromo-2-fluoro-phenylamino)-N-((R)-2,3-dihydroxy-propoxy)-3,4-difluoro-benzamide;
2-(2-Chloro-4-iodo-phenylamino)-3,4-difluoro-N-(2-vinyloxy-ethoxy)-benzamide;
2-(2-Chloro-4-iodo-phenylamino)-3,4,5-trifluoro-N-(2-vinyloxy-ethoxy)-benzamide;
4-Fluoro-2-(2-fluoro-4-iodo-phenylamino)-N-(2-vinyloxy-ethoxy)-benzamide;
3,4-Difluoro-2-(2-fluoro-4-iodo-phenylamino)-N-(2-vinyloxy-ethoxy)-benzamide;
5-Chloro-3,4-difluoro-2-(2-fluoro-4-iodo-phenylamino)-N-(2-vinyloxy-ethoxy)-benzamide;
5-Bromo-3,4-difluoro-2-(2-fluoro-4-iodo-phenylamino)-N-(2-vinyloxy-ethoxy)-benzamide;

5-Bromo-2-(2-chloro-4-iodo-phenylamino)-3,4-difluoro-N-(2-hydroxy-1,1-dimethyl-ethoxy)-benzamide;
3,4-Difluoro-N-(2-hydroxy-1,1-dimethyl-ethoxy)-2-(4-iodo-2-methyl-phenylamino)-benzamide;
2-(2-Chloro-4-iodo-phenylamino)-3,4-difluoro-N-(2-hydroxy-2-methyl-propoxy)-benzamide;
3,4-Difluoro-2-(2-fluoro-4-iodo-phenylamino)-N-(2-hydroxy-1,1-dimethyl-ethoxy)-benzamide;
5-Chloro-3,4-difluoro-2-(2-fluoro-4-iodo-phenylamino)-N-(2-hydroxy-1,1-dimethyl-ethoxy)-benzamide;
3,4-Difluoro-2-(2-fluoro-4-iodo-phenylamino)-N-(2-hydroxy-2-methyl-propoxy)-benzamide;
3,4-Difluoro-N-(2-hydroxy-3-methoxy-propoxy)-2-(4-iodo-2-methyl-phenylamino)-benzamide;
5-Bromo-2-(2-chloro-4-iodo-phenylamino)-3,4-difluoro-N-(2-hydroxy-3-methoxy-propoxy)-benzamide;
3,4-Difluoro-N-(1-hydroxymethyl-cyclopropylmethoxy)-2-(4-iodo-2-methyl-phenylamino)-benzamide;
5-Bromo-2-(2-chloro-4-iodo-phenylamino)-3,4-difluoro-N-(1-hydroxymethyl-cyclopropylmethoxy)-benzamide;
3,4-Difluoro-2-(4-iodo-2-methyl-phenylamino)-N-(3,3,3-trifluoro-2-hydroxy-propoxy)-benzamide;
5-Bromo-2-(2-chloro-4-iodo-phenylamino)-3,4-difluoro-N-(3,3,3-trifluoro-2-hydroxy-propoxy)-benzamide;
3,4-Difluoro-2-(2-fluoro-4-iodo-phenylamino)-N-(2-hydroxymethyl-cyclopropylmethoxy)-benzamide;
5-Chloro-3,4-difluoro-2-(2-fluoro-4-iodo-phenylamino)-N-(2-hydroxymethyl-cyclopropylmethoxy)-benzamide;
N-(2,3-Dihydroxy-3-methyl-butoxy)-3,4-difluoro-2-(2-fluoro-4-iodo-phenylamino)-benzamide;
2-(2-Chloro-4-iodo-phenylamino)-3,4-difluoro-N-(2-phenylamino-ethoxy)-benzamide;
3,4-Difluoro-2-(4-iodo-2-methyl-phenylamino)-N-(2-methylamino-ethoxy)-benzamide;
3,4-Difluoro-2-(2-fluoro-4-iodo-phenylamino)-N-(2-methylamino-ethoxy)-benzamide; hydrochloride;
3,4-Difluoro-2-(4-iodo-2-methyl-phenylamino)-N-[2-(2,2,2-trifluoro-ethylamino)-ethoxy]-benzamide; hydrochloride;
2-(2-Chloro-4-iodo-phenylamino)-4-fluoro-N-(2-hydroxy-ethoxy)-N-methyl-benzamide;
Acetic acid 2-[3,4,5-trifluoro-2-(4-iodo-2-methyl-phenylamino)-benzoylaminooxy]-ethyl ester;
[3,4-Difluoro-2-(2-fluoro-4-iodo-phenylamino)-phenyl]-(4-hydroxy-isoxazolidin-2-yl)-methanone;
5-Bromo-N-(2,3-dihydroxy-propoxy)-3,4-difluoro-2-(2-fluoro-phenylamino)-benzamide;
N-(2,3-Dihydroxy-propoxy)-3,4-difluoro-2-(2-fluoro-phenylamino)-benzamide;
2-(2-Chloro-4-iodo-phenylamino)-N-(2,3-dihydroxy-propoxy)-3,4-difluoro-benzamide;
2-(2-Chloro-4-iodo-phenylamino)-N-(2,3-dihydroxy-propoxy)-3,4,5-trifluoro-benzamide;
5-Bromo-2-(2-chloro-4-iodo-phenylamino)-N-(2,3-dihydroxy-propoxy)-3,4-difluoro-benzamide;
N-(2,3-Dihydroxy-propoxy)-3,4-difluoro-2-(4-iodo-2-methyl-phenylamino)-benzamide;
N-(2,3-Dihydroxy-propoxy)-3,4,5-trifluoro-2-(4-iodo-2-methyl-phenylamino)-benzamide;
5-Bromo-N-(2,3-dihydroxy-propoxy)-3,4-difluoro-2-(4-iodo-2-methyl-phenylamino)-benzamide;
2-(2-Chloro-4-iodo-phenylamino)-N-(3,4-dihydroxy-butoxy)-3,4-difluoro-benzamide;
2-(2-Chloro-4-iodo-phenylamino)-N-(3,4-dihydroxy-butoxy)-3,4,5-trifluoro-benzamide;
5-Bromo-2-(2-chloro-4-iodo-phenylamino)-N-(3,4-dihydroxy-butoxy)-3,4-difluoro-benzamide;
N-(3,4-Dihydroxy-butoxy)-3,4-difluoro-2-(4-iodo-2-methyl-phenylamino)-benzamide;
N-(3,4-Dihydroxy-butoxy)-3,4,5-trifluoro-2-(4-iodo-2-methyl-phenylamino)-benzamide;
5-Bromo-N-(3,4-dihydroxy-butoxy)-3,4-difluoro-2-(4-iodo-2-methyl-phenylamino)-benzamide;
5-Bromo-2-(2-chloro-4-iodo-phenylamino)-3,4-difluoro-N-(3-hydroxy-propoxy)-benzamide;
2-(2-Chloro-4-iodo-phenylamino)-3,4-difluoro-N-(3-hydroxy-propoxy)-benzamide;
3,4,5-Trifluoro-N-(3-hydroxy-propoxy)-2-(4-iodo-2-methyl-phenylamino)-benzamide;
2-(2-Chloro-4-iodo-phenylamino)-3,4,5-trifluoro-N-(3-hydroxy-propoxy)-benzamide;
5-Bromo-3,4-difluoro-N-(3-hydroxy-propoxy)-2-(4-iodo-2-methyl-phenylamino)-benzamide;
3,4-Difluoro-N-(3-hydroxy-propoxy)-2-(4-iodo-2-methyl-phenylamino)-benzamide;
2-(2-Chloro-4-iodo-phenylamino)-3,4-difluoro-N-(2-hydroxy-butoxy)-benzamide;
2-(2-Chloro-4-iodo-phenylamino)-3,4,5-trifluoro-N-(2-hydroxy-butoxy)-benzamide;
3,4,5-Trifluoro-N-(2-hydroxy-butoxy)-2-(4-iodo-2-methyl-phenylamino)-benzamide;
5-Bromo-2-(2-chloro-4-iodo-phenylamino)-3,4-difluoro-N-(2-hydroxy-butoxy)-benzamide;
5-Bromo-3,4-difluoro-N-(2-hydroxy-butoxy)-2-(4-iodo-2-methyl-phenylamino)-benzamide;
3,4-Difluoro-N-(2-hydroxy-butoxy)-2-(4-iodo-2-methyl-phenylamino)-benzamide;
5-Chloro-2-(2-chloro-4-iodo-phenylamino)-3,4-difluoro-N-(2-hydroxy-butoxy)-benzamide;
5-Chloro-3,4-difluoro-N-(2-hydroxy-butoxy)-2-(4-iodo-2-methyl-phenylamino)-benzamide;
3,4-Difluoro-2-(2-fluoro-4-iodo-phenylamino)-N-(2-hydroxy-butoxy)-benzamide;
5-Bromo-3,4-difluoro-2-(2-fluoro-4-iodo-phenylamino)-N-(2-hydroxy-butoxy)-benzamide;
5-Chloro-3,4-difluoro-2-(2-fluoro-4-iodo-phenylamino)-N-(2-hydroxy-butoxy)-benzamide;
4,5-Difluoro-2-(2-fluoro-4-iodo-phenylamino)-N-(2-hydroxy-butoxy)-benzamide;
5-Chloro-2-(2,4-difluoro-phenylamino)-3,4-difluoro-N-(2-hydroxy-butoxy)-benzamide;
2-(2,4-Difluoro-phenylamino)-3,4-difluoro-N-(2-hydroxy-butoxy)-benzamide;
2-(4-Bromo-2-fluoro-phenylamino)-3,4-difluoro-N-(2-hydroxy-butoxy)-benzamide;
5-Chloro-3,4-difluoro-N-(2-hydroxy-1-methyl-ethoxy)-2-(4-iodo-2-methyl-phenylamino)-benzamide;
2-(2-Chloro-4-iodo-phenylamino)-3,4-difluoro-N-(2-hydroxy-1-methyl-ethoxy)-benzamide;
2-(2-Chloro-4-iodo-phenylamino)-3,4,5-trifluoro-N-(2-hydroxy-1-methyl-ethoxy)-benzamide;
3,4,5-Trifluoro-N-(2-hydroxy-1-methyl-ethoxy)-2-(4-iodo-2-methyl-phenylamino)-benzamide;
5-Bromo-2-(2-chloro-4-iodo-phenylamino)-3,4-difluoro-N-(2-hydroxy-1-methyl-ethoxy)-benzamide;
5-Bromo-3,4-difluoro-N-(2-hydroxy-1-methyl-ethoxy)-2-(4-iodo-2-methyl-phenylamino)-benzamide;
2-(4-Chloro-2-fluoro-phenylamino)-3,4-difluoro-N-(2-hydroxy-1-methyl-ethoxy)-benzamide;
3,4-Difluoro-N-(2-hydroxy-1-methyl-ethoxy)-2-(4-iodo-2-methyl-phenylamino)-benzamide;
5-Chloro-2-(2-chloro-4-iodo-phenylamino)-3,4-difluoro-N-(2-hydroxy-1-methyl-ethoxy)-benzamide;
3,4-Difluoro-2-(2-fluoro-4-iodo-phenylamino)-N-(2-hydroxy-1-methyl-ethoxy)-benzamide;

5-Bromo-3,4-difluoro-2-(2-fluoro-4-iodo-phenylamino)-N-(2-hydroxy-1-methyl-ethoxy)-benzamide;
5-Chloro-3,4-difluoro-2-(2-fluoro-4-iodo-phenylamino)-N-(2-hydroxy-1-methyl-ethoxy)-benzamide;
4,5-Difluoro-2-(2-fluoro-4-iodo-phenylamino)-N-(2-hydroxy-1-methyl-ethoxy)-benzamide;
5-Chloro-2-(2,4-difluoro-phenylamino)-3,4-difluoro-N-(2-hydroxy-1-methyl-ethoxy)-benzamide;
2-(2,4-Difluoro-phenylamino)-3,4-difluoro-N-(2-hydroxy-1-methyl-ethoxy)-benzamide;
2-(2-Chloro-4-iodo-phenylamino)-3,4-difluoro-N-(2-methoxy-ethoxy)-benzamide;
2-(2-Chloro-4-iodo-phenylamino)-3,4,5-trifluoro-N-(2-methoxy-ethoxy)-benzamide;
3,4-Difluoro-2-(4-iodo-2-methyl-phenylamino)-N-(2-methoxy-ethoxy)-benzamide;
5-Bromo-3,4-difluoro-2-(4-iodo-2-methyl-phenylamino)-N-(2-methoxy-ethoxy)-benzamide;
3,4,5-Trifluoro-2-(4-iodo-2-methyl-phenylamino)-N-(2-methoxy-ethoxy)-benzamide;
5-Bromo-2-(2-chloro-4-iodo-phenylamino)-3,4-difluoro-N-(2-methoxy-ethoxy)-benzamide;
5-Chloro-2-(2-chloro-4-iodo-phenylamino)-3,4-difluoro-N-(2-methoxy-ethoxy)-benzamide;
5-Chloro-3,4-difluoro-2-(4-iodo-2-methyl-phenylamino)-N-(2-methoxy-ethoxy)-benzamide;
5-Chloro-3,4-difluoro-2-(2-fluoro-4-iodo-phenylamino)-N-(2-methoxy-ethoxy)-benzamide;
2-(2-Chloro-4-iodo-phenylamino)-3,4-difluoro-N-(2-hydroxy-3-morpholin-4-yl-propoxy)-benzamide;
5-Bromo-2-(2-chloro-4-iodo-phenylamino)-3,4-difluoro-N-(2-hydroxy-3-morpholin-4-yl-propoxy)-benzamide;
2-(2-Chloro-4-iodo-phenylamino)-3,4,5-trifluoro-N-(2-hydroxy-3-morpholin-4-yl-propoxy)-benzamide;
3,4,5-Trifluoro-N-(2-hydroxy-3-morpholin-4-yl-propoxy)-2-(4-iodo-2-methyl-phenylamino)-benzamide;
5-Bromo-3,4-difluoro-N-(2-hydroxy-3-morpholin-4-yl-propoxy)-2-(4-iodo-2-methyl-phenylamino)-benzamide;
3,4-Difluoro-N-(2-hydroxy-3-morpholin-4-yl-propoxy)-2-(4-iodo-2-methyl-phenylamino)-benzamide;
5-Chloro-2-(2-chloro-4-iodo-phenylamino)-3,4-difluoro-N-(2-hydroxy-3-morpholin-4-yl-propoxy)-benzamide;
5-Chloro-3,4-difluoro-N-(2-hydroxy-3-morpholin-4-yl-propoxy)-2-(4-iodo-2-methyl-phenylamino)-benzamide;
3,4-Difluoro-2-(2-fluoro-4-iodo-phenylamino)-N-(2-hydroxy-3-morpholin-4-yl-propoxy)-benzamide;
5-Chloro-3,4-difluoro-2-(2-fluoro-4-iodo-phenylamino)-N-(2-hydroxy-3-morpholin-4-yl-propoxy)-benzamide;
4,5-Difluoro-2-(2-fluoro-4-iodo-phenylamino)-N-(2-hydroxy-3-morpholin-4-yl-propoxy)-benzamide;
5-Chloro-2-(2,4-difluoro-phenylamino)-3,4-difluoro-N-(2-hydroxy-3-morpholin-4-yl-propoxy)-benzamide;
2-(4-Chloro-2-fluoro-phenylamino)-3,4-difluoro-N-(2-hydroxy-3-morpholin-4-yl-propoxy)-benzamide;
2-(2-Chloro-4-iodo-phenylamino)-3,4-difluoro-N-(2-hydroxy-propoxy)-benzamide;
3,4,5-Trifluoro-N-(2-hydroxy-propoxy)-2-(4-iodo-2-methyl-phenylamino)-benzamide;
5-Bromo-2-(2-chloro-4-iodo-phenylamino)-3,4-difluoro-N-(2-hydroxy-propoxy)-benzamide;
5-Bromo-3,4-difluoro-N-(2-hydroxy-propoxy)-2-(4-iodo-2-methyl-phenylamino)-benzamide;
2-(2-Chloro-4-iodo-phenylamino)-3,4,5-trifluoro-N-(2-hydroxy-propoxy)-benzamide;
5-Chloro-2-(2-chloro-4-iodo-phenylamino)-3,4-difluoro-N-(2-hydroxy-propoxy)-benzamide;
3,4-Difluoro-N-(2-hydroxy-propoxy)-2-(4-iodo-2-methyl-phenylamino)-benzamide;
5-Chloro-3,4-difluoro-N-(2-hydroxy-propoxy)-2-(4-iodo-2-methyl-phenylamino)-benzamide;
3,4-Difluoro-2-(2-fluoro-4-iodo-phenylamino)-N-(2-hydroxy-propoxy)-benzamide;
5-Chloro-3,4-difluoro-2-(2-fluoro-4-iodo-phenylamino)-N-(2-hydroxy-propoxy)-benzamide;
5-Chloro-2-(2,4-difluoro-phenylamino)-3,4-difluoro-N-(2-hydroxy-propoxy)-benzamide;
2-(2,4-Difluoro-phenylamino)-3,4-difluoro-N-(2-hydroxy-propoxy)-benzamide;
2-(4-Chloro-2-fluoro-phenylamino)-3,4-difluoro-N-(2-hydroxy-propoxy)-benzamide;
4,5-Difluoro-2-(2-fluoro-4-iodo-phenylamino)-N-(2-hydroxy-propoxy)-benzamide;
2-(2-Chloro-4-iodo-phenylamino)-3,4,5-trifluoro-N-(2-hydroxy-2-methyl-propoxy)-benzamide;
3,4,5-Trifluoro-N-(2-hydroxy-2-methyl-propoxy)-2-(4-iodo-2-methyl-phenylamino)-benzamide;
5-Bromo-3,4-difluoro-N-(2-hydroxy-2-methyl-propoxy)-2-(4-iodo-2-methyl-phenylamino)-benzamide;
5-Bromo-2-(2-chloro-4-iodo-phenylamino)-3,4-difluoro-N-(2-hydroxy-2-methyl-propoxy)-benzamide;
3,4-Difluoro-N-(2-hydroxy-2-methyl-propoxy)-2-(4-iodo-2-methyl-phenylamino)-benzamide;
5-Chloro-2-(2-chloro-4-iodo-phenylamino)-3,4-difluoro-N-(2-hydroxy-2-methyl-propoxy)-benzamide;
5-Chloro-3,4-difluoro-N-(2-hydroxy-2-methyl-propoxy)-2-(4-iodo-2-methyl-phenylamino)-benzamide;
3,4-Difluoro-2-(2-fluoro-4-iodo-phenylamino)-N-(2-hydroxy-2-methyl-propoxy)-benzamide;
5-Bromo-3,4-difluoro-2-(2-fluoro-4-iodo-phenylamino)-N-(2-hydroxy-2-methyl-propoxy)-benzamide;
5-Chloro-3,4-difluoro-2-(2-fluoro-4-iodo-phenylamino)-N-(2-hydroxy-2-methyl-propoxy)-benzamide;
5-Chloro-2-(2,4-difluoro-phenylamino)-3,4-difluoro-N-(2-hydroxy-2-methyl-propoxy)-benzamide;
2-(2,4-Difluoro-phenylamino)-3,4-difluoro-N-(2-hydroxy-2-methyl-propoxy)-benzamide;
2-(4-Bromo-2-fluoro-phenylamino)-3,4-difluoro-N-(2-hydroxy-2-methyl-propoxy)-benzamide;
2-(2-Chloro-4-iodo-phenylamino)-3,4-difluoro-N-(2-hydroxy-3-phenoxy-propoxy)-benzamide;
2-(2-Chloro-4-iodo-phenylamino)-3,4,5-trifluoro-N-(2-hydroxy-3-phenoxy-propoxy)-benzamide;
3,4,5-Trifluoro-N-(2-hydroxy-3-phenoxy-propoxy)-2-(4-iodo-2-methyl-phenylamino)-benzamide;
5-Bromo-2-(2-chloro-4-iodo-phenylamino)-3,4-difluoro-N-(2-hydroxy-3-phenoxy-propoxy)-benzamide;
5-Bromo-3,4-difluoro-N-(2-hydroxy-3-phenoxy-propoxy)-2-(4-iodo-2-methyl-phenylamino)-benzamide;
3,4-Difluoro-N-(2-hydroxy-3-phenoxy-propoxy)-2-(4-iodo-2-methyl-phenylamino)-benzamide;
5-Chloro-2-(2-chloro-4-iodo-phenylamino)-3,4-difluoro-N-(2-hydroxy-3-phenoxy-propoxy)-benzamide;
5-Chloro-3,4-difluoro-N-(2-hydroxy-3-phenoxy-propoxy)-2-(4-iodo-2-methyl-phenylamino)-benzamide;
3,4-Difluoro-2-(2-fluoro-4-iodo-phenylamino)-N-(2-hydroxy-3-phenoxy-propoxy)-benzamide;
5-Chloro-3,4-difluoro-2-(2-fluoro-4-iodo-phenylamino)-N-(2-hydroxy-3-phenoxy-propoxy)-benzamide;
4,5-Difluoro-2-(2-fluoro-4-iodo-phenylamino)-N-(2-hydroxy-3-phenoxy-propoxy)-benzamide;
5-Chloro-2-(2,4-difluoro-phenylamino)-3,4-difluoro-N-(2-hydroxy-3-phenoxy-propoxy)-benzamide;
2-(2,4-Difluoro-phenylamino)-3,4-difluoro-N-(2-hydroxy-3-phenoxy-propoxy)-benzamide;
2-(4-Chloro-2-fluoro-phenylamino)-3,4-difluoro-N-(2-hydroxy-3-phenoxy-propoxy)-benzamide;

3,4-Difluoro-N-(3-hydroxy-2,2-dimethyl-propoxy)-2-(4-iodo-2-methyl-phenylamino)-benzamide;
2-(2-Chloro-4-iodo-phenylamino)-3,4,5-trifluoro-N-(3-hydroxy-2,2-dimethyl-propoxy)-benzamide;
3,4,5-Trifluoro-N-(3-hydroxy-2,2-dimethyl-propoxy)-2-(4-iodo-2-methyl-phenylamino)-benzamide;
5-Chloro-2-(2-chloro-4-iodo-phenylamino)-3,4-difluoro-N-(3-hydroxy-2,2-dimethyl-propoxy)-benzamide;
5-Chloro-3,4-difluoro-N-(3-hydroxy-2,2-dimethyl-propoxy)-2-(4-iodo-2-methyl-phenylamino)-benzamide;
3,4-Difluoro-2-(2-fluoro-4-iodo-phenylamino)-N-(3-hydroxy-2,2-dimethyl-propoxy)-benzamide;
5-Chloro-2-(2,4-difluoro-phenylamino)-3,4-difluoro-N-(3-hydroxy-2,2-dimethyl-propoxy)-benzamide;
3,4-Difluoro-2-(4-iodo-2-methyl-phenylamino)-N-[2-(2-methoxy-ethoxy)-ethoxy]-benzamide;
3,4,5-Trifluoro-2-(4-iodo-2-methyl-phenylamino)-N-[2-(2-methoxy-ethoxy)-ethoxy]-benzamide;
5-Bromo-3,4-difluoro-2-(4-iodo-2-methyl-phenylamino)-N-[2-(2-methoxy-ethoxy)-ethoxy]-benzamide;
2-(2-Chloro-4-iodo-phenylamino)-3,4-difluoro-N-[2-(2-methoxy-ethoxy)-ethoxy]-benzamide;
2-(2-Chloro-4-iodo-phenylamino)-3,4,5-trifluoro-N-[2-(2-methoxy-ethoxy)-ethoxy]-benzamide;
5-Bromo-2-(2-chloro-4-iodo-phenylamino)-3,4-difluoro-N-[2-(2-methoxy-ethoxy)-ethoxy]-benzamide;
3,4,5-Trifluoro-2-(2-fluoro-4-iodo-phenylamino)-N-(3,3,3-trifluoro-2-hydroxy-propoxy)-benzamide;
5-Chloro-2-(2,4-difluoro-phenylamino)-3,4-difluoro-N-(3,3,3-trifluoro-2-hydroxy-propoxy)-benzamide;
2-(2,4-Difluoro-phenylamino)-3,4-difluoro-N-(3,3,3-trifluoro-2-hydroxy-propoxy)-benzamide;
2-(4-Chloro-2-fluoro-phenylamino)-3,4-difluoro-N-(3,3,3-trifluoro-2-hydroxy-propoxy)-benzamide;
5-Chloro-2-(2,4-difluoro-phenylamino)-3,4-difluoro-N-(2-hydroxymethyl-cyclopropylmethoxy)-benzamide;
2-(2,4-Difluoro-phenylamino)-3,4-difluoro-N-(2-hydroxymethyl-cyclopropylmethoxy)-benzamide;
2-(4-Chloro-2-fluoro-phenylamino)-3,4-difluoro-N-(2-hydroxymethyl-cyclopropylmethoxy)-benzamide;
4,5-Difluoro-2-(2-fluoro-4-iodo-phenylamino)-N-(2-hydroxymethyl-cyclopropylmethoxy)-benzamide;
3,4-Difluoro-2-(2-fluoro-4-iodo-phenylamino)-N-(1-hydroxymethyl-cyclopropylmethoxy)-benzamide;
3,4,5-Trifluoro-2-(2-fluoro-4-iodo-phenylamino)-N-(1-hydroxymethyl-cyclopropylmethoxy)-benzamide;
5-Bromo-3,4-difluoro-2-(2-fluoro-4-iodo-phenylamino)-N-(1-hydroxymethyl-cyclopropylmethoxy)-benzamide;
4,5-Difluoro-2-(2-fluoro-4-iodo-phenylamino)-N-(1-hydroxymethyl-cyclopropylmethoxy)-benzamide;
2-(2,4-Difluoro-phenylamino)-3,4-difluoro-N-(1-hydroxymethyl-cyclopropylmethoxy)-benzamide;
2-(4-Bromo-2-fluoro-phenylamino)-3,4-difluoro-N-(1-hydroxymethyl-cyclopropylmethoxy)-benzamide;
2-(4-Chloro-2-fluoro-phenylamino)-3,4-difluoro-N-(1-hydroxymethyl-cyclopropylmethoxy)-benzamide;
5-Chloro-2-(2,4-difluoro-phenylamino)-3,4-difluoro-N-(1-hydroxymethyl-cyclopropylmethoxy)-benzamide;
2-(2,4-Difluoro-phenylamino)-3,4-difluoro-N-(2-hydroxy-3-methoxy-propoxy)-benzamide;
5-Chloro-2-(2,4-difluoro-phenylamino)-3,4-difluoro-N-(2-hydroxy-3-methoxy-propoxy)-benzamide;
2-(4-Bromo-2-fluoro-phenylamino)-3,4-difluoro-N-(2-hydroxy-3-methoxy-propoxy)-benzamide;
2-(4-Chloro-2-fluoro-phenylamino)-3,4-difluoro-N-(2-hydroxy-3-methoxy-propoxy)-benzamide;
3,4,5-Trifluoro-2-(4-iodo-2-methyl-phenylamino)-N-(2-phenylamino-ethoxy)-benzamide;
5-Bromo-3,4-difluoro-2-(4-iodo-2-methyl-phenylamino)-N-(2-phenylamino-ethoxy)-benzamide;
2-(2-Chloro-4-iodo-phenylamino)-3,4-difluoro-N-(2-phenylamino-ethoxy)-benzamide;
2-(2-Chloro-4-iodo-phenylamino)-3,4,5-trifluoro-N-(2-phenylamino-ethoxy)-benzamide;
3,4-Difluoro-2-(4-iodo-2-methyl-phenylamino)-N-(2-phenylamino-ethoxy)-benzamide;
5-Bromo-2-(2-chloro-4-iodo-phenylamino)-3,4-difluoro-N-(2-phenylamino-ethoxy)-benzamide;
3,4-Difluoro-2-(2-fluoro-4-iodo-phenylamino)-N-((S)-3-hydroxy-2-methylamino-propoxy)-benzamide;
3,4-Difluoro-2-(2-fluoro-4-iodo-phenylamino)-N-((R)-3-hydroxy-2-methylamino-propoxy)-benzamide;
(S)-5-Chloro-3,4-Difluoro-2-(2-fluoro-4-iodo-phenylamino)-N-(3-hydroxy-2-methylamino-propoxy)-benzamide;
(R)-5-Chloro-3,4-Difluoro-2-(2-fluoro-4-iodo-phenylamino)-N-(3-hydroxy-2-methylamino-propoxy)-benzamide;
(S)-5-Chloro-2-(2-chloro-4-iodo-phenylamino)-3,4-difluoro-N-(3-hydroxy-2-methylamino-propoxy)-benzamide;
(R)-5-Chloro-2-(2-chloro-4-iodo-phenylamino)-3,4-difluoro-N-(3-hydroxy-2-methylamino-propoxy)-benzamide; and
3,4-Difluoro-2-(2-fluoro-4-iodo-phenylamino)-N-(2-hydroxy-3-methylamino-propoxy)-benzamide.

The migrated cells were quantitated as described, and the percent inhibition was represented.

FIG. 4 shows 2-(2-chloro-4-iodo-phenylamino)-N-cyclopropylmethoxy-3,4-difluoro-benzamide (Compound A) blocks IL-8 mediated neutrophil chemotaxis, in vitro. In trans-well migration chambers, neutrophils were pre-incubated with single concentration (1 $\mu$M) of 2-(2-chloro-4-iodo-phenylamino)-N-cyclopropylmethoxy-3,4-difluoro-benzamide and stimulated with varying concentrations of IL-8. Number of cells migrated was measured 3 hours after IL-8 stimulation and expressed as percent control. Each value represents the average ±S.E. obtained from at least three different donors with duplicates in each set.

Figure 5:
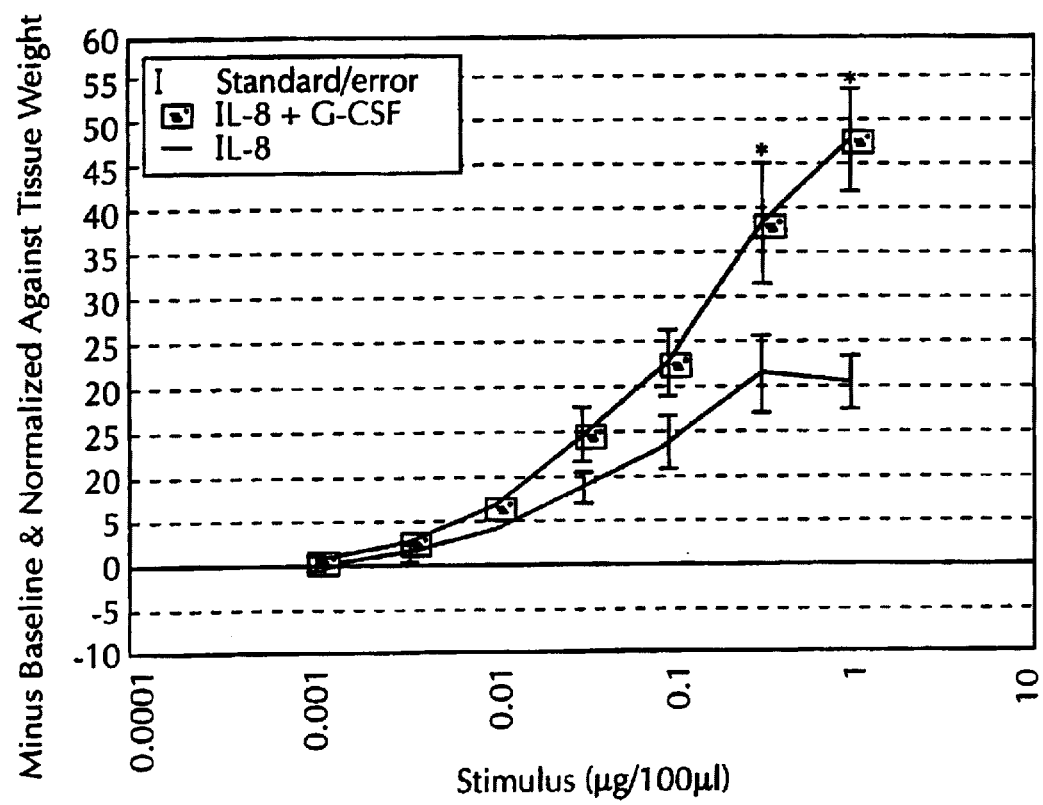

FIG. 5 shows that 2-(2-chloro-4-iodo-phenylamino)-N-cyclopropylmethoxy-3,4-difluoro-benzamide (Compound A) blocks neutrophil chemotaxis in vivo. Rabbits were dosed with 30 mg/kg 2-(2-chloro-4-iodo-phenylamino)-N-cyclopropylmethoxy-3,4-difluoro-benzamide three times at approximately 8-hour intervals. Three hours after the last dose, animals were injected with $^{125}$I IL-8 (10$\mu$Ci), and 10 minutes later various doses of cold (unlabeled) IL-8 was injected intradermally at local sites on the back of the rabbits. Sixty minutes later, the animals were sacrificed, punch biopsies were performed, and the radiation in the skin was measured using a gamma counter. Each value represents the average±standard deviation error of three representative experiments with three animals in each group and triplicates within each treatment. The asterisk indicates significant ($p<0.05$) differences between the respective treatments in control animals versus drug-administered animals.

DETAILED DESCRIPTION OF THE INVENTION

The present invention provides a method of treating, preventing, and/or inhibiting neutrophil migration or chemotaxis, the method comprises administering to a patient having a disease or condition including or characterized by neutrophil migration or chemotaxis, or at risk of having neutrophil migration or chemotaxis, a therapeutically effective amount of a compound that is a MEK inhibitor. Specifically, the present invention provides a method for inhibiting neutrophil migration in a patient in need of neutrophil migration inhibition, sail d method comprising administering to the patient a therapeutically effective amount of a compound that is an MEK inhibitor.

The patients of the present invention have a disease or a condition including neutrophil migration/chemotaxis as a symptom thereof, or are at risk of having a disease or a condition including neutrophil migration/chemotaxis as a symptom. Those skilled in the art are readily able to identify patients having a disease or condition including neutrophil migration/chemotaxis as a symptom. Moreover, patients who are at risk of having a disease or a condition characterized in part or as whole by neutrophil migration/chemotaxis are also easily identifiable by those skilled in the art. For example, patients who are at risk of having such a disease or condition generally comprise patients who have an ischemia reperfusion injury, chronic obstructive pulmonary disease, acute respiratory disease syndrome, cystic fibrosis, idiopathic pulmonary fibrosis, sepsis, endotoxemia, emphysema, or asbestosis. As such the present invention provides a method for treating a neutrophil mediated disease or condition comprising administering to a patient a therapeutically effective amount of a compound that is an MEK inhibitor. The term "patient" means all animals including humans. Examples of patients include humans, cows, dogs, cats, goats, sheep, and pigs.

The term "migration" means the pooling, aggregation, localization, chemotaxis, or other movement of neutrophils as a result of a disease or condition.

The compounds of the present invention, which can be used to inhibit neutrophil migration/chemotaxis, are MEK inhibitors. A MEK inhibitor is a compound that shows MEK inhibition when tested in the assays titled, "Enzyme Assays" in U.S. Pat. No. 5,525,625, column 6, beginning at line 35. The complete disclosure of U.S. Pat. No. 5,525,625 is hereby incorporated by reference. Examples of MEK inhibitors are 2-(2-amino-3-methoxyphenyl)-4-oxo-4H-[1] benzopyran and 2-(2-chloro-4-iodo-phenylamino)-N-cyclopropylmethoxy-3,4-difluoro-benzamide. Specifically, a compound is an MEK inhibitor if a compound shows activity in the assay titled, "Cascade Assay for Inhibitors of the MAP Kinase Pathway," column 6, line 36 to column 7, line 4 of the U.S. Pat. No. 5,525,625 and/or shows activity in the assay titled, "In Vitro MEK Assay" at column 7, lines 4 to 27 of the above-referenced patent. Alternatively, MEK inhibition can be measured in the assay described in Example 5 below. This assay is also disclosed in WO 02/06213 A1, the complete disclosure of which is hereby incorporated by reference.

A PI3K inhibitory compound, which can be used to inhibit neutrophil migration/chemotaxis in combination with the MEK inhibitory compound, is a compound that shows PI3K inhibition when tested as described below. Examples of PI3K inhibitors are Wortmannin (Calbiochem, La Jolla, Calif.; Cat. No. 681675), benzo[b]thiophene-2-carboxamide, 5,6-dimethoxy-3-phenoxy-N-1H-tetrazol-5-yl-. Specifically, any compound is a PI3K inhibitor if it is able to block the catalytic activity of PI3K. Other PI3K inhibitors known in the art can also be utilized in the present invention.

The MEK and PI3K inhibitors of the present method can be administered to a patient as part of a pharmaceutically acceptable composition. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray. The administration of a mitotic inhibitor may be before, during, or after the administration of the PI3K inhibitor. Simultaneous administration may be by the same (both actives by either local or systemic injection) or different routes (e.g., oral administration of a MEK inhibitor and intravenous administration of the mitotic inhibitor). While the MEK inhibitors can be formulated with the PI3K inhibitors, for instance in solution for intravenous injection or infusion, the active agents will more typically be formulated individually in their normal preparations, and will be administered individually, but generally at about the same time, or together in a course of treatment. Alternatively, the agents can be formulated together in a single formulation, in which case the PI3K inhibitor will be present at concentrations ranging from about 1 to about 1000 parts by weight relative to the MEK inhibitor, and the MEK inhibitor will be present at concentrations of about 1000 to about 1 part by weight relative to the PI3K inhibitor. Generally, the agents will be administered at about equal doses, or as otherwise approved by health regulatory agencies. The invention also encompasses the use of additional pharmaceutical agents, such as a second MEK inhibitor, a second PI3K inhibitor, as well as adjuvants, enhancers, or other pharmaceutically active and pharmaceutically acceptable materials. In one aspect, the amounts of each active may vary independently from each other over time. For example, a patient may receive a first MEK inhibitor with a PI3K inhibitor for a period of time, and then the first MEK inhibitor may be replaced by a second MEK inhibitor.

The invention also features compositions, packaged units, and kits which include at least one MEK inhibitor and at least one PI3K inhibitor. For example, the invention encompasses: (a) a single formulation (whether tablet, solution, or suspension, for example) that includes both a PI3K inhibitor and a MEK inhibitor; (b) a blister pack containing separate formulations of each active, such as a tablet or capsule form of a MEK inhibitor and a capsule or ampoule of a solution of a PI3K inhibitor; and (c) a kit with separate formulations of each active packaged together in a box with instructions for combination administration.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate, and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate, or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar—agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalamic formulations, eye ointments, powders, and solutions are also contemplated as being within the scope of this invention.

The compounds of the present method can be administered to a patient at dosage levels in the range of about 0.1 mg/day to about 1000 mg/day. For a normal human adult having a body weight of about 70 kg, a dosage in the range of about 0.01 mg/kg to about 100 mg/kg of body weight per day is preferable. The specific dosage used, however, can vary. For example, in determining the therapeutically effective amount of a compound, a number of factors are to be considered As such, the dosage can depend on the requirements of the patient, the severity of the condition being treated, and the pharmacological activity of the compound ro compounds being used. The determination of optimum dosages for a particular patient is well-known to those skilled in the art.

The compounds of the present method can be administered as pharmaceutically acceptable salts, esters, amides, or prodrugs. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19, which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present method can exist in unsolvated as well as solvated forms with pharmaceutically acceptable solvents such as water, ethanol, and the like. In general, the solvated forms are considered equivalent to the unsolvated forms for the purposes of the present invention.

The compounds of the present method can exist in different stereoisometric forms by virtue of the presence of asymmetric centers in the compounds. It is contemplated that all stereoisometric forms of the compounds as well as mixtures thereof, including racemic mixtures, form part of this invention.

The terms "halogen" or "halo" in the present invention refer to a fluorine, bromine, chlorine, and iodine atom or fluoro, bromo, chloro, and iodo. The terms fluorine and fluoro, for example, are understood to be equivalent herein.

As used herein, the term "aryl" means a cyclic, bicyclic, or tricyclic aromatic ring moiety having from five to twelve carbon atoms. Examples of typical aryl groups include phenyl, naphthyl, and fluorenyl. The aryl may be substituted by one, two, or three groups selected from fluoro, chloro, bromo, iodo, alkyl, hydroxy, alkoxy, nitro, amino, alkylamino, or dialkylamino. Typical substituted aryl groups include 3-fluorophenyl, 3,5-dimethoxyphenyl, 4-nitronaphthyl, 2-methyl-4-chloro-7-aminofluorenyl, and the like.

The term "aryloxy" means an aryl group bonded through an oxygen atom, for example phenoxy, 3-bromophenoxy, naphthyloxy, and 4-methyl-1-fluorenyloxy.

"Heteroaryl" means a cyclic, bicyclic, or tricyclic aromatic ring moiety having from 4 to 11 carbon atoms and one, two, or three heteroatoms selected from O, S, or N. Examples include furyl, thienyl, pyrrolyl, pyrazolyl, imidazolyl, triazolyl, thiazolyl, oxazolyl, xanthenyl, pyronyl, indolyl, pyrimidyl, naphthyridyl, pyridyl, benzinnidazolyl, and triazinyl. The heteroaryl groups can be unsubstituted or substituted by one, two, or three groups selected from fluoro, chloro, bromo, iodo, alkyl, hydroxy, alkoxy, nitro, amino, alkylamino, or dialkylamino. Examples of substituted heteroaryl groups include chloropyranyl, methylthienyl, fluoropyridyl, amino-1,4-benzisoxazinyl, nitroisoquinolinyl, and hydroxyindolyl.

The heteroaryl groups can be bonded through oxygen to make heteroaryloxy groups, for example thienyloxy, isothiazolyloxy, benzofuranyloxy, pyridyloxy, and 4-methylisoquinolinyloxy.

Heterocyclic radicals, which include but are not limited to heteroaryls, include: furyl, (is)oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their nonaromatic counterparts. Further examples of heterocyclic radicals include thienyl, piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, octahydrobenzofuranyl, (iso)quinolinyl, naphthyridinyl, benzimidazolyl, and benzoxazolyl.

More general forms of substituted hydrocarbon radicals include hydroxyalkyl, hydroxyalkenyl, hydroxyalkynyl, hydroxycycloalkyl, hydroxyaryl, and corresponding forms for the prefixes amino-, halo-(e.g., fluoro-, chloro-, or bromo-), nitro-, alkyl-, phenyl-, cycloalkyl- and so on, or combinations of substituents. According to formula (I), therefore, substituted alkyls include, but are not limited to, hydroxyalkyl, alkoxyalkyl, aminoalkyl, nitroalkyl, haloalkyl, cyanoalkyl, alkylalkyl (branched alkyls, such as methylpentyl), (cycloalkyl)alkyl, phenylalkyl, alkylaminoalkyl, dialkylaminoalkyl, arylalkyl, aryloxyalkyl, arylalkyloxyalkyl, (heterocyclic radical)alkyl, and (heterocyclic radical)oxyalkyl. Formula I thus includes hydroxyalkyl, hydroxyalkenyl, hydroxyalkynyl, hydroxycycloalkyl, hydroxyaryl, aminoalkyl, aminoalkenyl, aminoalkynyl, aminocycloalkyl, aminoaryl, alkylalkenyl, (alkylaryl)alkyl, (haloaryl)alkyl, (hydroxyaryl)alkynyl, and so forth. $R_6$, $R_7$, $R_8$, $R_9$, and $R_{10}$ include hydroxy($C_{1-8}$)alkyl, ($C_{1-5}$)alkoxy($C_{1-5}$)alkyl, aminoalkyl, (e.g., [($C_{1-4}$)alkyl]$_2$ aminomethyl), perhalo($C_{1-3}$)alkyl (e.g., trifluoromethyl or trifluoroethyl), ($C_{2-7}$)heterocycle($C_{1-5}$)alkyl, and aryloxy ($C_{1-5}$)alkyl. Similarly, $R_{10}$ includes hydroxy($C_{1-8}$)alkyl, ($C_{1-5}$) alkoxy($C_{1-5}$)alkyl and trifluoro($C_{1-6}$)alkyl. The term "alkyl" means straight and branched chain aliphatic groups. Typical alkyl groups include methyl, ethyl, isopropyl, tert-butyl, 2,3-dimethylhexyl, and 1,1-dimethylpentyl. The alkyl groups can be unsubstituted or substituted by halo, hydroxy, alkoxy, amino, alkylamino, dialkylamino, cycloalkyl, aryl, aryloxy, heteroaryl, or heteroaryloxy, as those terms are defined herein. Typical substituted alkyl groups include chloromethyl, 3-hydroxypropyl, 2-dimethylaminobutyl, and 2-(hydroxymethylamino)ethyl. Examples of aryl and aryloxy substituted alkyl groups include phenylmethyl, 2-phenylethyl, 3-chlorophenylmethyl, 1,1-dimethyl-3-(2-nitrophenoxy)butyl, and 3,4,5-trifluoronaphthylmethyl. Examples of alkyl groups substituted by a heteroaryl or heteroaryloxy group include thienylmethyl, 2-furylethyl, 6-furyloxyoctyl, 4-methylquinolyloxymethyl, and 6-isothiazolylhexyl. Cycloalkyl substituted alkyl groups include cyclopropylmethyl, 2-cyclohexyethyl, piperidyl-2-methyl, 2-(piperidin-1-yl)-ethyl, 3-(morpholin-4-yl)propyl.

The term "alkoxy" as used herein refers to a straight or branched alkyl chain attached to an oxygen atom. The term "$C_{1-8}$ alkoxy" as used herein refers to a straight or branched alkyl chain having from one to eight carbon atoms attached to an oxygen atom. Typical $C_{1-8}$ alkoxy groups include methoxy, ethoxy, propoxy, isopropoxy, butoxy, t-butoxy, pentoxy and the like. The term "$C_{1-8}$ alkoxy" includes within its definition the terms "$C_{1-6}$ alkoxy" and "$C_{1-4}$ alkoxy".

"Alkenyl" means a straight or branched carbon chain having one or more double bonds. Examples include but-2-enyl, 2-methyl-prop-2-enyl, 1,1-dimethyl-hex-4-enyl, 3-ethyl-4-methyl-pent-2-enyl, and 3-isopropyl-pent-4-enyl. The alkenyl groups can be substituted with halo, hydroxy, alkoxy, amino, alkylamino, dialkylamino, aryl, aryloxy, heteroaryl, or heteroyloxy, for example 2-bromoethenyl, 3-hydroxy-2-butenyl, 1-aminoethenyl, 3-phenylprop-2-enyl, 6-thienyl-hex-2-enyl, 2-furyloxy-but-2-enyl, and 4-naphthyloxy-hex-2-enyl.

"Alkynyl" means a straight or branched carbon chain having at least one triple bond. Typical alkynyl groups include prop-2-ynyl, 2-methyl-hex-5-ynyl, 3,4-dimethyl-hex-5-ynyl, and 2-ethyl-but-3-ynyl. The alkynyl groups can be substituted as the alkyl and alkenyl groups, for example, by aryl, aryloxy, heteroaryl, or heteroaryloxy, for example 4-(2-fluorophenyl)-but-3-ynyl, 3-methyl-5-thienylpent-4-ynyl, 3-phenoxy-hex-4-ynyl, and 2-furyloxy-3-methyl-hex-4-ynyl.

The alkenyl and alkynyl groups can have one or more double bonds or triple bonds, respectively, or a combination of double and triple bonds. For example, typical groups having both double and triple bonds include hex-2-en-4-ynyl, 3-methyl-5-phenylpent-2-en-4-ynyl, and 3-thienyloxy-hex-3-en-5-ynyl.

The term "cycloalkyl" means a nonaromatic ring or fused rings. Examples include cyclopropyl, cyclobutyl, cyclopenyl, cyclooctyl, bicycloheptyl, adamantyl, and cyclohexyl. The ring can optionally contain one, two, or three heteroatoms selected from O, S, or N. Such groups include tetrahydrofuryl, tetrahydropyrrolyl, octahydrobenzofuranyl, morpholinyl, piperazinyl, pyrrolidinyl, piperidinyl, octahydroindolyl, and octahydrobenzothiofuranyl. The cycloalkyl groups can be substituted with the same substituents as an alkyl and alkenyl groups, for example, halo, hydroxy, aryl, and heteroaryloxy. Examples include 3-hydroxycyclohexyl, 2-aminocyclopropyl, 2-phenylpyrrolidinyl, and 3-thienylmorpholine-1-yl.

The 2-(4-bromo and 4-iodo phenylamino)-benzoic acid derivatives of Formula I can be prepared from commercially available starting materials utilizing synthetic methodologies well-known to those skilled in organic chemistry and as taught in WO 98/37881. A typical synthesis is carried out by reacting a 4-bromo or 4-iodo aniline with a benzoic acid having a leaving group at the 2-position to give a 2-(phenylamino)-benzoic acid. This process is depicted in Scheme 1.

Scheme 1

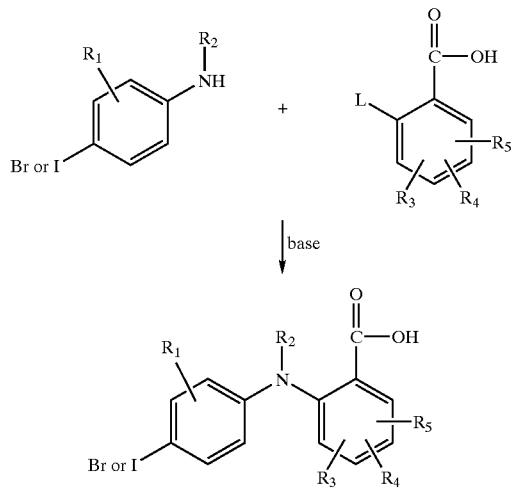

where L is a leaving group, for example, halo such as fluoro.

The reaction of aniline and the benzoic acid derivative generally is accomplished by mixing the benzoic acid with an equimolar quantity or excess of the aniline in an unreactive organic solvent such as tetrahydrofuran or toluene, in the presence of a base such as lithium diisopropylamide, n-butyl lithium, sodium hydride, triethylamine, and Hunig's base. The reaction generally is carried out at a temperature of about −78° C. to about 100° C., and normally is complete within about 2 hours to about 4 days. The product can be isolated by removing the solvent, for example by evaporation under reduced pressure, and further purified, if desired, by standard methods such as chromatography, crystallization, or distillation.

The 2-(phenylamino)-benzoic acid (e.g., Formula I, where $R_7$ is hydrogen) can be reacted with an organic or inorganic base such as pyridine, triethylamine, calcium carbonate, or sodium hydroxide to produce a pharmaceutically acceptable salt. The free acids can also be reacted with an alcohol of the formula $HOR_7$ (where $R_7$ is other than hydrogen, for example methyl) to produce the corresponding ester. Reaction of the benzoic acid with an alcohol can be carried out in the presence of a coupling agent. Typical coupling reagents include 2-ethoxy-1-ethoxycarbonyl-1,2-dihydroquinoline (EEDQ), 1,3-dicyclohexylcarbodiimide (DCC), bromo-tris(pyrrolidino)-phosphonium hexafluorophosphate (PyBrOP), and (benzotriazolyloxy) tripyrrolidino phosphonium hexafluorophosphate (PyBOP). The phenylamino benzoic acid and alcohol derivative normally are mixed in approximately equimolar quantities in an unreactive organic solvent such as dichloromethane, tetrahydrofuran, chloroform, or xylene, and an equimolar quantity of the coupling reagent is added. A base such as triethylamine or diisopropylethylamine can be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone, diethyl ether, or ethanol.

The benzamides of the invention, Formula I where Z is $CONR_6R_7$, are readily prepared by reacting the foregoing benzoic acids with an amine of the formula $HNR_6R_7$. The reaction is carried out by reacting approximately equimolar quantities of the benzoic acid and amine in an unreactive organic solvent in the presence of a coupling reagent. Typical solvents are chloroform, dichloromethane, tetrahydrofuran, benzene, toluene, and xylene. Typical coupling reagents include DCC, EEDQ, PyBrOP, and PyBOP. The reaction is generally complete after about 10 minutes to about 2 hours when carried out at a temperature of about 0° C. to about 60° C. The product amide is readily isolated by removing the reaction solvent, for instance by evaporation, and further purification can be accomplished by normal methods such as chromatography, crystallization, or distillation. The hydrazides ($z=CONHNR_{10}R_{11}$) are similarly prepared by coupling a benzoic acid with a hydrazine of the formula $H_2HNR_{10}R_{11}$.

The benzyl alcohols of the invention, compounds of Formula I where Z is $CH_2OR_6$ and $R_6$ is hydrogen, are readily prepared by reduction of the corresponding benzoic acid according to the following scheme

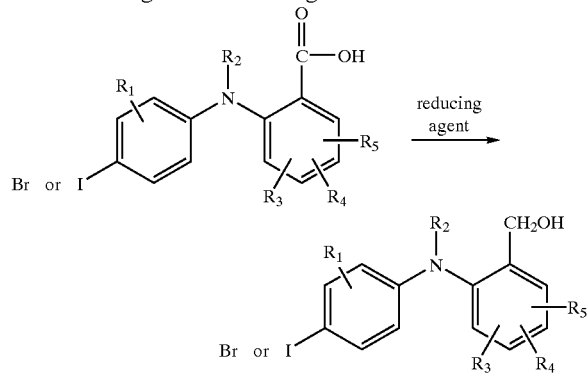

Typical reducing agents commonly employed include borane in tetrahydrofuran. The reduction normally is carried out in an unreactive organic solvent such as tetrahydrofuran, and generally is complete within about 2 hours to about 24 hours when conducted at a temperature of about 0° C. to about 40° C.

The 4-bromo and 4-iodo phenylamino benzhydroxamic acid derivatives of Formula II can be prepared from commercially available starting materials utilizing synthetic methodologies well-known to those skilled in organic chemistry and taught in WO 98/37881. A typical synthesis is carried out by reacting a 4-bromo or 4-iodo aniline with a benzoic acid having a leaving group at the 2-position to give a phenylamino benzoic acid, and then reacting the benzoic acid phenylamino derivative with a hydroxylamine derivative. This process is depicted in Scheme 1a.

Scheme 1a

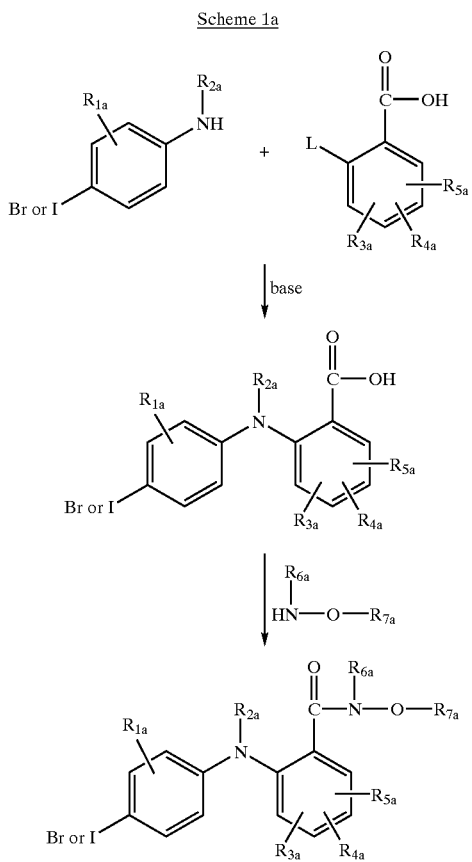

where L is a leaving group, for example, halo such as fluoro, chloro, bromo or iodo, or an activated hydroxy group such as a diethylphosphate, trimethylsilyloxy, p-nitrophenoxy, or phenylsulfonoxy.

The reaction of aniline and the benzoic acid derivative generally is accomplished by mixing the benzoic acid with an equimolar quantity or excess of the aniline in an unreactive organic solvent such as tetrahydrofuran, or toluene, in the presence of a base such as lithium diisopropylamide, n-butyl lithium, sodium hydride, and sodium amide. The reaction generally is carried out at a temperature of about −78° C. to about 25° C., and normally is complete within about 2 hours to about 4 days. The product can be isolated by removing the solvent, for example by evaporation under reduced pressure, and further purified, if desired, by standard methods such as chromatography, crystallization, or distillation.

The phenylamino benzoic acid next is reacted with a hydroxylamine derivative $HNR_{6a}OR_{7a}$ in the presence of a peptide coupling reagent. Hydroxylamine derivatives that can be employed include methoxyamine, N-ethylisopropoxy amine, and tetrahydro-oxazine. Typical coupling reagents include 2-ethoxy-1-ethoxycarbonyl-1,2-dihydroquinoline (EEDQ), 1,3-dicyclohexylcarbodiimide (DCC), bromo-tris(pyrrolidino)-phosphonium hexafluorophosphate (PyBrOP) and (benzotriazolyloxy)tripyrrolidino phosphonium hexafluorophosphate (PyBOP). The phenylamino benzoic acid and hydroxylamino derivative normally are mixed in approximately equimolar quantities in an unreactive organic solvent such as dichloromethane, tetrahydrofuran, chloroform, or xylene, and an equimolar quantity of the coupling reagent is added. A base such as triethylamine or diisopropylethylamine can be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone, diethyl ether, or ethanol.

An alternative method for making the invention compounds involves first converting a benzoic acid to a hydroxamic acid derivative, and then reacting the hydroxamic acid derivative with an aniline. This synthetic sequence is depicted in Scheme 2.

Scheme 2

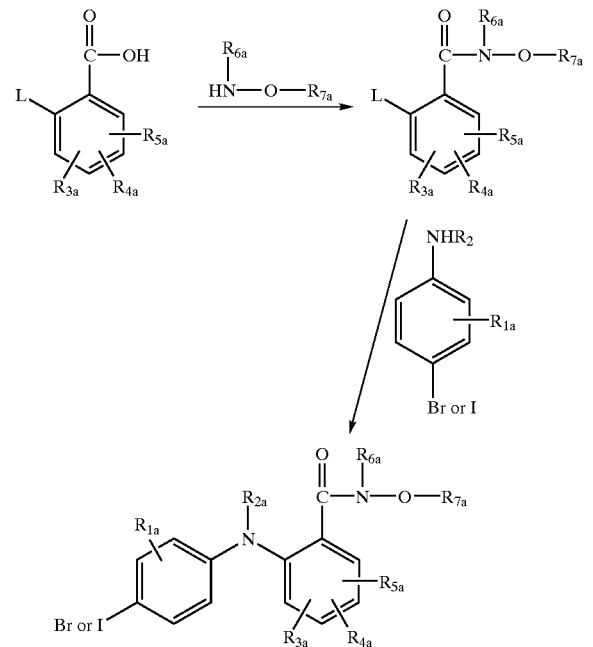

where L is a leaving group. The general reaction conditions for both of the steps in Scheme 2 are the same as those described above for Scheme 1a.

Yet another method for making invention compounds comprises reacting a phenylamino benzhydroxamic acid with an ester forming group as depicted in Scheme 3.

Scheme 3

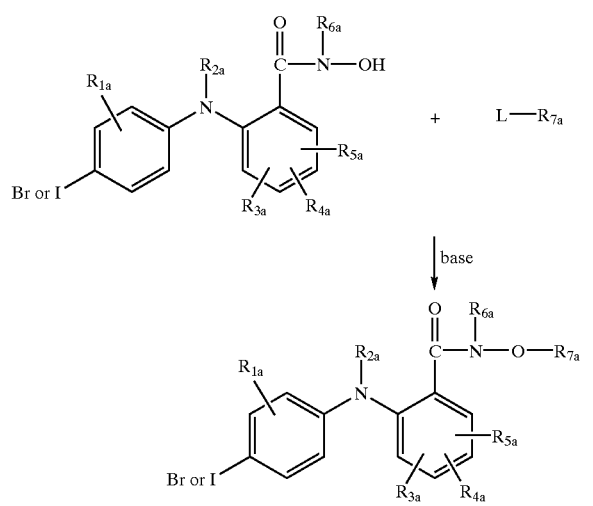

where L is a leaving group such as halo, and a base is triethylamine or diisopropylamine.

The compounds of formula III can be prepared from commercially available starting materials utilizing techniques and procedures readily available to one of ordinary skill in the art, as tought in WO 02/06213 typical syntheses are set forth in the following Schemes.

The compounds of formula III are generally obtained by the union of 2-(arylamino)-benzoic acids (1) with alkoxyamines (2) by the action of a peptide coupling agent in the presence of a base, as shown in Scheme lb. Preferred coupling agents include diphenylphoshinic chloride (DPP-Cl), benzotriazol-yl-oxy-tripyrolidinophosphonium hexafluorophosphate (PyBOP), benzotriazol-1-yloxy-tris (dimethylamino)phosphonium hexafluorophosphate (BOP), N,N'-dicyclohexylcarbodiimide (DCC), 1-ethyl-3-(3-dimethylaminopropyl)carbodiimide hydrochloride (EDCI), or 1,1'-carbonyldimidazole (CDI). Preferred bases include diisopropylethylamine, triethylamine, 4-methylmorpholine, or pyridine or a substituted pyridine, for example, 4-dimethyaminopyridine or 2,6-dimethylpyridine. Preferred solvents are polar aprotic solvents such as dichloromethane, tetrahydrofuran, or dimethylformamide. The reactions are generally carried out at a temperature between about −78° C. to about 25° C., and are normally complete within about 2 hours to about 5 days. The product amides can be isolated by removing the solvent, for example by evaporation under reduced pressure, and further purified, if desired, by standard methods such as chromatography, crystallization, or distillation.

Scheme 1b
General Preparation of Benzamides from Benzoic Acids

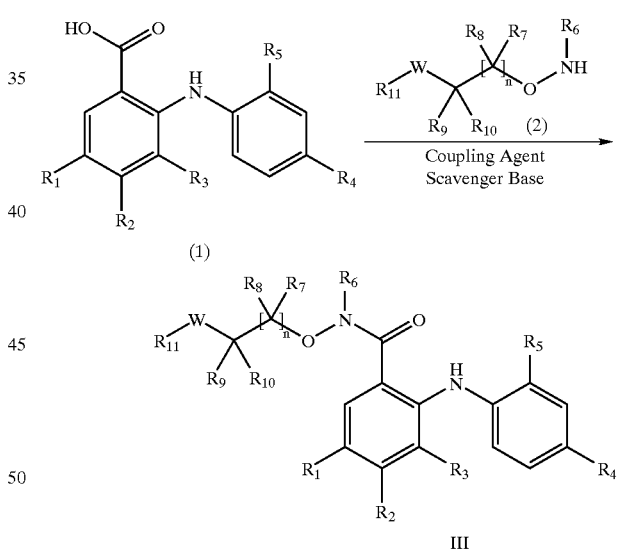

Alternately, disclosed compounds are also generally prepared as shown in Scheme 2a by the contact of alkoxyamine (2) with "activated" benzoic acid derivatives (3), wherein the activating group "X" completes an acid halide, anhydride, mixed anhydride, or an activated ester, such as a pentafluorophenyl ester, nitrophenyl ester or thioester. Preferred bases include diisopropylethylamine, triethylamine, 4-methylmorpholine, imidazole, pyridine or a substituted pyridine, for example, 4-dimethylaminopyridine or 2,6-dimethylpyridine. Preferred solvents are polar aprotic solvents such as dichloromethane, tetrahydrofuran, or dimethylformamide. These synthetic strategies, which are suitable for both conventional or combinatorial (parallel synthesis)

synthetic methods are further exemplified in examples below.

Scheme 2a
General Preparation of Benzamides from "Activated" Benzoic Acid Derivatives

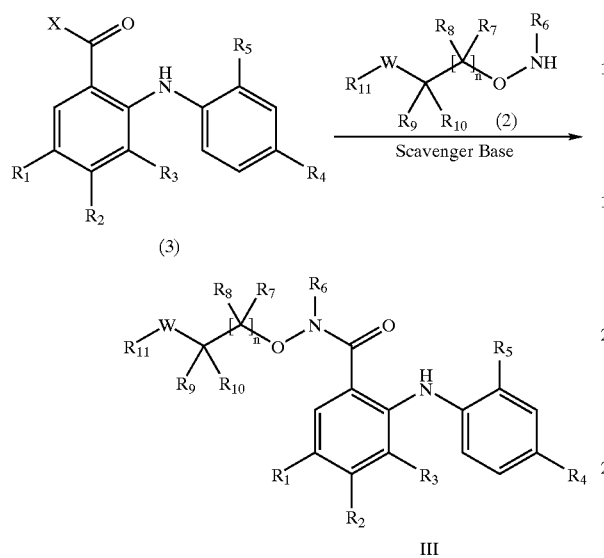

Preferred combinatorial methods are outlined in Scheme 3a, wherein the compounds of formula III are obtained by the reaction of an excess of pentafluorophenyl esters (4) with alkoxyamines (2) in the presence of polymer supported (PS) 4-methylmorpholine (5) in dimethylformamide with mechanical shaking. After a reaction period of about 16 to 72 hours, polymer supported amine (6) is added with dichloromethane. After an additional several hours of mechanical agitation, targets III are obtained by filtration, solvent evaporation and chromatographic purification.

Scheme 3a
General Combinatorial Preparation of Benzamide from Benzoic Acid Pentafluorophenyl Esters

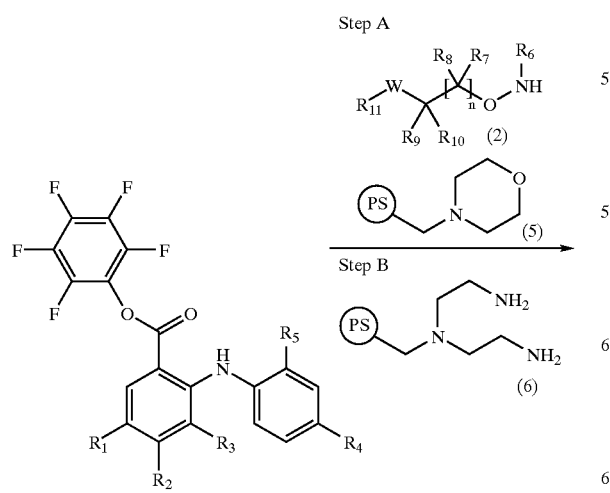

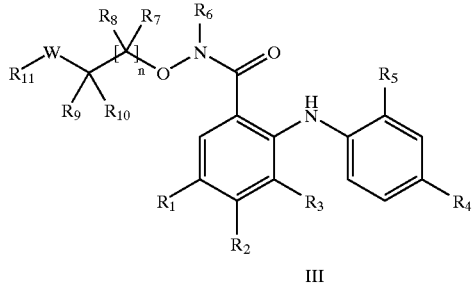

For the preparation of compounds of formula III wherein $R_{11}$=hydrogen, preferred synthetic modes may utilize a reagent of formula (2), wherein $R_6$, $R_7$, $R_8$, $R_9$, $R_{10}$ are defined as for formula III, above, and $R_{11}$ is a standard hydroxyl (W=O) or amino (W=NRa) protecting group. In such instances, general schemes 1b, 2a and 3a, above may be modified to include a standard removal of the said protecting group. Suitable protecting groups include, but are not limited to, vinyl ethers, silyl ethers, acetals, acetonides, and carbamates. Examples of such modifications are outlined below.

As illustrated in Scheme 4, preferred compounds of formula IIa may be obtained by the reaction of benzoic acids (1) with vinyl ether (7), a peptide coupling agent (for example, PyBOP) and a base (for example, diisopropylethylamine) to afford vinyl ether amide (8). Further treatment of vinyl ether (8) with acid affords the compounds of formula IIa.

Scheme 4
Representative Preparation of Hydroxylated Benzamides Using a Vinyl Ether as a Hydroxyl Protecting Group

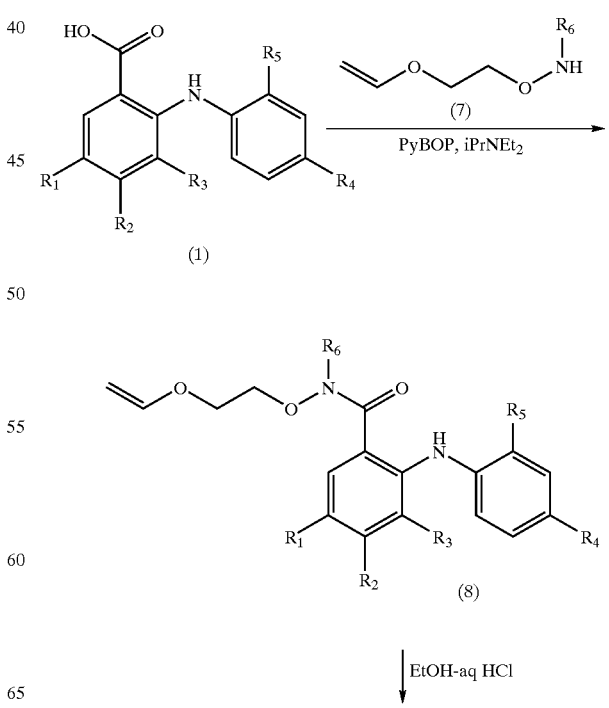

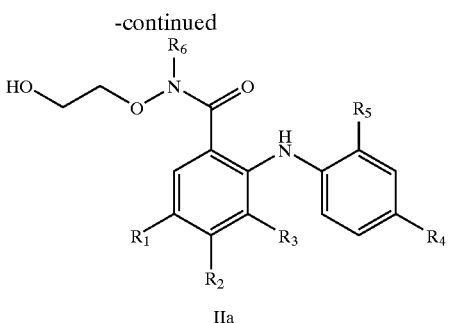

IIa

As shown below in Scheme 5, preferred compounds of formula IIb may also be obtained by the reaction of benzoic acids (1) with a suitable protecting group, such as tert-butyldimethylsilyl ether (9), in the presence a peptide coupling agent (for example, PyBOP) and a tertiary amine base (for example, diisopropylethylamine) to afford tert-butyldimethylsilyl ether amide (10). Further treatment of silyl ether (10) with acid in a protic solvent affords the compounds of formula IIb.

Scheme 5
Representative Preparation of Hydroxylated Benzamides
Using a Silyl Ether as a Hydroxyl Protecting Group

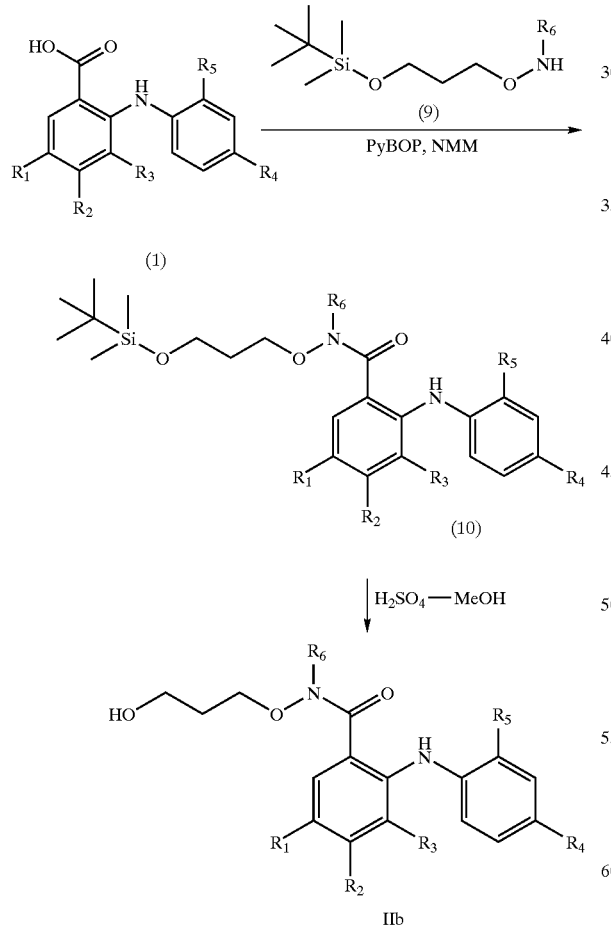

Preferred compounds of formula IVa can be prepared by similar methods, as illustrated in Scheme 6. For example, treatment of benzoic acids (1) with carbamate (11) in the presence of a peptide coupling agent, for example diphenylphosphinic chloride (DPP-Cl), in the presence of a tertiary amine base, for example 4-methylmorpholine (NMM) affords carbamate amide (12). Subsequent treatment of (12) with a suitable acid, for example trifluoracetic acid or hydrogen chloride, gives rise to the amines of general formula IVa, which may be isolated as acid salts or neutralized under standard conditions to afford free bases.

Scheme 6
Representative Preparation of Amino-Substituted Benzamides
Using a tert-Butyl Carbonate as an Amino Protecting Group

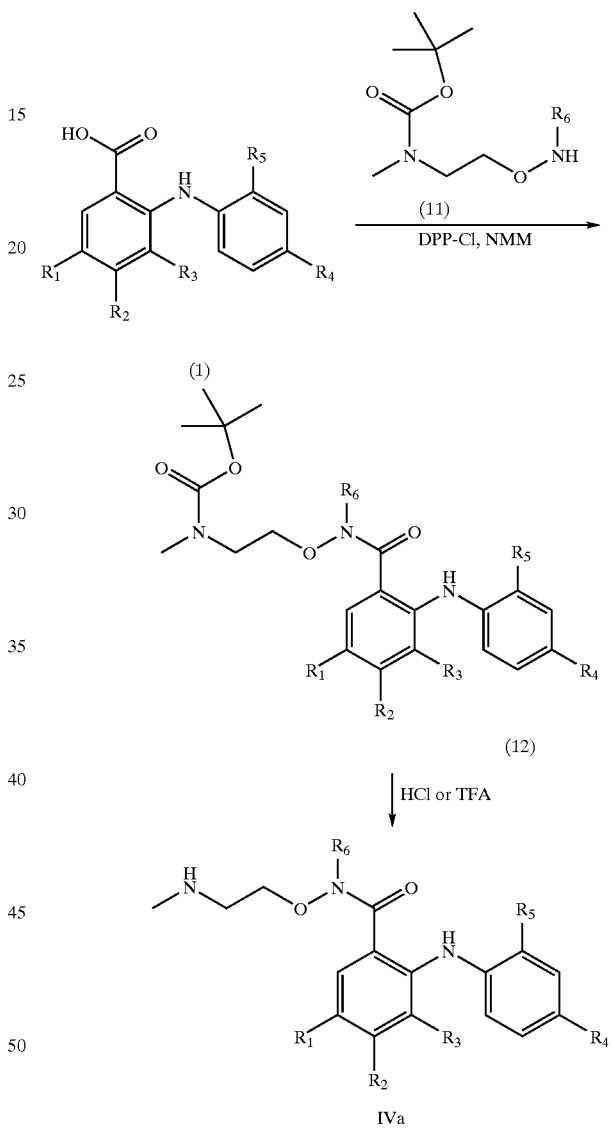

Further examples of the use of protecting group strategies are illustrated in the synthesis of preferred compounds of formula IIIa shown in Scheme 7. Acetonide-amides (14) are readily obtained by the union of acetonide (13) with benzoic acid (1) in the presence of a peptide coupling agent (for example, DPP-Cl) and a tertiary base, for example, 4-methylmorpholine (NMM). Alternately, they may be prepared according to Scheme 2 by the treatment of benzoic acid pentafluorophenyl esters (4) with acetonide (13) in the presence of a tertiary amine base (for example, diisopropylethylamine). Conversion of acetonide-amides (14) to preferred compounds IIIa can be accomplished by treatment under standard acidic hydrolysis conditions, for example p-toluenesulfonic acid in methanol.

Scheme 7
Prepresentative Preparation of Dihydroxylated Benzamides Using an Acetonide as a Diol Protecting Group

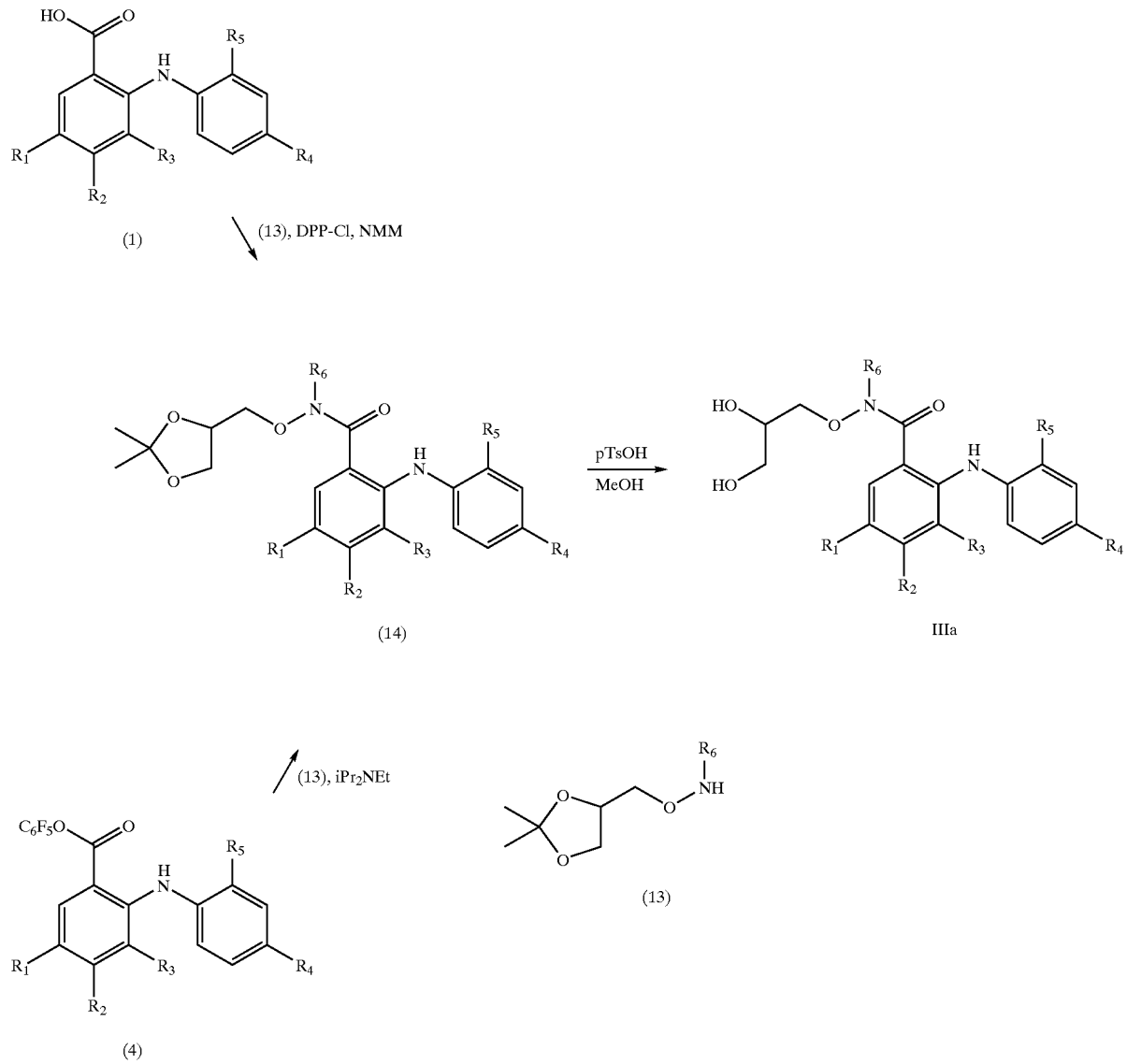

The compounds of formula III can also be prepared by the modification of other compounds of formula III. For example, compounds of formula III, where $R_6$=H (15) may be converted to compounds of formula III, where $R_6$=alkyl (16) by treatment with alkylating agents (for example, iodomethane) in the presence of a base (for example, potassium carbonate). Alternately, compounds of formula III, where $R_{11}$=H (17) may be converted to compounds of formula III, where $R_{11}$=alkylcarbonyl (18) by treatment with an acid chloride (for example, acetyl chloride) and a base, such as triethylamine. Additionally, a compound of formula III, where $R_4$=H (19) can be prepared from a compound of formula III, where $R_4$=Iodo (20). Illustrations of these examples are found in Schemes 8–10.

Scheme 8
Representative Preparation of Tertiary Benzamides by N-Alkylation

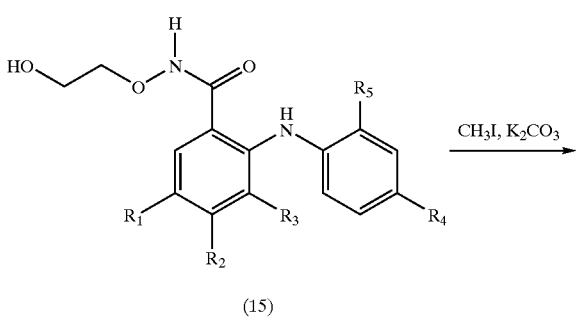

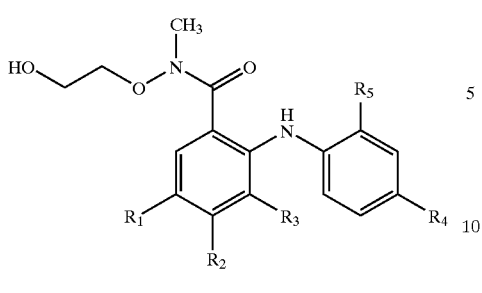

(16)

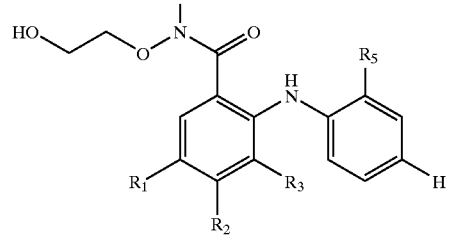

(20)

Scheme 9
Representative Preparation of Acetates by Acetylation

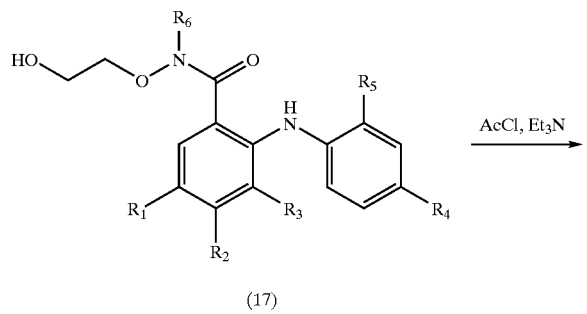

Scheme 10
Representative Hydrogenolysis of Aryl Iodides

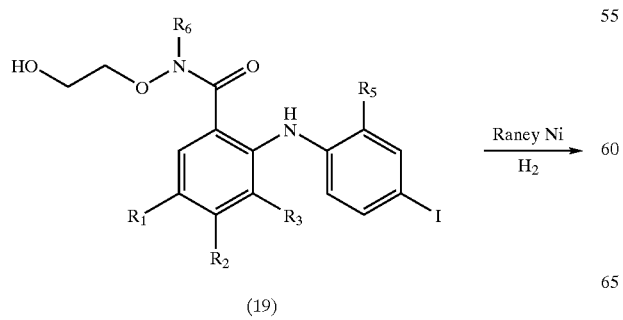

The examples presented below are intended to illustrate particular embodiments of the invention and are not intended to limit the scope of the specification, including the claims, in any way.

The following detailed examples illustrate the inhibition of neutrophil migration/chemotaxis provided by the method of this invention.

EXAMPLES

Materials and Methods:

Reagents and Animals

For all experiments, male New Zealand White rabbits (3.0–3.5 kg) purchased from Charles River Breeding Lab (Wilmington, Mass., USA) were used. Phospho specific antibodies and ECL reagents utilized for Western blotting included, p44/42 MAP (ERK) and p38 MAPK kinase (New England Biolabs, Waltham, Mass.). IL-8 was obtained from Sigma Chemical Co. (St. Louis, Mo.) and prostaglandin $E_2$ ($PGE_2$) from Caymen Chemical, Ann Arbor, Mich.), Lymphoprep sedimentation solution was obtained from NycoMed, Inc. RIPA buffer was prepared from Dubelcco's Phosphate Buffered Saline (PBS), SDS, and Sodium Deoxycholate from Sigma Chemical Co., and NP-40 from Amersham Pharmacia Biotech.

Isolation of Neutrophils

Polymorphonuclear leukocytes (PMNs) were isolated from whole blood obtained from healthy human donors. Plasma was separated from the remainder of the blood using a Dextran density gradient. Red blood cells (RBCs) and PMNs were further isolated by centrifugation at 2500 rpm for 15 minutes, using a Lymphoprep sedimentation solution. RBCs were lysed with 0.2% NaCl, neutralized with 1.8% NaCl, and the remaining neutrophils were resuspended in RPMI binding buffer at a final concentration of 10 million cells/mL.

In Vitro Neutrophil Chemotaxis

The neutrophil chemotaxis assay was conducted with 1 million cells per well in 3 µM pore size polycarbonate membrane transwell plates (Corning-Costar, Cambridge, Mass.). The various inhibitors were prepared as 1 or 10 mM stock solutions in dimethyl sulphoxide (DMSO). Inhibitor dilutions were prepared in RPMI binding buffer, maintaining a constant final concentration of DMSO in all conditions. Neutrophils were preincubated with the respective inhibitor in the top well of the plate for 30 minutes at room temperature prior to exposure to IL-8. An equivalent concentration of the respective inhibitor was placed in the bottom well to prevent any concentration gradient. DMSO concentration was maintained in all wells as a vehicle control. A concentration of 3.125 nM human IL-8 was added to bottom wells only for chemotaxis assays, and plates were incubated at 37° C. for 3 hours. Neutrophils that migrated completely across the 3-$\mu$M filter were quantitated using FACS analysis with appropriate forward and sideward scatter. Percentage inhibition relative to the positive control (IL-8 alone) was calculated for each condition after subtracting the blank reading (no IL-8).

Activation of Kinases

Neutrophils were preincubated with the respective inhibitor for 30 minutes at room temperature in 1.5-mL microfuge tubes prior to addition of IL-8 (3.125 nM). A time course was conducted initially and revealed that activation of ERK is optimal at 5 minutes following exposure to IL-8. Thus, neutrophils were exposed to IL-8 for 5 minutes at room temperature, after which whole cell lysates were obtained via lysis with RIPA buffer and analyzed by Western blot analysis using phospho specific antibodies, p44/42 MAP (ERK) and p38 MAPK kinase. Standard Western blotting was performed using chemiluminescence. All blots were normalized with the respective nonphosphorylated antibodies.

IL-8 Skin Recruitment Model

The animals were fed Purina Laboratory Rabbit Diet #5321 and housed according to institutional guidelines. Just prior to the start of a study, a 10×30 cm rectangular area for intradermal (ID) injection was shaved on the rabbits' backs using an electric shaver equipped with a #40 surgical blade.

Rabbits were orally dosed with either vehicle control or 2-(2-chloro-4-iodo-phenylamino)-N-cyclopropylmethoxy-3,4-difluoro-benzamide (30 mg/kg) three times at intervals of 8 hours before the experiment was performed. In control rabbits, the vehicle was administered. At t=0, rabbits received an intravenous (IV) 14.5-ng/kg (10 $\mu$Ci) dose of human $^{125}$I-IL-8 (Amersham Life Science, Budhinghamshire, England) using a 27-guage E-Z infusion set (Deseret Medical Inc, Sandy, Utah). At t=15 minutes, rabbits were anesthetized with isoflurane gas and injected ID (100 $\mu$L/site) with 0.01 to 3.3 $\mu$g human IL-8 (LeukoSite Inc., Boston, Mass.). The vehicle for the i.d. chemokine injections always consisted of sterile saline supplemented with 0.2% bovine albumin (BSA) (Sigma Chemical Co., St. Louis, Mo.) and 0.01 mM prostaglandin $E_2$ ($PGE_2$) (Caymen Chemical, Ann Arbor, Mich.). At t=85 minutes, rabbits were euthanized with a 0.5 mL IV dose of Beuthanasia-D Special (Schering-Plough Animal Health, Kenilworth, N.J.), and skin biopsies were obtained using a 6.35 mm diameter punch (O'Brien Consolidated Industries, Lewiston, Me.). In initial experiments, punches of different diameters (4.76, 6.35, 7.94, 9.53, 11.11, 12.70, 14.29, 15.88, and 17.46 mm) were also used to assess the size of the recruitment area. The biopsies were weighed and sample-associated radioactivity was determined using a gamma counter (Packard Model #05005, Downers Grove, Ill.).

In Vivo Experiment Data Analysis

In each experiment, triplicate samples were obtained for each experimental condition. In studies where IL-8 was not tested or the highest 1-$\mu$g dose of IL-8 was not used, the data is expressed as either raw counts or adjusted counts. Counts were adjusted by first subtracting out baseline control values, normalizing for differences in tissue weight, and adjusting the activity to that of a sample with a theoretical 100 mg tissue weight. In dose-response studies where the 1-$\mu$g dose of IL-8 was used, the weight-normalization background (vehicle-treated skin) was subtracted from weight-normalized treated samples, and the data was then expressed as a percent maximal response to the 1-$\mu$g dose of IL-8. The dose of 1 $\mu$g has been shown historically in our lab to produce the approximate maximal recruitment response to IL-8. Normalizing the data with this method reduces the inter-animal variability presumable due to differences in blood neutrophil count.

Results are expressed as mean+SEM. Statistical evaluation was performed using the General Linear Models Procedure and Repeated Measures of Analysis of Variance with p value of less than 0.01 considered significant.

Example 1

Figure 1A:
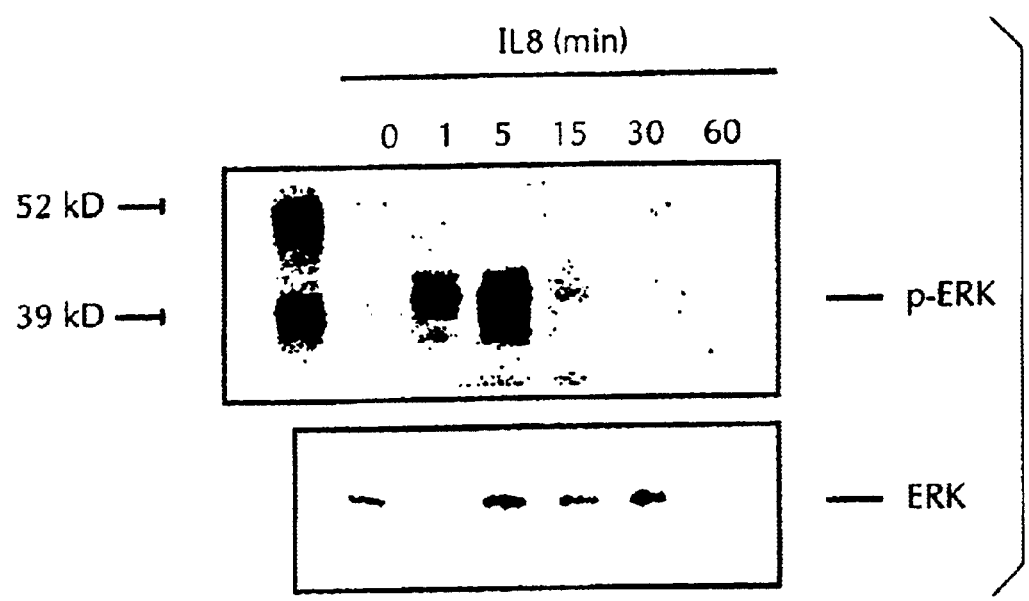
FIG. 1 shows that 2-(2-chloro-4-iodo-phenylamino)-N-cyclopropylmethoxy-3,4-difluoro-benzamide (Compound A) blocks IL-8 activated MAPK in human Polymorphonuclear leukocytes (PMNs). Activation of MAPK was examined by phospho-specific ERK antibody in isolated human PMNs that were stimulated with 3 nM of IL-8 for various periods of time (A). PMNs were incubated with 2-(2-chloro-4-iodo-phenylamino)-N-cyclopropylmethoxy-3,4-difluoro-benzamide (B) or Wortmannin (C) for 30 minutes and subsequently stimulated with 3 nM of IL-8 for 5 minutes. The effect of the inhibitors was monitored by measuring p-ERK activity by Western blotting. The blots were normalized using the ERK antibody.

IL-8 Activation of ERK is Inhibited by 2-(2-chloro-4-iodo-phenylamino)-N-cyclopropylmethoxy-3,4-difluoro-benzamide (Compound A) and Wortmannin To confirm IL-8 activation of ERK, neutrophils were stimulated with 3 nM of IL-8 for various periods of time, ranging from 0 to 30 minutes (FIG. 1A). Consistent with previous observations, IL-8 activation of ERK was evident by 1-minute post-IL-8 stimulation, however was maximal at 5 minutes posttreatment. No visible ERK activation was noticed after 15 minutes of IL-8 treatment. Hence, for all subsequent experiments, to evaluate the inhibitory effects of specific kinase inhibitors, neutrophils were stimulated with IL-8 for 5 minutes after incubation with appropriate inhibitors. These results are consistent with previous observations, where IL-8 stimulation of neutrophils or fibroblast cells transfected with CXCR1 of CXCR2 activated ERK in a time and dose dependent manner (Shyamala V., Khoja H. Interleukin-8 receptors R1 and R2 activate mitogen-activated protein kinases and induce c-fos, independent of Ras and Raf-1 in Chinese hamster ovary cells. *Biochemistry* 1998;37:15918–15924; Knall C., Young S., Nick J. A., Buhl A. M., Worthen G. S., Johnson G. L. Interleukin-8 regulation of the Ras/Raf/mitogen-activated protein kinase pathway in human neutrophils. *J. Biol. Chem.* 1996;271:2832–2838).

Figure 1B:
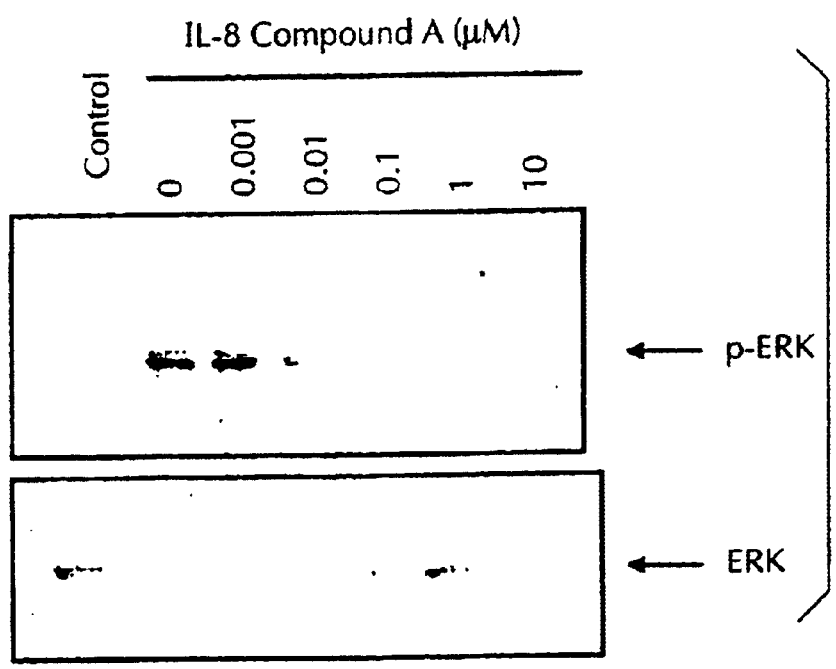

While Wortmannin is an established PI3K inhibitor, 2-(2-chloro-4-iodo-phenylamino)-N-cyclopropylmethoxy-3,4-difluoro-benzamide was recently described as a potent, specific, small molecule, allosteric MEK1 inhibitor, with an $IC_{50}$ of 17 nM in in vitro kinase assays. Similarly, in cellular assays with colon cancer cells, 2-(2-chloro-4-iodo-phenylamino)-N-cyclopropylmethoxy-3,4-difluoro-benzamide decreased the endogenous constitutive MAPK activation or growth in soft agar with an $IC_{50}$ of 0.15 $\mu$M. To examine the role of MEK1/2 or PI3K in IL-8 activation of ERK, PMNs were incubated with various concentrations of 2-(2-chloro-4-iodo-phenylamino)-N-cyclopropylmethoxy-3,4-difluoro-benzamide or Wortmannin (0 to 100 $\mu$M) for 30 minutes and subsequently treated with IL-8 for 5 minutes. Both 2-(2-chloro-4-iodo-phenylamino)-N-cyclopropylmethoxy-3,4-difluoro-benzamide and Wortmannin exhibited a dose dependent inhibition of IL-8 activation ERK (FIGS. 1B and C). However, 2-(2-chloro-4-iodo-phenylamino)-N-cyclopropylmethoxy-3,4-difluoro-benzamide was much more potent than Wortmannin. 2-(2-Chloro-4-iodo-phenylamino)-N-cyclopropylmethoxy-3,4-difluoro-benzamide starts inhibiting ERK activation at concentrations of 0.01 $\mu$M and almost completely blocked the activation of the ERK (FIG. 1B) by 0.1 $\mu$M. The role of PI3K in IL-8 activation of ERK has been controversial. It was found that inhibition of PI3K using Wortmannin, marginally decreases the IL-8-induced ERK activation at lower concentrations of the drug. However, at higher concentrations (10 $\mu$M) the ERK activation by IL-8 was completely blocked. No visible cytotoxicity effects on the PMNs were noticed at higher concentrations of the drug. These results confirm that IL-8 activates ERK through MEK1/2 and also suggests that activation of ERK may be partly mediated by a PI3K-dependent pathway. In parallel, kinase assays were performed to examine the MEK1/2 activity in response to IL-8. Consistent with ERK activity results, it was found that MEK1/2 is activated in response to IL-8, and this activation was inhibited by pre-treatment with 2-(2-chloro-4-iodo-phenylamino)-N-cyclopropylmethoxy-3,4-difluoro-benzamide or Wortmannin. Taken together, these results suggest that IL-8 activates ERK through a PI3K- and MEK1/2-dependent pathway.

Example 2

Figure 2:
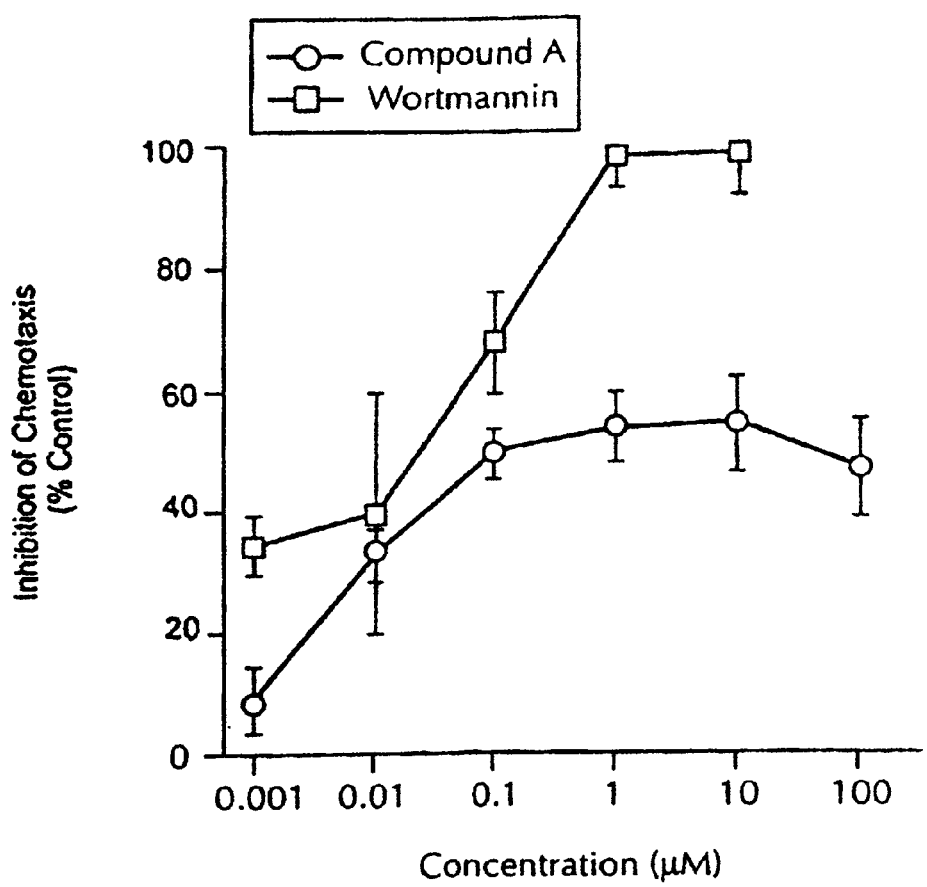
FIG. 2 shows the inhibition of neutrophil chemotaxis with 2-(2-chloro-4-iodo-phenylamino)-N-cyclopropylmethoxy-3,4-difluoro-benzamide (Compound A) or Wortmannin at various concentrations. In a trans-well migration chamber, neutrophils were pre-incubated with various concentrations of either 2-(2-chloro-4-iodo-phenylamino)-N-cyclopropylmethoxy-3,4-difluoro-benzamide or Wortmannin. Subsequently, the cells were stimulated with 3.125 nM of IL-8 for a period of 3 hours at which time the migrated cells were quantified using a cell sorter as described elsewhere. Percent inhibition was calculated based on the differences in the number of migrated cells compared to IL-8 alone controls.

2-(2-Chloro-4-iodo-phenylamino)-N-cyclopropylmethoxy-3,4-difluoro-benzamide (Compound A) or Wortmannin Inhibits IL-8-Stimulated Neutrophil Chemotaxis To assess the role of ERK in mediating the IL-8 originated neutrophil chemotaxis, we initially tested the efficacy of 2-(2-chloro-4-iodo-phenylamino)-N-cyclopropylmethoxy-3,4-difluoro-benzamide or Wortmannin in an in vitro chemotaxis transwell chamber assay. MEK inhibitor, 2-(2-chloro-4-iodo-phenylamino)-N-cyclopropylmethoxy-3,4-difluoro-benzamide, inhibited in vitro neutrophil chemotaxis with an $IC_{50}$ of 0.14 $\mu$M. As seen in FIG. 2, inhibition of chemotaxis followed a dose response curve, with minimal inhibition at 0.001 $\mu$M, increasing to about 60% at concentrations of 0.1 $\mu$M. However, there was no additional increase in the chemotaxis inhibition at higher concentrations, 1, 10, or 100 $\mu$M. This is in agreement with the fact that 0.1 $\mu$M of 2-(2-chloro-4-iodo-phenylamino)-N-cyclopropylmethoxy-3,4-difluoro-benzamide almost completely blocks the IL-8 activation of ERK, and additional increase in the concentration of the inhibitor yields no added benefit. The $IC_{50}$ of 2-(2-chloro-4-iodo-phenylamino)-N-cyclopropylmethoxy-3,4-difluoro-benzamide is consistent with previously published reports (Sebolt-Leopold J. S., Dudley D. T., Herrera R., Van Becelaere K., Wiland A., Gowan R. C., Tecle H., et al. Blockade of the MAP kinase pathway suppresses growth of colon tumors in vivo. Nat. Med. 1999;5:810–816). In order to compare the results better, both the chemotaxis assay and Western analysis for ERK activation were performed on the same samples from at least three different donors.

Figure 1C:
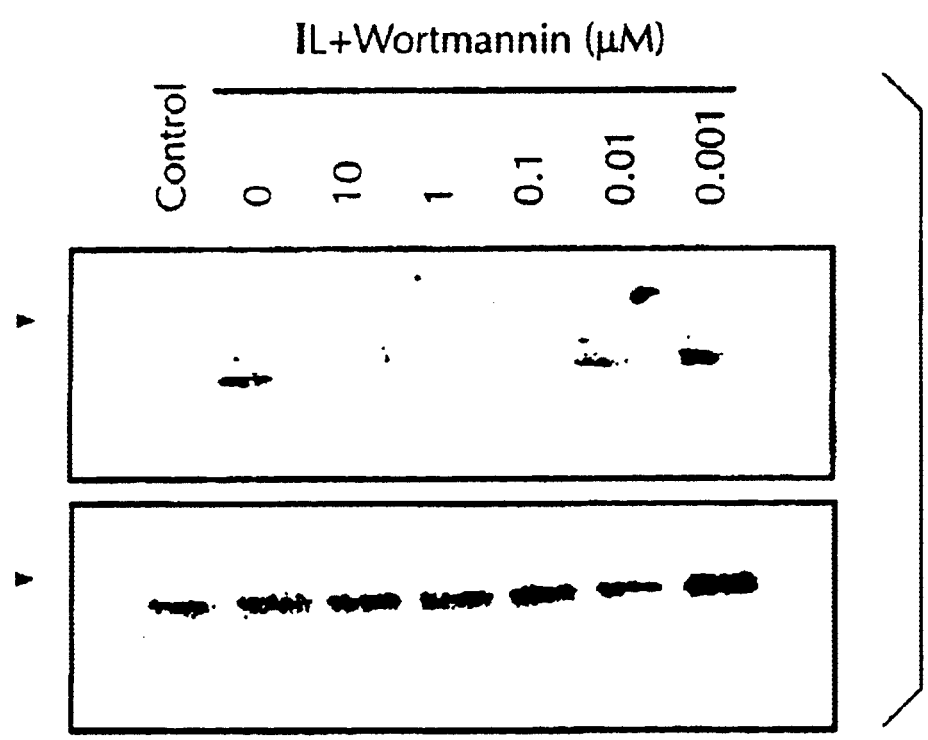

Inhibition of PI3K with Wortmannin also inhibited neutrophil chemotaxis (FIG. 2). However, Wortmannin was much more potent that 2-(2-chloro-4-iodo-phenylamino)-N-cyclopropylmethoxy-3,4-difluoro-benzamide ($IC_{50}$=0.02 $\mu$M). In contrast to 2-(2-chloro-4-iodo-phenylamino)-N-cyclopropylmethoxy-3,4-difluoro-benzamide, Wortmannin exhibited a steep dose response curve, and completely blocked the IL-8-induced neutrophil chemotaxis by 1 to 10 $\mu$M. At lower concentration of Wortmannin (0.001 $\mu$M), a modest 25% to 30% inhibition is noticed, but at 0.1 $\mu$M, the inhibition was much more potent (60%–70%) and reaches 100% at 1 $\mu$M. The robust increase in the potency correlates well with the ability of Wortmannin to block IL-8 activation of ERK only at higher concentrations but not at lower concentrations (FIG. 1C). These observations suggested that at lower concentrations, Wortmannin blocks PI3K mediated but ERK-independent pathways. However, it can block the ERK-dependent pathways at higher concentrations. Both of the pathways are responsible for IL-8-mediated chemotaxis.

Example 3

Figure 3A:
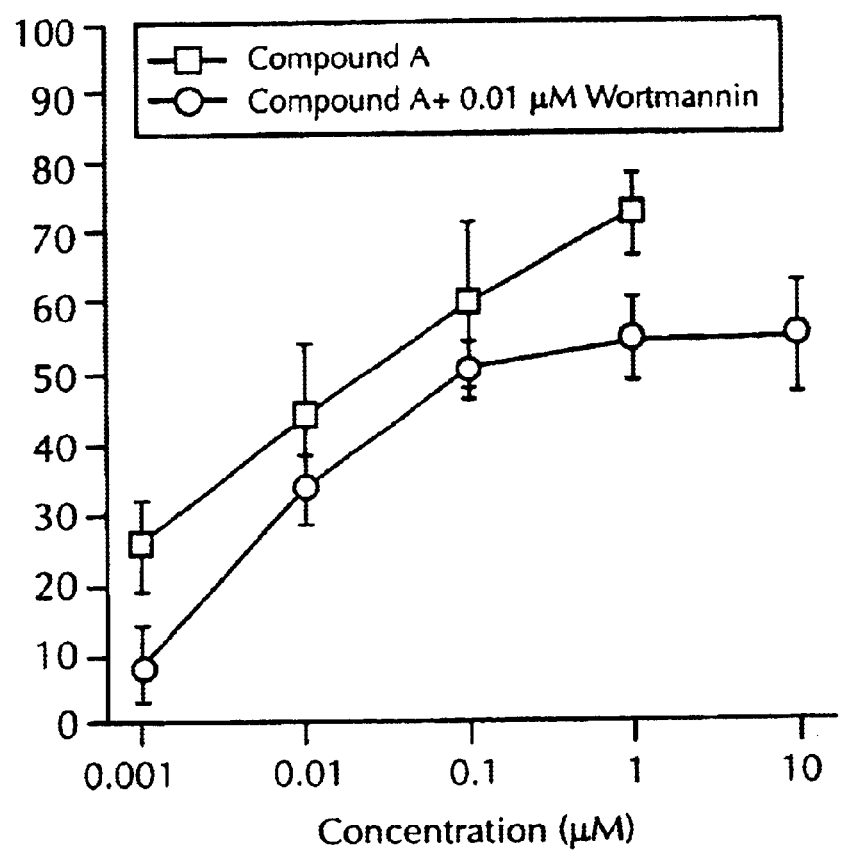
FIG. 3 shows the additive effects of 2-(2-chloro-4-iodo-phenylamino)-N-cyclopropylmethoxy-3,4-difluoro-benzamide (Compound A) and Wortmannin in blocking the IL-8 mediated neutrophil chemotaxis. Neutrophils were pre-incubated with a constant concentration of Wortmannin (0.01 µM, panel A) or 2-(2-chloro-4-iodo-phenylamino)-N-cyclopropylmethoxy-3,4-difluoro-benzamide (0.1 µM, panel B) and varying concentrations of 2-(2-chloro-4-iodo-phenylamino)-N-cyclopropylmethoxy-3,4-difluoro-benzamide (panel A) or Wortmannin (panel B) for 30 minutes prior to subsequent IL-8 (3.125 nM) stimulation.
Figure 3B:
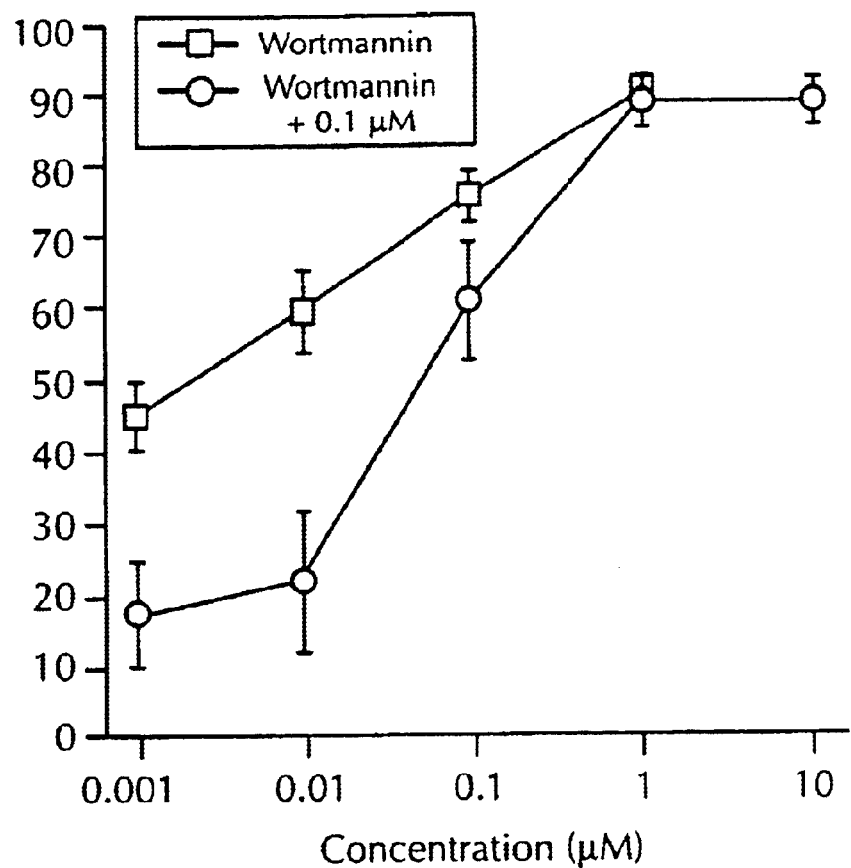

Additional Effects of 2-(2-chloro-4-iodo-phenylamino)-N-cyclopropylmethoxy-3,4-difluoro-benzamide (Comppund A) or Wortmannin in Chemotaxis Inhibition In order to better establish the presence of two pathways involved in IL-8-induced neutrophil chemotaxis, the two inhibitors, MEK and PI3K, were combined. In one set of experiments, various doses of 2-(2-chloro-4-iodo-phenylamino)-N-cyclopropylmethoxy-3,4-difluoro-benzamide were tested together with one concentration (0.01 $\mu$M) of Wortmannin, and in the other set of experiments, various doses of Wortmannin were tested together with one concentration (0.1 $\mu$M) of 2-(2-chloro-4-iodo-phenylamino)-N-cyclopropylmethoxy-3,4-difluoro-benzamide (FIG. 3).

The concentration of 0.01 $\mu$M for Wortmannin was chosen based on the Western blot observations; at this concentration Wortmannin had a minimal effect on IL-8-induced ERK activation but inhibited ~30% of chemotaxis. Upon addition of 2-(2-chloro-4-iodo-phenylamino)-N-cyclopropylmethoxy-3,4-difluoro-benzamide to the 0.01 $\mu$M Wortmannin, inhibition of chemotaxis increased in a dose dependent manner, however, plateaued off at ~70%, unlike the maximal ~50% inhibition witnessed with 2-(2-chloro-4-iodo-phenylamino)-N-cyclopropylmethoxy-3,4-difluoro-benzamide alone. Since it is evident that Wortmannin does not block ERK at this concentration, the difference in inhibition seems to represent the additive effect of Wortmannin on MEK-independent pathways.

Similarly, the constant presence of 0.1 $\mu$M 2-(2-chloro-4-iodo-phenylamino)-N-cyclopropylmethoxy-3,4-difluoro-benzamide (at which concentration ERK activation by IL-8 is completely inhibited) with increasing concentration of Wortmannin shifts up the Wortmannin dose-response curve. 2-(2-chloro-4-iodo-phenylamino)-N-cyclopropylmethoxy-3,4-difluoro-benzamide (0.01 $\mu$M) blocks ERK activation completely and helps to inhibit chemotaxis approximately 50%. At lower Wortmannin concentrations where MEK-independent pathways were predominantly blocked, the additional blocking effects imparted by the MEK inhibitor were much more evident (28% vs. 65% in 0.01 $\mu$M Wortmannin alone compared to Wortmannin+2-(2-chloro-4-iodo-phenylamino)-N-cyclopropylmethoxy-3,4-difluoro-benzamide). The additive effects of the compounds in either combination of treatments suggest that IL-8-induced chemotactic signaling mechanisms bifurcate at the level of PI3K; one MEK-dependent and the other MEK-independent.

To test if the role of ERK is equivalent at any given dose of IL-8, in vitro chemotaxis assays were performed with a single concentration (0.1 $\mu$M) of 2-(2-chloro-4-iodo-phenylamino)-N-cyclopropylmethoxy-3,4-difluoro-benzamide at varying doses of IL-8 (0.001 to 100 nM). The data (FIG. 4) indicates that 0.1 $\mu$M 2-(2-chloro-4-iodo-phenylamino)-N-cyclopropylmethoxy-3,4-difluoro-benzamide that blocks consistently ~60% of the chemotaxis at 3 nM of IL-8, can block greater ~80% at 0.1 nM and only ~30% at 100 nM IL-8. This suggests that the role of the ERK pathway in mediating IL-8-induced chemotaxis at lower concentrations of IL-8 is greater than at higher concentrations.

Example 4

Effect of MEK Inhibitor In Vivo

To test if the observations noticed in the in vitro chemotaxis experiments are valid in vivo, a recently developed novel in vivo rabbit neutrophil recruitment assay as described in the Materials and Methods was employed. As it was established earlier that rabbit neutrophils respond to human IL-8 (Belayet H. M., Kanayama N., Khatun S., Asahina T., Okada Y., Kitamura K., et al. Pharmacologic doses of interleukin 8 suppositories induce follicular maturation in rabbits. *Cytokine* 2000;12:361–367), human IL-8 was used in our in vivo study. Rabbits were PO dosed with either vehicle control or 2-(2-chloro-4-iodo-phenylamino)-N-cyclopropylmethoxy-3,4-difluoro-benzamide (30 mg/kg) three times at intervals of 8 hours before the experiment was performed. A 3-hour interval was allowed between the final dose and the performance of the experiments. As described elsewhere, the neutrophil recruitment was measured as the bound radiolabeled ($^{125}$I) IL-8. In the control animals, the neutrophil recruitment exhibited a clear dose-dependent increase, whereas the animals dosed with 2-(2-chloro-4-iodo-phenylamino)-N-cyclopropylmethoxy-3,4-difluoro-benzamide had a consistently decreased number of neutrophils recruited to the skin at all IL-8 concentrations tested (FIG. 5). However, the decrease was significant at higher concentrations tested (~50%). Though the real concentrations of IL-8 tested in vitro and in vivo cannot be directly compared, these in vivo observations are in parallel with in vitro observations, where the inhibition ranged at ~50% at 3 nM of IL-8. Thus, it appears that the MEK inhibitor, 2-(2-chloro-4-iodo-phenylamino)-N-cyclopropylmethoxy-3,4-difluoro-benzamide, does partially inhibit neutrophil migration/chemotaxis in vivo as well as in vitro.

Example 5
Cellular Assay for Measuring MEK Inhibition

The evaluation of the compounds as MEK inhibitors was performed in an assay that measures their ability to inhibit phosphorylation of MAP kinase (ERK) in murine colon 26 (C26) carcinoma cells. Since ERK1 and ERK2 represent the only known substrates for MEK, measurement of inhibition of ERK phosphorylation in cells provides direct readout of cellular MEK inhibition by the compounds of the invention. Briefly, the assay involves treating exponentially growing C26 cells with varying concentrations of the test compound (or vehicle control) for one hour at 37° C. Cells are then rinsed free of compound/vehicle and lysed in a solution containing 70 mM NaCl, 50 mM glycerol phosphate, 10 mM HEPES, pH 7.4, 1% Triton X-100, 1 mM $Na_3VO_4$, 100 μM PMSF, 10 μM leupeptin and 10 μM pepstatin. Supernatants are then subjected to gel electrophoresis and Western blotting using a primary antibody recognizing dually phosphorylated ERK1 and ERK2. To evaluate total MAPK levels, blots were subsequently 'stripped' and re-probed with a 1:1 mixture of polyclonal antibodies recognizing unphosphorylated ERK1 and ERK2.

In view of the foregoing, it will be understood and appreciated that numerous modifications and variations of the aforedescribed invention may be readily implemented. The discussion, description, and examples set forth herein are illustrative of particular embodiments of the present invention, but are not meant to be limitations upon the practice thereof. It is the following claims, including all equivalents, which define the scope of the invention.

What is claimed is:

1. A method for inhibiting neutrophil migration in a patient in need of neutrophil migration inhibition, said method comprising administering to the patient a therapeutically effective amount of a compound that is a MEK inhibitor in combination with a therapeutically effective amount of a compound that is a phosphatidylinositol-3-kinase (PI3K) inhibitor.

2. A method for treating a neutrophil mediated disease or condition comprising administering to a patient a therapeutically effective amount of a compound that is a MEK inhibitor in combination with a therapeutically effective amount of a compound that is a phosphatidylinositol-3-kinase inhibitor.

3. The method according to claim 1, wherein the phosphatidylinositol-3-kinase inhibitor comprises Wortmannin.

4. The method according to claim 1, wherein the phosphatidylinositol-3-kinase inhibitor comprises 5,6-dimethoxy-3-phenoxy-N-1H-tetrazol-5-yl-benzo[b]thiophene-2-carboxamide.

5. The method according to claim 1, wherein the MEK inhibitor comprises 2-(2-chloro-4-iodo-phenylamino)-N-cyclopropylmethoxy-3,4-difluoro-benzamide.

6. The method according to claim 2, wherein the MEK inhibitor comprises 2-(2-chloro-4-iodo-phenylamino)-N-cyclopropylmethoxy-3,4-difluoro-benzamide.

7. The method according to claim 1, wherein the MEK inhibitor comprises N-cyclopropylmethoxy-3,4,5-trifluoro-2-(4-iodo-2-methyl-phenylamino)-benzamide.

8. The method of claim 1, wherein the MEK inhibitor comprises

5-Chloro-2-(2-chloro-4-iodo-phenylamino)-N-(2,3-dihydroxy-propoxy)-3,4-difluoro-benzamide;

3,4-Difluoro-2-(2-fluoro-4-iodo-phenylamino)-N-(2-hydroxy-ethoxy)-benzamide;

N-(2,3-Dihydroxy-propoxy)-3,4-difluoro-2-(2-fluoro-4-iodo-phenylamino)-benzamide;

5-Chloro-N-(2,3-dihydroxy-propoxy)-3,4-difluoro-2-(2-fluoro-4-iodo-phenylamino)-benzamide;

5-Chloro-N-((R)-2,3-dihydroxy-propoxy)-3,4-difluoro-2-(2-fluoro-4-iodo-phenylamino)-benzamide;

3,4-Difluoro-2-(2-fluoro-4-iodo-phenylamino)-N-(2-methylamino-ethoxy)-benzamide; hydrochloride;

N-((R)-2,3-Dihydroxy-propoxy)-3,4-difluoro-2-(2-fluoro-4-iodo-phenylamino)-benzamide;

N-((S)-2,3-Dihydroxy-propoxy)-3,4-difluoro-2-(2-fluoro-4-iodo-phenylamino)-benzamide;

5-Chloro-2-(2-chloro-4-iodo-phenylamino)-N-((S)-2,3-dihydroxy-propoxy)-3,4-difluoro-benzamide;

5-Chloro-2-(2-chloro-4-iodo-phenylamino)-N-((R)-2,3-dihydroxy-propoxy)-3,4-difluoro-benzamide;

5-Chloro-N-((S) 2,3-dihydroxy-propoxy)-3,4-difluoro-2-(2-fluoro-4-iodo-phenylamino)-benzamide;

3,4-Difluoro-2-(2-fluoro-4-iodo-phenylamino)-N-(2-hydroxy-1-hydroxymethyl-ethoxy)-benzamide; and 5-Chloro-3,4-difluoro-2-(2-fluoro-4-iodo-phenylamino)-N-(2-hydroxy-1-hydroxymethyl-ethoxy)-benzamide.

9. The method of claim 1 wherein the MEK inhibitor is a compound of Formula I:

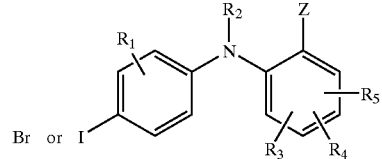

wherein:

$R_1$ is hydrogen, hydroxy, $C_1$–$C_8$ alkyl, $C_1$–$C_8$ alkoxy, halo, trifluoromethyl, or CN;

$R_2$ is hydrogen;

$R_3$, $R_4$, and $R_5$ independently are hydrogen, hydroxy, halo, trifluoromethyl, $C_1$–$C_8$ alkyl, $C_1$–$C_8$ alkoxy, nitro, ON, or —(O or NH)$_m$—(CH$_2$)$_n$—$R_9$, where $R_9$ is hydrogen, hydroxy, COOH, or $NR_{10}R_{11}$;

n is 0 to 4;

m is 0 or 1;

$R_{10}$ and $R_{11}$ independently are hydrogen or $C_1$–$C_8$ alkyl, or taken together with the nitrogen to which they are attached can complete a 3- to 10-member cyclic ring optionally containing 1, 2, or 3 additional heteroatoms selected from O, S, NH, or N—$C_1$–$C_8$ alkyl;

Z is $COOR_7$, tetrazolyl, $CONR_6R_7$, $CONHNR_{10}R_{11}$ or $CH_2OR_7$;

$R_6$ and $R_7$ independently are hydrogen, $C_1$–$C_8$ alkyl, $C_2$–$C_8$ alkenyl, $C_2$–$C_8$ alkynyl, $$\overset{O}{\underset{\|}{C}}-C_1-C_8 \text{ alkyl,}$$

aryl, heteroaryl, $C_3$–$C_{10}$ cycloalkyl, optionally containing one, two, or three heteroatoms selected from O, S, NH, or N alkyl; or $R_6$ and $R_7$ together with the nitrogen to which they are attached complete a 3- to 10-member cyclic ring optionally containing 1, 2, or 3 additional heteroatoms selected from O, S, NH, or N alkyl; and wherein any of the foregoing alkyl, alkenyl, and alkynyl groups can be unsubstituted or substituted by halo, hydroxy, alkoxy, amino, alkylamino, dialkylamino, cycloalkyl, aryl, aryloxy, heteroaryl, or heteroaryloxy, and the pharmaceutically acceptable salts, esters, amides, or prodrugs thereof.

10. The method of claim 1 wherein the MEK inhibitor is

[4-Chloro-2-(1H-tetrazol-5-yl)-phenyl]-(4-iodo-2-methyl-phenyl)-amine;

(4-iodo-2-methyl-phenyl)-[2-(1H-tetrazol-5-yl)-phenyl] amine; [4-nitro-2-(1H-tetrazol-5-yl)-phenyl]-(4-iodo-2-methyl-phenyl)-amine;

4-Fluoro-2-(4-iodo-2-methylphenylamino)benzoic acid;

3,4,5-Trifluoro-2-(4-iodo-2-methyl-phenylamino)-benzoic acid;

3,4-Difluoro-2-(4-iodo-2-methyl-phenylamino)-benzoic acid;

5-Bromo-3,4-difluoro-2-(4-iodo-2-methyl-phenylamino)-benzoic acid;

5-Chloro-2-(4-iodo-2-methyl-phenylamino)-benzoic acid;

Sodium 5-Chloro-2-(4-iodo-2-methyl-phenylamino)-benzoate;

5-Bromo-2-(4-iodo-2-methyl-phenylamino)-benzoic acid;

2-(4-Iodo-2-methyl-phenylamino)-5-nitro-benzoic acid;

4-Chloro-2-(4-iodo-2-methyl-phenylamino)-benzoic acid;

2-(4-Iodo-2-methyl-phenylamino)-benzoic acid;

5-Fluoro-2-(4-iodo-2-methyl-phenylamino)-benzoic acid;

5-Iodo-2-(4-iodo-2-methyl-phenylamino)-benzoic acid;

2,3,5-Trifluoro-4-(4-iodo-2-methyl-phenylamino)-benzoic acid;

2-(4-Iodo-phenylamino)-5-methoxy-benzoic acid;

5-Methyl-2-(4-iodo-2-methyl-phenylamino)-benzoic acid;

2-(4-Iodo-2-methyl-phenylamino)-4-nitro-benzoic acid;

2-(4-Bromo-2-methyl-phenylamino)-4-fluoro-benzoic acid;

2-(2-Bromo-4-iodo-phenylamino)-5-nitro-benzoic acid;

2-(4-Bromo-2-methyl-phenylamino)-3,4-difluoro-benzoic acid;

5-Chloro-N-(2-hydroxyethyl)-2-(4-iodo-2-methyl-phenylamino)-benzamide;

4-Fluoro-2-(4-iodo-2-methyl-phenylamino)-benzamide;

4-Fluoro-2-(4-iodo-2-methyl-phenylamino)-N-methyl-benzamide;

N-Ethyl-4-fluoro-2-(4-iodo-2-methyl-phenyl amino)-benzamide;

4-Fluoro-2-(4-iodo-2-methyl-phenylamino)-N,N-dimethyl-benzamide;

4-Fluoro-2-(4-iodo-2-methyl-phenylamino)-N-(1H-tetrazol-5-yl)-benzamide;

5-Bromo-2-(4-iodo-2-methyl-phenylamino)-benzamide;

5-Chloro-2-(4-iodo-2-methyl-phenylamino)-N,N-dimethyl-benzamide;

[5-Chloro-2-(4-iodo-2-methyl-phenylamino)-N-hydroxycarbonylmethyl-benzamide;

4-Fluoro-2-(4-iodo-2-methyl-phenylamino)-N-propyl-benzamide;

5-Bromo-N-(2-hydroxy-ethyl)-2-(4-iodo-2-methyl-phenylamino)-benzamide;

N,N-Diethyl-4-fluoro-2-(4-iodo-2-methyl-phenylamino)-benzamide;

4-Fluoro-N-{3-[4-(2-hydroxy-ethyl)-piperazin-1-yl]-propyl}-2-(4-iodo-2-methyl-phenylamino)-benzamide;

N,N-Diethyl-2-(4-iodo-2-methyl-phenylamino)-5-nitro-benzamide;

N-Butyl-4-fluoro-2-(4-iodo-2-methyl-phenylamino)-benzamide;

5-Chloro-N,N-diethyl-2-(4-iodo-2-methyl-phenylamino)-benzamide;

5-Bromo-2-(4-iodo-2-methyl-phenylamino)-N,N-dimethyl-benzamide;

5-Bromo-3,4-difluoro-N-(2-hydroxy-ethyl)-2-(4-iodo-2-methyl-phenylamino)-benzamide;

N-(2,3-Dihydroxy-propyl)-3,4-difluoro-2-(4-iodo-2-methyl-phenylamino)-benzamide;

5-Bromo-3,4-difluoro-2-(4-iodo-2-methyl-phenylamino)-N-(2-piperidin-1-yl-ethyl)-benzamide;

3,4-Difluoro-N-(2-hydroxy-ethyl)-2-(4-iodo-2-methyl-phenylamino)-benzamide;

N-(2,3-Dihydroxy-propyl)-4-fluoro-2-(4-iodo-2-methyl-phenylamino)-benzamide;

3,4-Difluoro-N-(3-hydroxy-propyl)-2-(4-iodo-2-methyl-phenylamino)-benzamide;

5-Bromo-3,4-difluoro-2-(4-iodo-2-methyl-phenylamino)-N-(2-pyrrolidin-1-yl-ethyl)-benzamide;

5-Bromo-3,4-difluoro-2-(4-iodo-2-methyl-phenylamino)-N-(2-pyridin-4-yl-ethyl)-benzamide;

4-Fluoro-N-(2-hydroxy-ethyl)-2-(4-iodo-2-methyl-phenylamino)-benzamide;

5-Bromo-N-(3-dimethylamino-propyl)-3,4-difluoro-2-(4-iodo-2-methyl-phenylamino)-benzamide;

5-Bromo-3,4-difluoro-2-(4-iodo-2-methyl-phenylamino)-N-(2-morpholin-4-yl-ethyl)-benzamide;

3,4-Difluoro-2-(4-iodo-2-methyl-phenylamino)-N-(2-morpholin-4-yl-ethyl)-benzamide;

3,4-Difluoro-2-(4-iodo-2-methyl-phenylamino)-N-(2-pyrrolidin-1-yl-ethyl)-benzamide;

3,4-Difluoro-2-(4-iodo-2-methyl-phenylamino)-N-(2-pyridin-4-yl-ethyl)-benzamide;

N-(3-Dimethylamino-propyl)-3,4-difluoro-2-(4-iodo-2-methyl-phenylamino)-benzamide;

N-Benzyl-4-fluoro-2-(4-iodo-2-methyl-phenylamino)-benzamide;
2-(4-Bromo-2-methyl-phenylamino)-3,4-difluoro-N-(2-hydroxy-ethyl)-benzamide;
4-Fluoro-2-(4-iodo-2-methyl-phenylamino)-N-(2-morpholin-4-yl-ethyl)-benzamide;
4-Fluoro-2-(4-iodo-2-methyl-phenylamino)-N-(3-piperidin-1-yl-propyl)-benzamide;
3,4-Difluoro-2-(4-iodo-2-methyl-phenylamino)-N-(3-piperidin-1-yl-propyl)-benzamide;
4-Fluoro-2-(4-iodo-2-methyl-phenylamino)-N-(2-thiophen-2-yl-ethyl)-benzamide;
4-Fluoro-2-(4-iodo-2-methyl-phenylamino)-N-(2-pyrrolidin-1-yl-ethyl)-benzamide;
2-(4-Bromo-2-methyl-phenylamino)-3,4-difluoro-N-(2-morpholin-4-yl-ethyl)-benzamide;
5-Bromo-3,4-difluoro-2-(4-iodo-2-methyl-phenylamino)-N-pyridin-4-ylmethyl-benzamide;
3,4-Difluoro-2-(4-iodo-2-methyl-phenylamino)-N-pyridin-4-ylmethyl-benzamide;
2-(4-Bromo-2-methyl-phenylamino)-N-(3-dimethylamino-propyl)-3,4-difluoro-benzamide;
4-Fluoro-2-(4-iodo-2-methyl-phenylamino)-N-pyridin-4-ylmethyl-benzamide;
4-Fluoro-2-(4-iodo-2-methyl-phenylamino)-N-(2-pyridin-4-yl-ethyl)-benzamide;
2-(4-Bromo-2-methyl-phenylamino)-3,4-difluoro-N-(2-pyridin-4-yl-ethyl)-benzamide;
2-(4-Bromo-2-methyl-phenylamino)-3,4-difluoro-N-(3-hydroxy-propyl)-benzamide;
2-(4-Bromo-2-methyl-phenylamino)-3,4-difluoro-N-(2-pyrrolidin-1-yl-ethyl)-benzamide;
4-Fluoro-2-(4-iodo-2-methyl-phenylamino)-N-phenethyl-benzamide;
2-(4-Bromo-2-methyl-phenylamino)-3,4-difluoro-N-(2-thiophen-2-yl-ethyl)-benzamide;
2-(4-Bromo-2-methyl-phenylamino)-3,4-difluoro-N-pyridin-4-ylmethyl-benzamide;
2-(4-Bromo-2-methyl-phenylamino)-3,4-difluoro-N-phenethyl-benzamide;
2-(4-Bromo-2-methyl-phenylamino)-3,4-difluoro-N-(2-piperidin-1-yl-ethyl)-benzamide;
5-Chloro-N-{3-[4-(2-hydroxy-ethyl)-piperazin-1-yl]-propyl}-2-(4-iodo-2-methyl-phenylamino)-benzamide;
5-Fluoro-N-{3-[4-(2-hydroxy-ethyl)-piperazin-1-yl]-propyl}-2-(4-iodo-2-methyl-phenylamino)-benzamide;
2-(4-Iodo-2-methyl-phenylamino)-5-nitro-N-pyridin-4-yl methyl-benzamide;
5-Bromo-N-{3-[4-(2-hydroxy-ethyl)-piperazin-1-yl]-propyl}-2-(4-iodo-2-methyl-phenylamino)-benzamide;
5-Chloro-N-(2-diethylamino-ethyl)-2-(4-iodo-2-methyl-phenylamino)-benzamide;
5-Chloro-2-(4-iodo-2-methyl-phenylamino)-N-(2-piperidin-1-yl-ethyl)-benzamide;
(3-Hydroxy-pyrrolidin-1-yl)-[2-(4-iodo-2-methyl-phenylamino)-5-nitro-phenyl]-methanone;
5-Chloro-2-(4-iodo-2-methyl-phenylamino)-N-(2-pyrrolidin-1-yl-ethyl)-benzamide;
5-Bromo-N-(2-diethylamino-ethyl)-2-(4-iodo-2-methyl-phenylamino)-benzamide;
N-{2-[Bis-(2-hydroxy-ethyl)-amino]-ethyl}-5-chloro-2-(4-iodo-2-methyl-phenylamino)-benzamide;
N-{2-[Bis-(2-hydroxy-ethyl)-amino]-ethyl}-5-bromo-2-(4-iodo-2-methyl-phenylamino)-benzamide;
N-{3-[4-(2-Hydroxy-ethyl)-piperazin-1-yl]-propyl}-2-(4-iodo-2-methyl-phenylamino)-benzamide;
5-Fluoro-2-(4-iodo-2-methyl-phenylamino)-N-pyridin-4-ylmethyl-benzamide;
5-Bromo-2-(4-iodo-2-ethyl-phenylamino)-N-(2-pyrrolidin-1-yl-ethyl)-benzamide;
5-Bromo-2-(4-iodo-2-methyl-phenylamino)-N-(2-piperidin-1-yl-ethyl)-benzamide;
5-Fluoro-2-(4-iodo-2-methyl-phenylamino)-N-(2-pyrrolidin-1-yl-ethyl)-benzamide;
5-Chloro-N-(3-dimethylamino-propyl)-2-(4-iodo-2-methyl-phenylamino)-benzamide;
N-{2-[Bis-(2-hydroxy-ethyl)-amino]-ethyl}-5-fluoro-2-(4-iodo-2-methyl-phenylamino)-benzamide;
5-Chloro-N-(3-hydroxy-propyl)-2-(4-iodo-2-methyl-phenylamino)-benzamide;
5-Chloro-N-(3-diethylamino-2-hydroxy-propyl)-2-(4-iodo-2-methyl-phenylamino)-benzamide;
5-Fluoro-2-(4-iodo-2-methyl-phenylamino)-N-(2-piperidin-1-yl-ethyl)-benzamide;
5-Bromo-N-(3-hydroxy-propyl)-2-(4-iodo-2-methyl-phenylamino)-benzamide;
5-Bromo-2-(4-iodo-2-methyl-phenylamino)-N-(3-piperidin-1-yl-propyl)-benzamide;
N-{2-[Bis-(2-hydroxy-ethyl)-amino]-ethyl}-2-(4-iodo-2-methyl-phenylamino)-5-nitro-benzamide;
5-Chloro-2-(4-iodo-2-methyl-phenylamino)-N-(2-morpholin-4-yl-ethyl)-benzamide;
5-Chloro-N-(3-diethylamino-propyl)-2-(4-iodo-2-methyl-phenylamino)-benzamide;
5-Chloro-N-(2-diisopropylamino-ethyl)-2-(4-iodo-2-methyl-phenylamino)-benzamide;
5-Chloro-2-(4-iodo-2-methyl-phenylamino)-N-(3-piperidin-1-yl-propyl)-benzamide;
2-(4-Iodo-2-methyl-phenylamino)-5-nitro-N-(2-piperidin-1-yl-ethyl)-benzamide;
5-Bromo-2-(4-iodo-2-methyl-phenylamino)-N-(2-piperazin-1-yl-ethyl)-benzamide;
N-(2-Diethylamino-ethyl)-5-fluoro-2-(4-iodo-2-methyl-phenylamino)-benzamide;
5-Bromo-N-(3-dimethylamino-propyl)-2-(4-iodo-2-methyl-phenylamino)-benzamide;
N-(3-Hydroxy-propyl)-2-(4-iodo-2-methyl-phenylamino)-5-nitro-benzamide;
5-Fluoro-N-(3-hydroxy-propyl)-2-(4-iodo-2-methyl-phenylamino)-benzamide;
N-(3-Diethylamino-propyl)-5-fluoro-2-(4-iodo-2-methyl-phenylamino)-benzamide;
N-(3-Diethylamino-propyl)-2-(4-iodo-2-methyl-phenylamino)-5-nitro-benzamide;
5-Bromo-2-(4-iodo-2-methyl-phenylamino)-N-(2-morpholin-4-yl-ethyl)-benzamide;
2-(4-Iodo-2-methyl-phenylamino)-5-nitro-N-(3-piperidin-1-yl-propyl)-benzamide;
1-[5-Fluoro-2-(4-iodo-2-methyl-phenylamino)-phenyl]-1-(3-hydroxy-pyrrolidin-1-yl)-methanone;
5-Bromo-N-(2-diisopropylamino-ethyl)-2-(4-iodo-2-methyl-phenylamino)-benzamide;
5-Fluoro-2-(4-iodo-2-methyl-phenylamino)-N-(2-morpholin-4-yl-ethyl)-benzamide;

5-Fluoro-2-(4-iodo-2-methyl-phenylamino)-N-(3-piperidin-1-yl-propyl)-benzamide;

1-[5-Fluoro-2-(4-iodo-2-methyl-phenylamino)-phenyl]-1-[4-(2-hydroxy-ethyl)-piperazin-1-yl]-methanone;

N-(3-Diethylamino-2-hydroxy-propyl)-5-fluoro-2-(4-iodo-2-methyl-phenylamino)-benzamide;

N-Cyclopropyl-5-fluoro-2-(4-iodo-2-methyl-phenylamino)-benzamide;

5-Chloro-N-(2-hydroxy-ethyl)-2-(4-iodo-2-methyl-phenylamino)-benzamide;

5-Fluoro-N-(2-hydroxy-ethyl)-2-(4-iodo-2-methyl-phenylamino)-benzamide;

N-Benzyloxy-5-fluoro-2-(4-iodo-2-methyl-phenylamino)-benzamide;

N-Benzyloxy-5-bromo-2-(4-iodo-2-methyl-phenylamino)-benzamide;

2-(4-Iodo-2-methyl-phenylamino)-5-nitro-N-(4-sulfamoyl-benzyl)-benzamide;

5-Bromo-N-(2-hydroxy-ethyl)-2-(4-iodo-2-methyl-phenyl amino)-benzamide;

N-(2-Hydroxy-ethyl)-5-iodo-2-(4-iodo-2-methyl-phenylamino)-benzamide;

N-(2-Hydroxy-ethyl)-2-(4-iodo-2-ethyl-phenylamino)-5-nitro-benzamide;

2-(4-Iodo-2-methyl-phenylamino)-N-methyl-5-nitro-N-phenyl-benzamide;

5-Chloro-N-cyclopropyl-2-(4-iodo-2-methyl-phenylamino)-benzamide;

5-Fluoro-2-(4-iodo-2-methyl-phenylamino)-N-methyl-N-phenyl-benzamide;

N-Allyl-5-fluoro-2-(4-iodo-2-methyl-phenylamino)-benzamide;

N-Benzyloxy-5-iodo-2-(4-iodo-2-methyl-phenylamino)-benzamide;

5-Fluoro-2-(4-iodo-2-methyl-phenylamino)-N-(4-sulfamoyl-benzyl)-benzamide;

N-Allyl-5-chloro-2-(4-iodo-2-methyl-phenylamino)-benzamide;

N-Cyclopropyl-2-(4-iodo-2-methyl-phenylamino)-5-nitro-benzamide;

5-Bromo-N-cyclopropyl-2-(4-iodo-2-methyl-phenylamino)-benzamide;

5-Chloro-2-(4-iodo-2-methyl-phenylamino)-N-methyl-N-phenyl-benzamide;

5-Iodo-2-(4-iodo-2-methyl-phenylamino)-N-(4-sulfamoyl-benzyl)-benzamide;

5-Bromo-2-(4-iodo-2-methyl-phenylamino)-N-(4-sulfamoyl-benzyl)-benzamide;

N-Allyl-2-(4-iodo-2-methyl-phenylamino)-5-nitro-benzamide;

2-(4-Iodo-2-methyl-phenylamino)-5-nitro-N-(4-sulfamoyl-benzyl)-benzamide;

N-Allyl-5-bromo-2-(4-iodo-2-methyl-phenylamino)-benzamide;

5-Fluoro-2-(4-iodo-2-methyl-phenylamino)-N-(3-methyl-benzyl)-benzamide;

N-Cyclopropyl-5-iodo-2-(4-iodo-2-methyl-phenylamino)-benzamide;

5-Bromo-2-(4-iodo-2-methyl-phenylamino)-N-methyl-N-phenyl-benzamide;

N-Benzyloxy-2-(4-iodo-2-methyl-phenylamino)-5-nitro-benzamide;

N-Cyclohexyl-5-iodo-2-(4-iodo-2-methyl-phenylamino)-benzamide;

N-Allyl-5-iodo-2-(4-iodo-2-methyl-phenylamino)-benzamide;

5-Iodo-2-(4-iodo-2-methyl-phenylamino)-N-(3-methyl-benzyl)-benzamide;

2-(4-Iodo-2-methyl-phenylamino)-N-(3-methyl-benzyl)-5-nitro-benzamide;

5-Iodo-2-(4-iodo-2-methyl-phenylamino)-N-methyl-N-phenyl-benzamide;

N-Cyclohexyl-5-fluoro-2-(4-iodo-2-methyl-phenylamino)-benzamide;

5-Chloro-N-cyclohexyl-2-(4-iodo-2-methyl-phenylamino)-benzamide;

5-Bromo-2-(4-iodo-2-methyl-phenylamino)-N-(3-methyl-benzyl)-benzamide;

5-Bromo-N-cyclohexyl-2-(4-iodo-2-methyl-phenylamino)-benzamide;

5-Chloro-2-(4-iodo-2-methyl-phenylamino)-N-(3-methyl-benzyl)-benzamide;

N-Cyclohexyl-2-(4-iodo-2-methyl-phenylamino)-5-nitro-benzamide;

N-Benzyloxy-5-bromo-2-(4-iodo-2-methyl-phenylamino)-benzamide;

N-Benzyloxy-5-fluoro-2-(4-iodo-2-methyl-phenylamino)-benzamide;

5-Chloro-N-(2-hydroxy-ethyl)-2-(4-iodo-2-methyl-phenylamino)-benzamide;

5-Bromo-N-(2-hydroxy-ethyl)-2-(4-iodo-2-methyl-phenylamino)-benzamide;

2-(4-Iodo-2-methyl-phenylamino)-N-methyl-5-nitro-N-phenyl-benzamide;

5-Chloro-2-(4-iodo-2-methyl-phenylamino)-N-methyl-N-phenyl-benzamide;

N-(2-Hydroxy-ethyl)-5-iodo-2-(4-iodo-2-methyl-phenylamino)-benzamide;

5-Chloro-N-cyclopropyl-2-(4-iodo-2-methyl-phenylamino)-benzamide;

N-Allyl-5-chloro-2-(4-iodo-2-methyl-phenylamino)-benzamide;

5-Fluoro-2-(4-iodo-2-methyl-phenylamino)-N-methyl-N-phenyl-benzamide;

N-(2-Hydroxy-ethyl)-2-(4-iodo-2-methyl-phenylamino)-5-nitro-benzamide;

5-Fluoro-N-(2-hydroxy-ethyl)-2-(4-iodo-2-methyl-phenylamino)-benzamide;

5-Bromo-N-cyclopropyl-2-(4-iodo-2-methyl-phenylamino)-benzamide;

N-Cyclopropyl-5-fluoro-2-(4-iodo-2-methyl-phenylamino)-benzamide;

5-Fluoro-2-(4-iodo-2-methyl-phenylamino)-N-(4-sulfamoyl-benzyl)-benzamide;

N-Cyclopropyl-2-(4-iodo-2-methyl-phenylamino)-5-nitro-benzamide;

N-Allyl-5-fluoro-2-(4-iodo-2-methyl-phenylamino)-benzamide;

N-Benzyloxy-5-iodo-2-(4-iodo-2-methyl-phenylamino)-benzamide;

N-Allyl-5-bromo-2-(4-iodo-2-methyl-phenylamino)-benzamide;

5-Bromo-2-(4-iodo-2-methyl-phenylamino)-N-(4-sulfamoyl-benzyl)-benzamide;

5-Bromo-2-(4-iodo-2-methyl-phenylamino)-N-methyl-N-phenyl-benzamide;

N-Allyl-2-(4-iodo-2-methyl-phenylamino)-5-nitro-benzamide;

4-Fluoro-2-(4-iodo-2-methyl-phenylamino)-benzyl alcohol;

[5-Chloro-2-(4-iodo-2-methyl-phenylamino)-phenyl]-methanol;

[2-(4-Iodo-2-methyl-phenylamino)-5-nitro-phenyl]-methanol;

[5-Bromo-2-(4-iodo-2-methyl-phenylamino)-phenyl]-methanol; or

N-Allyl-2-(4-iodo-2-methyl-phenylamino)-5-nitro-benzamide.

11. The method of claim 1 wherein the MEK inhibitor is a compound of Formula II:

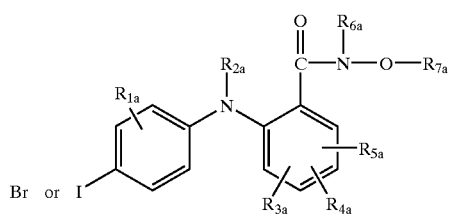

wherein:

$R_{1a}$ is hydrogen, hydroxy, $C_1$–$C_8$ alkyl, $C_1$–$C_8$ alkoxy, halo, trifluoromethyl, or CN;

$R_{2a}$ is hydrogen;

$R_{3a}$, $R_{4a}$, and $R_{5a}$ independently are hydrogen, hydroxy, halo, trifluoromethyl, $C_1$–$C_8$ alkyl, $C_1$–$C_8$ alkoxy, nitro, CN, or (O or NH)$_m$—(CH$_2$)$_n$—$R_{9a}$, where $R_{9a}$ is hydrogen, hydroxy, CO$_2$H or NR$_{10a}$R$_{11a}$;

n is 0 to 4;

m is 0 or 1;

$R_{10a}$ and $R_{11a}$ independently are hydrogen or $C_1$–$C_8$ alkyl, or taken together with the nitrogen to which they are attached can complete a 3- to 10-member cyclic ring optionally containing one, two, or three additional heteroatoms selected from O, S, NH, or N—$C_1$–$C_8$ alkyl;

$R_{6a}$ is hydrogen, $C_1$–$C_8$ alkyl,

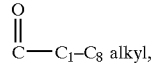

alkyl, aryl, aralkyl, or $C_3$–$C_{10}$ cycloalkyl;

$R_{7a}$ is hydrogen, $C_1$–$C_8$ alkyl, $C_2$–$C_8$ alkenyl, $C_2$–$C_8$ alkynyl, $C_3$–$C_{10}$ cycloalkyl optionally containing a heteroatom selected from O, S, or NR$_{9a}$; and wherein any of the foregoing alkyl, alkenyl, and alkynyl groups can be unsubstituted or substituted by cycloalkyl, aryl, aryloxy, heteroaryl, or heteroaryloxy; or $R_{6a}$ and $R_{7a}$ taken together with the N to which they are attached can complete a 5- to 10-membered cyclic ring, optionally containing one, two, or three additional heteroatoms selected from O, S, or NR$_{10a}$R$_{11a}$, and the pharmaceutically acceptable salts, esters, amides or prodrugs thereof.

12. The method of claim 11 wherein the MEK inhibitor is

4-Fluoro-N-hydroxy-2-(4-iodo-2-methyl-phenylamino)-benzamide;

4-Fluoro-2-(4-iodo-2-methyl-phenylamino)-N-(methoxy)-benzamide;

4-Fluoro-2-(4-iodo-2-methyl-phenylamino)-N-(prop-2-ynyloxy)-benzamide;

4-Fluoro-2-(4-iodo-2-methyl-phenylamino)-N-(2-phenoxyethoxy)-benzamide;

4-Fluoro-2-(4-iodo-2-methyl-phenylamino)-N-(2-thienylmethoxy)-benzamide;

4-Fluoro-2-(4-iodo-2-methyl-phenylamino)-N-(prop-2-enyloxy)-benzamide;

4-Fluoro-2-(4-iodo-2-methyl-phenylamino)-N-(cyclopropylmethoxy)-benzamide;

4-Fluoro-2-(4-iodo-2-methyl-phenylamino)-N-(cyclopentoxy)-benzamide;

3,4-Difluoro-2-(4-iodo-2-methyl-phenylamino)-N-(3-furylmethoxy)-benzamide;

3,4-Difluoro-2-(4-iodo-2-methyl-phenylamino)-N-ethoxy-benzamide;

3,4-Difluoro-2-(4-iodo-2-methyl-phenylamino)-N-(but-2-enyloxy)-benzamide;

3,4-Difluoro-2-(4-iodo-2-methyl-phenylamino)-N-(cyclopropylmethoxy)-benzamide;

3,4-Difluoro-2-(4-iodo-2-methyl-phenylamino)-N-(1-methylprop-2-ynyloxy)-benzamide;

3,4-Difluoro-2-(4-iodo-2-methyl-phenylamino)-N-(3-phenylprop-2-ynyloxy)-benzamide;

3,4-Difluoro-2-(4-iodo-2-methyl-phenylamino)-N-(3-methyl-5-phenylpent-2-en-4-ynyloxy)-benzamide;

3,4-Difluoro-2-(4-iodo-2-methyl-phenylamino)-N-(prop-2-ynyloxy)-benzamide; 3,4-Difluoro-2-(4-iodo-2-methyl-phenylamino)-N-(propoxy)-benzamide;

3,4-Difluoro-2-(4-iodo-2-methyl-phenylamino)-N-(cyclobutyloxy)-benzamide;

3,4-Difluoro-2-(4-iodo-2-methyl-phenylamino)-N-(2-thienylmethoxy)-benzamide;

3,4-Difluoro-2-(4-iodo-2-methyl-phenylamino)-N-(2-methyl-prop-2-enyloxy)-benzamide;

3,4-Difluoro-2-(4-iodo-2-methyl-phenylamino)-N-(2-phenoxyethoxy)-benzamide;

3,4-Difluoro-2-(4-iodo-2-methyl-phenylamino)-N-(but-2-enyloxy)-benzamide;

3,4-Difluoro-2-(4-iodo-2-methyl-phenylamino)-N-(but-3-ynyloxy)-benzamide;

3,4-Difluoro-2-(4-iodo-2-methyl-phenylamino)-N-(cyclopentyloxy)-benzamide;

3,4-Difluoro-2-(4-iodo-2-methyl-phenylamino)-N-(3-(2-fluorophenyl)-prop-2-ynyloxy)-benzamide;

5-Bromo-3,4-difluoro-N-hydroxy-2-(4-iodo-2-methyl-phenylamino)-benzamide;

5-Bromo-3,4-difluoro-2-(4-iodo-2-methyl-phenylamino)-N-(n-propoxy)-benzamide;

5-Bromo-3,4-difluoro-N-(furan-3-ylmethoxy)-2-(4-iodo-2-methyl-phenylamino)-benzamide;

5-Bromo-N-(but-2-enyloxy)-3,4-difluoro-2-(4-iodo-2-methyl-phenylamino)-benzamide;

5-Bromo-N-butoxy-3,4-difluoro-2-(4-iodo-2-methyl-phenylamino)-benzamide;

5-Bromo-3,4-difluoro-2-(4-iodo-2-methyl-phenylamino)-N-(3-methyl-but-2-enyloxy)-benzamide;

5-Bromo-3,4-difluoro-2-(4-iodo-2-methyl-phenylamino)-N-(3-methyl-pent-2-en-4-ynyloxy)-benzamide;

5-Bromo-3,4-difluoro-2-(4-iodo-2-methyl-benzyl)-N-[5-(3-methoxy-phenyl)-3-methyl-pent-2-en-4-ynyloxy]-benzamide;

5-Bromo-3,4-difluoro-2-(4-iodo-2-methyl-phenylamino)-N-(prop-2-ynyloxy)-benzamide;
5-Bromo-3,4-difluoro-2-(4-iodo-2-methyl-phenylamino)-N-[3-(3-methoxy-phenyl)-prop-2-ynyloxy]-benzamide;
5-Bromo-3,4-difluoro-2-(4-iodo-2-methyl-phenylamino)-N-(thiopen-2-ylmethoxy)-benzamide;
5-Bromo-3,4-difluoro-2-(4-iodo-2-methyl-phenylamino)-N-(pyridin-3-ylmethoxy)-benzamide;
5-Bromo-3-4-difluoro-2-(4-iodo-2-methyl-phenylamino)-N-(3-(2-fluorophenyl)-prop-2-ynyloxy)-benzamide;
5-Bromo-3,4-difluoro-2-(4-iodo-2-methyl-phenylamino)-N-(ethoxy)-benzamide;
5-Bromo-3,4-difluoro-2-(4-iodo-2-methyl-phenylamino)-N-(cyclopropylmethoxy)-benzamide;
5-Bromo-3,4-difluoro-2-(4-iodo-2-methyl-phenylamino)-N-(isopropoxy)-benzamide;
5-Bromo-3,4-difluoro-2-(4-iodo-2-methyl-phenylamino)-N-but-3-ynyloxy)-benzamide;
5-Chloro-N-hydroxy-2-(4-iodo-2-methyl-phenylamino)-benzamide;
5-Chloro-2-(4-iodo-2-methyl-phenylamino)-N-(tetrahydro-pyran-2-yloxy)-benzamide;
5-Chloro-2-(4-iodo-2-methyl-phenylamino)-N-methoxy-benzamide;
4-Bromo-2-(4-iodo-2-methyl-phenylamino)-N-phenylmethoxy-benzamide;
4-Fluoro-2-(4-iodo-2-methyl-phenylamino)-N-phenylmethoxy-benzamide;
5-Fluoro-N-hydroxy-2-(4-iodo-2-methyl-phenylamino)-benzamide;
5-Iodo-2-(4-iodo-2-methyl-phenylamino)-N-phenylmethoxy-benzamide;
5-Fluoro-2-(4-iodo-2-methyl-phenyl amino)-N-(tetrahydropyran-2-yloxy)-benzamide;
3,4-Difluoro-2-(4-bromo-2-methyl-phenylamino)-N-(3-phenylprop-2-ynyloxy)-benzamide;
3,4-Difluoro-2-(4-bromo-2-methyl-phenylamino)-N-(3-furylmethoxy)-benzamide;
3,4-Difluoro-2-(4-bromo-2-methyl-phenylamino)-N-(2-thienylmethoxy)-benzamide;
3,4-Difluoro-2-(4-bromo-2-methyl-phenylamino)-N-(but-3-ynyloxy)-benzamide;
3,4-Difluoro-2-(4-bromo-2-methyl-phenylamino)-N-(2-methyl-prop-2-enyloxy)-benzamide;
3,4-Difluoro-2-(4-bromo-2-methyl-phenylamino)-N-(but-2-enyloxy)-benzamide;
3,4-Difluoro-2-(4-bromo-2-methyl-phenylamino)-N-(methoxy)-benzamide;
3,4-Difluoro-2-(4-bromo-2-methyl-phenylamino)-N-(ethoxy)-benzamide;
3,4-Difluoro-2-(4-bromo-2-methyl-phenylamino)-N-(cyclobutoxy)-benzamide;
3,4-Difluoro-2-(4-bromo-2-methyl-phenylamino)-N-(isopropoxy)-benzamide;
3,4-Difluoro-2-(4-bromo-2-methyl-phenylamino)-N-(2-phenoxyethoxy)-benzamide;
3,4-Difluoro-2-(4-bromo-2-methyl-phenylamino)-N-(cyclopropylmethoxy)-benzamide;
3,4-Difluoro-2-(4-bromo-2-methyl-phenylamino)-N-(n-propoxy)-benzamide;
3,4-Difluoro-2-(4-bromo-2-methyl-phenylamino)-N-(1-methyl-prop-2-ynyloxy)-benzamide;
3,4-Difluoro-2-(4-bromo-2-methyl-phenylamino)-N-(3-(3-fluorophenyl)-prop-2-ynyloxy)-benzamide;
3,4-Difluoro-2-(4-bromo-2-methyl-phenylamino)-N-(4,4-dimethylpent-2-ynyloxy)-benzamide;
3,4-Difluoro-2-(4-bromo-2-methyl-phenylamino)-N-(cyclopentoxy)-benzamide;
3,4,5-Trifluoro-N-hydroxy-2-(4-iodo-2-methyl-phenylamino)-benzamide;
5-Chloro-3,4-difluoro-N-hydroxy-2-(4-iodo-2-methyl-phenylamino)-benzamide;
5-Bromo-3,4-difluoro-2-(2-fluoro-4-iodo-phenylamino)-N-hydroxy-benzamide;
N-Hydroxy-2-(4-iodo-2-methyl-phenylamino)-4-nitro-benzamide;
3,4,5-Trifluoro-2-(2-fluoro-4-iodo-phenylamino)-N-hydroxy-benzamide;
5-Chloro-3,4-difluoro-2-(2-fluoro-4-iodo-phenylamino)-N-hydroxy-benzamide;
5-Bromo-2-(2-chloro-4-iodo-phenylamino)-3,4-difluoro-N-hydroxy-benzamide;
2-(2-Fluoro-4-iodo-phenylamino)-N-hydroxy-4-nitro-benzamide;
2-(2-Chloro-4-iodo-phenylamino)-3,4,5-trifluoro-N-hydroxy-benzamide;
5-Chloro-2-(2-chloro-4-iodo-phenylamino)-3,4-difluoro-N-hydroxy-benzamide;
5-Bromo-2-(2-bromo-4-iodo-phenylamino)-3,4-difluoro-N-hydroxy-benzamide;
2-(2-Chloro-4-iodo-phenylamino)-N-hydroxy-4-methyl-benzamide;
2-(2-Bromo-4-iodo-phenylamino)-3,4,5-trifluoro-N-hydroxy-benzamide;
2-(2-Bromo-4-iodo-phenylamino)-5-chloro-3,4-difluoro-N-hydroxy-benzamide;
2-(2-Bromo-4-iodo-phenylamino)-N-hydroxy-4-nitro-benzamide;
4-Fluoro-2-(2-fluoro-4-iodo-phenylamino)-N-hydroxy-benzamide;
3,4-Difluoro-2-(2-fluoro-4-iodo-phenylamino)-N-hydroxy-benzamide;
2-(2-Chloro-4-iodo-phenylamino)-4-fluoro-N-hydroxy-benzamide;
2-(2-Chloro-4-iodo-phenylamino)-3,4-difluoro-N-hydroxy-benzamide;
2-(2-Bromo-4-iodo-phenylamino)-4-fluoro-N-hydroxy-benzamide;
2-(2-Bromo-4-iodo-phenylamino)-3,4-difluoro-N-hydroxy-benzamide;
N-Cyclopropylmethoxy-3,4,5-trifluoro-2-(4-iodo-2-methyl-phenylamino)-benzamide;
5-Chloro-N-cyclopropylmethoxy-3,4-difluoro-2-(4-iodo-2-methyl-phenylamino)-benzamide;
5-Bromo-N-cyclopropylmethoxy-3,4-difluoro-2-(2-fluoro-4-iodo-phenylamino)-benzamide;
N-Cyclopropylmethoxy-2-(4-iodo-2-methyl-phenylamino)-4-nitro-benzamide;
N-Cyclopropylmethoxy-3,4,5-trifluoro-2-(2-fluoro-4-iodo-phenylamino)-benzamide;
5-Chloro-N-cyclopropylmethoxy-3,4-difluoro-2-(2-fluoro-4-iodo-phenylamino)-benzamide;

5-Bromo-2-(2-chloro-4-iodo-phenylamino)-N-cyclopropylmethoxy-3,4-difluoro-benzamide;
N-Cyclopropylmethoxy-2-(2-fluoro-4-iodo-phenylamino)-4-nitro-benzamide;
2-(2-Chloro-4-iodo-phenylamino)-N-cyclopropylmethoxy-3,4,5-trifluoro-benzamide;
5-Chloro-2-(2-chloro-4-iodo-phenylamino)-N-cyclopropylmethoxy-3,4-difluoro-benzamide;
5-Bromo-2-(2-bromo-4-iodo-phenylamino)-N-ethoxy-3,4-difluoro-benzamide;
2-(2-Chloro-4-iodo-phenylamino)-N-ethoxy-4-nitro-benzamide;
2-(2-Bromo-4-iodo-phenylamino)-N-cyclopropylmethoxy-3,4,5-trifluoro-benzamide;
2-(2-Bromo-4-iodo-phenylamino)-5-chloro-N-cyclopropylmethoxy-3,4-difluoro-benzamide;
2-(2-Bromo-4-iodo-phenylamino)-N-cyclopropylmethoxy-4-nitro-benzamide;
N-Cyclopropylmethoxy-4-fluoro-2-(2-fluoro-4-iodo-phenylamino)-benzamide;
N-Cyclopropylmethoxy-3,4-difluoro-2-(2-fluoro-4-iodo-phenylamino)-benzamide;
2-(2-Chloro-4-iodo-phenylamino)-N-cyclopropylmethoxy-4-fluoro-benzamide;
2-(2-Chloro-4-iodo-phenylamino)-N-cyclopropylmethoxy-3,4-difluoro-benzamide;
2-(2-Bromo-4-iodo-phenylamino)-N-cyclopropylmethoxy-4-fluoro-benzamide; or
2-(2-Bromo-4-iodo-phenylamino)-N-cyclopropylmethoxy-3,4-difluoro-benzamide.

13. The method of claim 1, wherein the MEK inhibitor is a compound of Formula III:

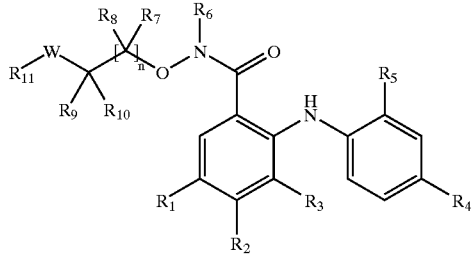

III wherein $R_1$ is hydrogen, halogen, or nitro;

$R_2$ is hydrogen or fluorine;

$R_3$ is hydrogen or fluorine;

$R_4$ is hydrogen, iodine, bromine, chlorine, or fluorine;

$R_5$ is hydrogen, halogen, hydroxy, $C_{1-8}$ alkyl, $C_{1-8}$ alkoxy, trifluoromethyl, or cyano;

n is 1 to 5;

$R_6$, $R_7$, $R_8$, $R_9$, and $R_{10}$ are independently hydrogen, $C_{1-8}$ alkyl, $C_{3-8}$ cycloalkyl, hydroxy, $C_{1-8}$ alkoxy, perhalo$(C_{1-3})$alkyl, hydroxy$(C_{1-8})$alkyl, $(C_{1-5})$alkoxy$(C_{1-5})$alkyl, $[(C_{1-4})$alkyl$]_2$aminomethyl, $(C_{2-7})$heterocycle$(C_{1-5})$alkyl, or aryloxy$(C_{1-5})$alkyl, or may be independently joined to complete a 3–10 member cyclic ring optionally containing additional heteroatoms selected from the group consisting of O, S, NH, and N-alkyl, wherein $R_7$ and $R_8$ are independently selected for n>1;

Ra and Rb are independently hydrogen or $C_{1-4}$ alkyl;

W is O or NRa;

$R_{11}$ is hydrogen, $C_{1-8}$ alkyl, $C_{2-6}$ alkenyl, $C_{3-8}$ cycloalkyl, hydroxy$(C_{1-8})$alkyl, $(C_{1-5})$alkoxy$(C_{1-5})$alkyl, phenyl, $C_{2-7}$ heteroaryl, $(C_{1-8})$alkylcarbonyl, (phenyl)carbonyl, (phenyl)$(C_{1-3}$alkyl)carbonyl, or trifluoro$(C_{1-6})$alkyl;

wherein the above alkyl, alkoxy, cycloalkyl, heteroaryl, and phenyl groups can be optionally substituted with between 1 and 5 substituents independently selected from the group consisting of hydroxy, amino, monoalkylamino, dialkylamino, halogen, cyano, $(C_{1-3})$ alkoxy, COOR, OCORa, CONRaRb, NRaCORb, SO, $SO_2$, $SO_4$, and $SO_2$NRaRb;

and pharmaceutically acceptable salts;

provided that when $R_{11}$ is phenyl and n is 1, W cannot be O;

further provided that the compound is not
5-Bromo-N-(2-diethylamino-ethoxy)-3,4-difluoro-(4-iodo-2-methyl-phenylamino)-benzamide;
5-Bromo-N-(2-dimethylamino-propoxy)-3,4-difluoro-2-(4-iodo-2-methyl-phenylamino)-benzamide; or
5-Bromo-2-(2-chloro-4-iodo-phenylamino)-N-(2-dimethylamino-ethoxy)-3,4-difluoro-benzamide.

14. The method according to claim 1, wherein the MEK inhibitor comprises
3,4,5-Trifluoro-N-(2-hydroxy-ethoxy)-2-(4-iodo-2-methyl-phenylamino)-benzamide;
3,4-Difluoro-N-(2-hydroxy-ethoxy)-2-(4-iodo-2-methyl-phenylamino)-benzamide;
2-(2-Chloro-4-iodo-phenylamino)-3,4-fluoro-N-(2-hydroxy-ethoxy)-benzamide;
2-(2-Chloro-4-iodo-phenylamino)-4-fluoro-N-(2-hydroxy-ethoxy)-benzamide;
4-Fluoro-N-(2-hydroxy-ethoxy)-2-(4-iodo-2-methyl-phenylamino)-benzamide;
2-(2-Chloro-4-iodo-phenylamino)-3,4,5-trifluoro-N-(2-hydroxy-ethoxy)-benzamide;
5-Chloro-3,4-difluoro-N-(2-hydroxy-ethoxy)-2-(4-iodo-phenylamino)-benzamide;
4-Fluoro-2-(2-fluoro-4-iodo-phenylamino)-N-(2-hydroxy-ethoxy)-benzamide;
3,4-Difluoro-2-(2-fluoro-4-iodo-phenylamino)-N-(2-hydroxy-ethoxy)-benzamide;
5-Chloro-3,4-difluoro-2-(2-fluoro-4-iodo-phenylamino)-N-(2-hydroxy-ethoxy)-benzamide;
5-Bromo-3,4-difluoro-2-(2-fluoro-4-iodo-phenylamino)-N-(2-hydroxy-ethoxy)-benzamide;
4,5-Difluoro-N-(2-hydroxy-ethoxy)-2-(4-iodo-2-methyl-phenylamino)-benzamide;
5-Bromo-3,4-difluoro-N-(2-hydroxy-ethoxy)-2-(4-iodo-2-methyl-phenylamino)-benzamide;
5-Bromo-2-(2-chloro-4-iodo-phenylamino)-3,4-difluoro-N-(2-hydroxy-ethoxy)-benzamide;
5-Chloro-3,4-difluoro-N-(2-hydroxy-ethoxy)-2-(4-iodo-2-methyl-phenylamino)-benzamide;
5-Bromo-4-fluoro-N-(2-hydroxy-ethoxy)-2-(4-iodo-2-methyl-phenylamino)-benzamide;
2-(2-Chloro-4-iodo-phenylamino)-4,5-difluoro-N-(2-hydroxy-ethoxy)-benzamide;
4,5-Difluoro-2-(2-fluoro-4-iodo-phenylamino)-N-(2-hydroxy-ethoxy)-benzamide;
5-Bromo-4-fluoro-2-(2-fluoro-4-iodo-phenylamino)-N-(2-hydroxy-ethoxy)-benzamide;
5-Chloro-2-(2-chloro-4-iodo-phenylamino)-3,4-difluoro-N-(2-hydroxy-ethoxy)-benzamide;

3,4,5-Trifluoro-2-(2-fluoro-4-iodo-phenylamino)-N-(2-hydroxy-ethoxy)-benzamide;
2-(4-Bromo-2-fluoro-phenylamino)-3,4-difluoro-N-(2-hydroxy-ethoxy)-benzamide;
2-(4-Bromo-2-fluoro-phenylamino)-4,5-difluoro-N-(2-hydroxy-ethoxy)-benzamide;
2-(4-Chloro-2-fluoro-phenylamino)-3,4-difluoro-N-(2-hydroxy-ethoxy)-benzamide;
3,4-Difluoro-2-(2-fluoro-phenylamino)-N-(2-hydroxy-ethoxy)-benzamide;
5-Chloro-2-(2,4-difluoro-phenylamino)-3,4-difluoro-N-(2-hydroxy-ethoxy)-benzamide;
2-(2,4-Difluoro-phenylamino)-3,4-difluoro-N-(2-hydroxy-ethoxy)-benzamide;
4-Fluoro-N-(3-hydroxy-propoxy)-2-(4-iodo-2-methyl-phenylamino)-benzamide;
5-Chloro-3,4-difluoro-N-(3-hydroxy-propoxy)-2-(4-iodo-2-methyl-phenylamino)-benzamide;
2-(2-Chloro-4-iodo-phenylamino)-4-fluoro-N-(3-hydroxy-propoxy)-benzamide;
5-Bromo-2-(2-chloro-4-iodo-phenylamino)-3,4-difluoro-N-(3-hydroxy-propoxy)-benzamide;
3,4-Difluoro-2-(2-fluoro-4-iodo-phenylamino)-N-(3-hydroxy-propoxy)-benzamide;
3,4-Difluoro-2-(2-fluoro-4-iodo-phenylamino)-N-(4-hydroxy-butoxy)-benzamide;
5-Chloro-2-(2-chloro-4-iodo-phenylamino)-N-(2,3-dihydroxy-propoxy)-3,4-difluoro-benzamide;
5-Chloro-N-(2,3-dihydroxy-propoxy)-3,4-difluoro-2-(4-iodo-2-methyl-phenylamino)-benzamide;
5-Chloro-N-(3,4-dihydroxy-butoxy)-3,4-difluoro-2-(4-iodo-2-methyl-phenylamino)-benzamide;
5-Chloro-2-(2-chloro-4-iodo-phenylamino)-N-(3,4-dihydroxy-butoxy)-3,4-difluoro-benzamide;
N-(2,2-Dimethyl-1,3-dioxolan-4-ylmethoxy)-3,4-difluoro-2-(2-fluoro-4-iodo-phenylamino)-benzamide;
N-(2,3-Dihydroxy-propoxy)-3,4-difluoro-2-(2-fluoro-4-iodo-phenylamino)-benzamide;
5-Bromo-N-(2,3-dihydroxy-propoxy)-3,4-difluoro-2-(2-fluoro-4-iodo-phenylamino)-benzamide;
5-Chloro-N-(2,3-dihydroxy-propoxy)-3,4-difluoro-2-(2-fluoro-4-iodo-phenylamino)-benzamide;
2-N-(2,3-Dihydroxy-propoxy)-4-fluoro-2-(2-fluoro-4-iodo-phenylamino)-benzamide;
N-(2,3-Dihydroxy-propoxy)-3,4,5-trifluoro-2-(2-fluoro-4-iodo-phenylamino)-benzamide;
2-(4-Bromo-2-fluoro-phenylamino)-N-(2,3-dihydroxy-propoxy)-3,4-difluoro-benzamide;
2-(4-Chloro-2-fluoro-phenylamino)-N-(2,3-dihydroxy-propoxy)-3,4-difluoro-benzamide;
N-(2,2-Dimethyl-1,3-dioxinan-5-yloxy)-3,4-difluoro-2-(2-fluoro-4-iodo-phenylamino)-benzamide;
3,4-Difluoro-2-(2-fluoro-4-iodo-phenylamino)-N-(2-hydroxy-1-hydroxymethyl-ethoxy)-benzamide;
5-Chloro-3,4-difluoro-2-(2-fluoro-4-iodo-phenylamino)-N-(2-hydroxy-1-hydroxymethyl-ethoxy)-benzamide;
N-((R)-2,3-Dihydroxy-propoxy)-3,4-difluoro-2-(2-fluoro-4-iodo-phenylamino)-benzamide;
N-((S)-2,3-Dihydroxy-propoxy)-3,4-difluoro-2-(2-fluoro-4-iodo-phenylamino)-benzamide;
5-Chloro-2-(2-chloro-4-iodo-phenylamino)-N-((R)-2,3-dihydroxy-propoxy)-3,4-difluoro-benzamide;
5-Chloro-2-(2-chloro-4-iodo-phenylamino)-N-((S)-2,3-dihydroxy-propoxy)-3,4-difluoro-benzamide;
5-Chloro-N-((R)-2,3-dihydroxy-propoxy)-3,4-difluoro-2-(2-fluoro-4-iodo-phenylamino)-benzamide;
5-Chloro-N-((S) 2,3-dihydroxy-propoxy)-3,4-difluoro-2-(2-fluoro-4-iodo-phenylamino)-benzamide;
2-(4-Bromo-2-fluoro-phenylamino)-N-((R)-2,3-dihydroxy-propoxy)-3,4-difluoro-benzamide;
2-(2-Chloro-4-iodo-phenylamino)-3,4-difluoro-N-(2-vinyloxy-ethoxy)-benzamide;
2-(2-Chloro-4-iodo-phenylamino)-3,4,5-trifluoro-N-(2-vinyloxy-ethoxy)-benzamide;
4-Fluoro-2-(2-fluoro-4-iodo-phenylamino)-N-(2-vinyloxy-ethoxy)-benzamide;
3,4-Difluoro-2-(2-fluoro-4-iodo-phenylamino)-N-(2-vinyloxy-ethoxy)-benzamide;
5-Chloro-3,4-difluoro-2-(2-fluoro-4-iodo-phenylamino)-N-(2-vinyloxy-ethoxy)-benzamide;
5-Bromo-3,4-difluoro-2-(2-fluoro-4-iodo-phenylamino)-N-(2-vinyloxy-ethoxy)-benzamide;
5-Bromo-2-(2-chloro-4-iodo-phenylamino)-3,4-difluoro-N-(2-hydroxy-1,1-dimethyl-ethoxy)-benzamide;
3,4-Difluoro-N-(2-hydroxy-1,1-dimethyl-ethoxy)-2-(4-iodo-2-methyl-phenylamino)-benzamide;
2-(2-Chloro-4-iodo-phenylamino)-3,4-difluoro-N-(2-hydroxy-2-methyl-propoxy)-benzamide;
3,4-Difluoro-2-(2-fluoro-4-iodo-phenylamino)-N-(2-hydroxy-1,1-dimethyl-ethoxy)-benzamide;
5-Chloro-3,4-difluoro-2-(2-fluoro-4-iodo-phenylamino)-N-(2-hydroxy-1,1-dimethyl-ethoxy)-benzamide;
3,4-Difluoro-2-(2-fluoro-4-iodo-phenylamino)-N-(2-hydroxy-2-methyl-propoxy)-benzamide;
3,4-Difluoro-N-(2-hydroxy-3-methoxy-propoxy)-2-(4-iodo-2-methyl-phenylamino)-benzamide;
5-Bromo-2-(2-chloro-4-iodo-phenylamino)-3,4-difluoro-N-(2-hydroxy-3-methoxy-propoxy)-benzamide;
3,4-Difluoro-N-(1-hydroxymethyl-cyclopropylmethoxy)-2-(4-iodo-2-methyl-phenylamino)-benzamide;
5-Bromo-2-(2-chloro-4-iodo-phenylamino)-3,4-difluoro-N-(1-hydroxymethyl-cyclopropylmethoxy)-benzamide;
3,4-Difluoro-2-(4-iodo-2-methyl-phenylamino)-N-(3,3,3-trifluoro-2-hydroxy-propoxy)-benzamide;
5-Bromo-2-(2-chloro-4-iodo-phenylamino)-3,4-difluoro-N-(3,3,3-trifluoro-2-hydroxy-propoxy)-benzamide;
3,4-Difluoro-2-(2-fluoro-4-iodo-phenylamino)-N-(2-hydroxymethyl-cyclopropylmethoxy)-benzamide;
5-Chloro-3,4-difluoro-2-(2-fluoro-4-iodo-phenylamino)-N-(2-hydroxymethyl-cyclopropylmethoxy)-benzamide;
N-(2,3-Dihydroxy-3-methyl-butoxy)-3,4-difluoro-2-(2-fluoro-4-iodo-phenylamino)-benzamide;
2-(2-Chloro-4-iodo-phenylamino)-3,4-difluoro-N-(2-phenylamino-ethoxy)-benzamide;
3,4-Difluoro-2-(4-iodo-2-methyl-phenylamino)-N-(2-methylamino-ethoxy)-benzamide;
3,4-Difluoro-2-(2-fluoro-4-iodo-phenylamino)-N-(2-methylamino-ethoxy)-benzamide; hydrochloride;
3,4-Difluoro-2-(4-iodo-2-methyl-phenylamino)-N-[2-(2,2,2-trifluoro-ethylamino)-ethoxy]-benzamide; hydrochloride;
2-(2-Chloro-4-iodo-phenylamino)-4-fluoro-N-(2-hydroxy-ethoxy)-N-methyl-benzamide;

Acetic acid 2-[3,4,5-trifluoro-2-(4-iodo-2-methyl-phenylamino)-benzoylaminooxy]-ethyl ester;
[3,4-Difluoro-2-(2-fluoro-4-iodo-phenylamino)-phenyl]-(4-hydroxy-isoxazolidin-2-yl)-methanone;
5-Bromo-N-(2,3-dihydroxy-propoxy)-3,4-difluoro-2-(2-fluoro-phenylamino)-benzamide;
N-(2,3-Dihydroxy-propoxy)-3,4-difluoro-2-(2-fluoro-phenylamino)-benzamide;
2-(2-Chloro-4-iodo-phenylamino)-N-(2,3-dihydroxy-propoxy)-3,4-difluoro-benzamide;
2-(2-Chloro-4-iodo-phenylamino)-N-(2,3-dihydroxy-propoxy)-3,4,5-trifluoro-benzamide;
5-Bromo-2-(2-chloro-4-iodo-phenylamino)-N-(2,3-dihydroxy-propoxy)-3,4-difluoro-benzamide;
N-(2,3-Dihydroxy-propoxy)-3,4-difluoro-2-(4-iodo-2-methyl-phenylamino)-benzamide;
N-(2,3-Dihydroxy-propoxy)-3,4,5-trifluoro-2-(4-iodo-2-methyl-phenylamino)-benzamide;
5-Bromo-N-(2,3-dihydroxy-propoxy)-3,4-difluoro-2-(4-iodo-2-methyl-phenylamino)-benzamide;
2-(2-Chloro-4-iodo-phenylamino)-N-(3,4-dihydroxy-butoxy)-3,4-difluoro-benzamide;
2-(2-Chloro-4-iodo-phenylamino)-N-(3,4-dihydroxy-butoxy)-3,4,5-trifluoro-benzamide;
5-Bromo-2-(2-chloro-4-iodo-phenylamino)-N-(3,4-dihydroxy-butoxy)-3,4-difluoro-benzamide;
N-(3,4-Dihydroxy-butoxy)-3,4-difluoro-2-(4-iodo-2-methyl-phenylamino)-benzamide;
N-(3,4-Dihydroxy-butoxy)-3,4,5-trifluoro-2-(4-iodo-2-methyl-phenylamino)-benzamide;
5-Bromo-N-(3,4-dihydroxy-butoxy)-3,4-difluoro-2-(4-iodo-2-methyl-phenylamino)-benzamide;
5-Bromo-2-(2-chloro-4-iodo-phenylamino)-3,4-difluoro-N-(3-hydroxy-propoxy)-benzamide;
2-(2-Chloro-4-iodo-phenylamino)-3,4-difluoro-N-(3-hydroxy-propoxy)-benzamide;
3,4,5-Trifluoro-N-(3-hydroxy-propoxy)-2-(4-iodo-2-methyl-phenylamino)-benzamide;
2-(2-Chloro-4-iodo-phenylamino)-3,4,5-trifluoro-N-(3-hydroxy-propoxy)-benzamide;
5-Bromo-3,4-difluoro-N-(3-hydroxy-propoxy)-2-(4-iodo-2-methyl-phenylamino)-benzamide;
3,4-Difluoro-N-(3-hydroxy-propoxy)-2-(4-iodo-2-methyl-phenylamino)-benzamide;
2-(2-Chloro-4-iodo-phenylamino)-3,4-difluoro-N-(2-hydroxy-butoxy)-benzamide;
2-(2-Chloro-4-iodo-phenylamino)-3,4,5-trifluoro-N-(2-hydroxy-butoxy)-benzamide;
3,4,5-Trifluoro-N-(2-hydroxy-butoxy)-2-(4-iodo-2-methyl-phenylamino)-benzamide;
5-Bromo-2-(2-chloro-4-iodo-phenylamino)-3,4-difluoro-N-(2-hydroxy-butoxy)-benzamide;
5-Bromo-3,4-difluoro-N-(2-hydroxy-butoxy)-2-(4-iodo-2-methyl-phenylamino)-benzamide;
3,4-Difluoro-N-(2-hydroxy-butoxy)-2-(4-iodo-2-methyl-phenylamino)-benzamide;
5-Chloro-2-(2-chloro-4-iodo-phenylamino)-3,4-difluoro-N-(2-hydroxy-butoxy)-benzamide;
5-Chloro-3,4-difluoro-N-(2-hydroxy-butoxy)-2-(4-iodo-2-methyl-phenylamino)-benzamide;
3,4-Difluoro-2-(2-fluoro-4-iodo-phenylamino)-N-(2-hydroxy-butoxy)-benzamide;
5-Bromo-3,4-difluoro-2-(2-fluoro-4-iodo-phenylamino)-N-(2-hydroxy-butoxy)-benzamide;
5-Chloro-3,4-difluoro-2-(2-fluoro-4-iodo-phenylamino)-N-(2-hydroxy-butoxy)-benzamide;
4,5-Difluoro-2-(2-fluoro-4-iodo-phenylamino)-N-(2-hydroxy-butoxy)-benzamide;
5-Chloro-2-(2,4-difluoro-phenylamino)-3,4-difluoro-N-(2-hydroxy-butoxy)-benzamide;
2-(2,4-Difluoro-phenylamino)-3,4-difluoro-N-(2-hydroxy-butoxy)-benzamide;
2-(4-Bromo-2-fluoro-phenylamino)-3,4-difluoro-N-(2-hydroxy-butoxy)-benzamide;
5-Chloro-3,4-difluoro-N-(2-hydroxy-1-methyl-ethoxy)-2-(4-iodo-2-methyl-phenylamino)-benzamide;
2-(2-Chloro-4-iodo-phenylamino)-3,4-difluoro-N-(2-hydroxy-1-methyl-ethoxy)-benzamide;
2-(2-Chloro-4-iodo-phenylamino)-3,4,5-trifluoro-N-(2-hydroxy-1-methyl-ethoxy)-benzamide;
3,4,5-Trifluoro-N-(2-hydroxy-1-methyl-ethoxy)-2-(4-iodo-2-methyl-phenylamino)-benzamide;
5-Bromo-2-(2-chloro-4-iodo-phenylamino)-3,4-difluoro-N-(2-hydroxy-1-methyl-ethoxy)-benzamide;
5-Bromo-3,4-difluoro-N-(2-hydroxy-1-methyl-ethoxy)-2-(4-iodo-2-methyl-phenylamino)-benzamide;
2-(4-Chloro-2-fluoro-phenylamino)-3,4-difluoro-N-(2-hydroxy-1-methyl-ethoxy)-benzamide;
3,4-Difluoro-N-(2-hydroxy-1-methyl-ethoxy)-2-(4-iodo-2-methyl-phenylamino)-benzamide;
5-Chloro-2-(2-chloro-4-iodo-phenylamino)-3,4-difluoro-N-(2-hydroxy-1-methyl-ethoxy)-benzamide;
3,4-Difluoro-2-(2-fluoro-4-iodo-phenylamino)-N-(2-hydroxy-1-methyl-ethoxy)-benzamide;
5-Bromo-3,4-difluoro-2-(2-fluoro-4-iodo-phenylamino)-N-(2-hydroxy-1-methyl-ethoxy)-benzamide;
5-Chloro-3,4-difluoro-2-(2-fluoro-4-iodo-phenylamino)-N-(2-hydroxy-1-methyl-ethoxy)-benzamide;
4,5-Difluoro-2-(2-fluoro-4-iodo-phenylamino)-N-(2-hydroxy-1-methyl-ethoxy)-benzamide;
5-Chloro-2-(2,4-difluoro-phenylamino)-3,4-difluoro-N-(2-hydroxy-1-methyl-ethoxy)-benzamide;
2-(2,4-Difluoro-phenylamino)-3,4-difluoro-N-(2-hydroxy-1-methyl-ethoxy)-benzamide;
2-(2-Chloro-4-iodo-phenylamino)-3,4-difluoro-N-(2-methoxy-ethoxy)-benzamide;
2-(2-Chloro-4-iodo-phenylamino)-3,4,5-trifluoro-N-(2-methoxy-ethoxy)-benzamide;
3,4-Difluoro-2-(4-iodo-2-methyl-phenylamino)-N-(2-methoxy-ethoxy)-benzamide;
5-Bromo-3,4-difluoro-2-(4-iodo-2-methyl-phenylamino)-N-(2-methoxy-ethoxy)-benzamide;
3,4,5-Trifluoro-2-(4-iodo-2-methyl-phenylamino)-N-(2-methoxy-ethoxy)-benzamide;
5-Bromo-2-(2-chloro-4-iodo-phenylamino)-3,4-difluoro-N-(2-methoxy-ethoxy)-benzamide;
5-Chloro-2-(2-chloro-4-iodo-phenylamino)-3,4-difluoro-N-(2-methoxy-ethoxy)-benzamide;
5-Chloro-3,4-difluoro-2-(4-iodo-2-methyl-phenylamino)-N-(2-methoxy-ethoxy)-benzamide;
5-Chloro-3,4-difluoro-2-(2-fluoro-4-iodo-phenylamino)-N-(2-methoxy-ethoxy)-benzamide;
2-(2-Chloro-4-iodo-phenylamino)-3,4-difluoro-N-(2-hydroxy-3-morpholin-4-yl-propoxy)-benzamide;

5-Bromo-2-(2-chloro-4-iodo-phenylamino)-3,4-difluoro-N-(2-hydroxy-3-morpholin-4-yl-propoxy)-benzamide;
2-(2-Chloro-4-iodo-phenylamino)-3,4,5-trifluoro-N-(2-hydroxy-3-morpholin-4-yl-propoxy)-benzamide;
3,4,5-Trifluoro-N-(2-hydroxy-3-morpholin-4-yl-propoxy)-2-(4-iodo-2-methyl-phenylamino)-benzamide;
5-Bromo-3,4-difluoro-N-(2-hydroxy-3-morpholin-4-yl-propoxy)-2-(4-iodo-2-methyl-phenylamino)-benzamide;
3,4-Difluoro-N-(2-hydroxy-3-morpholin-4-yl-propoxy)-2-(4-iodo-2-methyl-phenylamino)-benzamide;
5-Chloro-2-(2-chloro-4-iodo-phenylamino)-3,4-difluoro-N-(2-hydroxy-3-morpholin-4-yl-propoxy)-benzamide;
5-Chloro-3,4-difluoro-N-(2-hydroxy-3-morpholin-4-yl-propoxy)-2-(4-iodo-2-methyl-phenylamino)-benzamide;
3,4-Difluoro-2-(2-fluoro-4-iodo-phenylamino)-N-(2-hydroxy-3-morpholin-4-yl-propoxy)-benzamide;
5-Chloro-3,4-difluoro-2-(2-fluoro-4-iodo-phenylamino)-N-(2-hydroxy-3-morpholin-4-yl-propoxy)-benzamide;
4,5-Difluoro-2-(2-fluoro-4-iodo-phenylamino)-N-(2-hydroxy-3-morpholin-4-yl-propoxy)-benzamide;
5-Chloro-2-(2,4-difluoro-phenylamino)-3,4-difluoro-N-(2-hydroxy-3-morpholin-4-yl-propoxy)-benzamide;
2-(4-Chloro-2-fluoro-phenylamino)-3,4-difluoro-N-(2-hydroxy-3-morpholin-4-yl-propoxy)-benzamide;
2-(2-Chloro-4-iodo-phenylamino)-3,4-difluoro-N-(2-hydroxy-propoxy)-benzamide;
3,4,5-Trifluoro-N-(2-hydroxy-propoxy)-2-(4-iodo-2-methyl-phenylamino)-benzamide;
5-Bromo-2-(2-chloro-4-iodo-phenylamino)-3,4-difluoro-N-(2-hydroxy-propoxy)-benzamide;
5-Bromo-3,4-difluoro-N-(2-hydroxy-propoxy)-2-(4-iodo-2-methyl-phenylamino)-benzamide;
2-(2-Chloro-4-iodo-phenylamino)-3,4,5-trifluoro-N-(2-hydroxy-propoxy)-benzamide;
5-Chloro-2-(2-chloro-4-iodo-phenylamino)-3,4-difluoro-N-(2-hydroxy-propoxy)-benzamide;
3,4-Difluoro-N-(2-hydroxy-propoxy)-2-(4-iodo-2-methyl-phenylamino)-benzamide;
5-Chloro-3,4-difluoro-N-(2-hydroxy-propoxy)-2-(4-iodo-2-methyl-phenylamino)-benzamide;
3,4-Difluoro-2-(2-fluoro-4-iodo-phenylamino)-N-(2-hydroxy-propoxy)-benzamide;
5-Chloro-3,4-difluoro-2-(2-fluoro-4-iodo-phenylamino)-N-(2-hydroxy-propoxy)-benzamide;
5-Chloro-2-(2,4-difluoro-phenylamino)-3,4-difluoro-N-(2-hydroxy-propoxy)-benzamide;
2-(2,4-Difluoro-phenylamino)-3,4-difluoro-N-(2-hydroxy-propoxy)-benzamide;
2-(4-Chloro-2-fluoro-phenylamino)-3,4-difluoro-N-(2-hydroxy-propoxy)-benzamide;
4,5-Difluoro-2-(2-fluoro-4-iodo-phenylamino)-N-(2-hydroxy-propoxy)-benzamide;
2-(2-Chloro-4-iodo-phenylamino)-3,4,5-trifluoro-N-(2-hydroxy-2-methyl-propoxy)-benzamide;
3,4,5-Trifluoro-N-(2-hydroxy-2-methyl-propoxy)-2-(4-iodo-2-methyl-phenylamino)-benzamide;
5-Bromo-3,4-difluoro-N-(2-hydroxy-2-methyl-propoxy)-2-(4-iodo-2-methyl-phenylamino)-benzamide;
5-Bromo-2-(2-chloro-4-iodo-phenylamino)-3,4-difluoro-N-(2-hydroxy-2-methyl-propoxy)-benzamide;
3,4-Difluoro-N-(2-hydroxy-2-methyl-propoxy)-2-(4-iodo-2-methyl-phenylamino)-benzamide;
5-Chloro-2-(2-chloro-4-iodo-phenylamino)-3,4-difluoro-N-(2-hydroxy-2-methyl-propoxy)-benzamide;
5-Chloro-3,4-difluoro-N-(2-hydroxy-2-methyl-propoxy)-2-(4-iodo-2-methyl-phenylamino)-benzamide;
3,4-Difluoro-2-(2-fluoro-4-iodo-phenylamino)-N-(2-hydroxy-2-methyl-propoxy)-benzamide;
5-Bromo-3,4-difluoro-2-(2-fluoro-4-iodo-phenylamino)-N-(2-hydroxy-2-methyl-propoxy)-benzamide;
5-Chloro-3,4-difluoro-2-(2-fluoro-4-iodo-phenylamino)-N-(2-hydroxy-2-methyl-propoxy)-benzamide;
5-Chloro-2-(2,4-difluoro-phenylamino)-3,4-difluoro-N-(2-hydroxy-2-methyl-propoxy)-benzamide;
2-(2,4-Difluoro-phenylamino)-3,4-difluoro-N-(2-hydroxy-2-methyl-propoxy)-benzamide;
2-(4-Bromo-2-fluoro-phenylamino)-3,4-difluoro-N-(2-hydroxy-2-methyl-propoxy)-benzamide;
2-(2-Chloro-4-iodo-phenylamino)-3,4-difluoro-N-(2-hydroxy-3-phenoxy-propoxy)-benzamide;
2-(2-Chloro-4-iodo-phenylamino)-3,4,5-trifluoro-N-(2-hydroxy-3-phenoxy-propoxy)-benzamide;
3,4,5-Trifluoro-N-(2-hydroxy-3-phenoxy-propoxy)-2-(4-iodo-2-methyl-phenylamino)-benzamide;
5-Bromo-2-(2-chloro-4-iodo-phenylamino)-3,4-difluoro-N-(2-hydroxy-3-phenoxy-propoxy)-benzamide;
5-Bromo-3,4-difluoro-N-(2-hydroxy-3-phenoxy-propoxy)-2-(4-iodo-2-methyl-phenylamino)-benzamide;
3,4-Difluoro-N-(2-hydroxy-3-phenoxy-propoxy)-2-(4-iodo-2-methyl-phenylamino)-benzamide;
5-Chloro-2-(2-chloro-4-iodo-phenylamino)-3,4-difluoro-N-(2-hydroxy-3-phenoxy-propoxy)-benzamide;
5-Chloro-3,4-difluoro-N-(2-hydroxy-3-phenoxy-propoxy)-2-(4-iodo-2-methyl-phenylamino)-benzamide;
3,4-Difluoro-2-(2-fluoro-4-iodo-phenylamino)-N-(2-hydroxy-3-phenoxy-propoxy)-benzamide;
5-Chloro-3,4-difluoro-2-(2-fluoro-4-iodo-phenylamino)-N-(2-hydroxy-3-phenoxy-propoxy)-benzamide;
4,5-Difluoro-2-(2-fluoro-4-iodo-phenylamino)-N-(2-hydroxy-3-phenoxy-propoxy)-benzamide;
5-Chloro-2-(2,4-difluoro-phenylamino)-3,4-difluoro-N-(2-hydroxy-3-phenoxy-propoxy)-benzamide;
2-(2,4-Difluoro-phenylamino)-3,4-difluoro-N-(2-hydroxy-3-phenoxy-propoxy)-benzamide;
2-(4-Chloro-2-fluoro-phenylamino)-3,4-difluoro-N-(2-hydroxy-3-phenoxy-propoxy)-benzamide;
3,4-Difluoro-N-(3-hydroxy-2,2-dimethyl-propoxy)-2-(4-iodo-2-methyl-phenylamino)-benzamide;
2-(2-Chloro-4-iodo-phenylamino)-3,4,5-trifluoro-N-(3-hydroxy-2,2-dimethyl-propoxy)-benzamide;
3,4,5-Trifluoro-N-(3-hydroxy-2,2-dimethyl-propoxy)-2-(4-iodo-2-methyl-phenylamino)-benzamide;
5-Chloro-2-(2-chloro-4-iodo-phenylamino)-3,4-difluoro-N-(3-hydroxy-2,2-dimethyl-propoxy)-benzamide;
5-Chloro-3,4-difluoro-N-(3-hydroxy-2,2-dimethyl-propoxy)-2-(4-iodo-2-methyl-phenylamino)-benzamide;
3,4-Difluoro-2-(2-fluoro-4-iodo-phenylamino)-N-(3-hydroxy-2,2-dimethyl-propoxy)-benzamide;
5-Chloro-2-(2,4-difluoro-phenylamino)-3,4-difluoro-N-(3-hydroxy-2,2-dimethyl-propoxy)-benzamide;

3,4-Difluoro-2-(4-iodo-2-methyl-phenylamino)-N-[2-(2-methoxy-ethoxy)-ethoxy]-benzamide;
3,4,5-Trifluoro-2-(4-iodo-2-methyl-phenylamino)-N-[2-(2-methoxy-ethoxy)-ethoxy]-benzamide;
5-Bromo-3,4-difluoro-2-(4-iodo-2-methyl-phenylamino)-N-[2-(2-methoxy-ethoxy)-ethoxy]-benzamide;
2-(2-Chloro-4-iodo-phenylamino)-3,4-difluoro-N-[2-(2-methoxy-ethoxy)-ethoxy]-benzamide;
2-(2-Chloro-4-iodo-phenylamino)-3,4,5-trifluoro-N-[2-(2-methoxy-ethoxy)-ethoxy]-benzamide;
5-Bromo-2-(2-chloro-4-iodo-phenylamino)-3,4-difluoro-N-[2-(2-methoxy-ethoxy)-ethoxy]-benzamide;
3,4,5-Trifluoro-2-(2-fluoro-4-iodo-phenylamino)-N-(3,3,3-trifluoro-2-hydroxy-propoxy)-benzamide;
5-Chloro-2-(2,4-difluoro-phenylamino)-3,4-difluoro-N-(3,3,3-trifluoro-2-hydroxy-propoxy)-benzamide;
2-(2,4-Difluoro-phenylamino)-3,4-difluoro-N-(3,3,3-trifluoro-2-hydroxy-propoxy)-benzamide;
2-(4-Chloro-2-fluoro-phenylamino)-3,4-difluoro-N-(3,3,3-trifluoro-2-hydroxy-propoxy)-benzamide;
5-Chloro-2-(2,4-difluoro-phenylamino)-3,4-difluoro-N-(2-hydroxymethyl-cyclopropylmethoxy)-benzamide;
2-(2,4-Difluoro-phenylamino)-3,4-difluoro-N-(2-hydroxymethyl-cyclopropylmethoxy)-benzamide;
2-(4-Chloro-2-fluoro-phenylamino)-3,4-difluoro-N-(2-hydroxymethyl-cyclopropylmethoxy)-benzamide;
4,5-Difluoro-2-(2-fluoro-4-iodo-phenylamino)-N-(2-hydroxymethyl-cyclopropylmethoxy)-benzamide;
3,4-Difluoro-2-(2-fluoro-4-iodo-phenylamino)-N-(1-hydroxymethyl-cyclopropylmethoxy)-benzamide;
3,4,5-Trifluoro-2-(2-fluoro-4-iodo-phenylamino)-N-(1-hydroxymethyl-cyclopropylmethoxy)-benzamide;
5-Bromo-3,4-difluoro-2-(2-fluoro-4-iodo-phenylamino)-N-(1-hydroxymethyl-cyclopropylmethoxy)-benzamide;
4,5-Difluoro-2-(2-fluoro-4-iodo-phenylamino)-N-(1-hydroxymethyl-cyclopropylmethoxy)-benzamide;
2-(2,4-Difluoro-phenylamino)-3,4-difluoro-N-(1-hydroxymethyl-cyclopropylmethoxy)-benzamide;
2-(4-Bromo-2-fluoro-phenylamino)-3,4-difluoro-N-(1-hydroxymethyl-cyclopropylmethoxy)-benzamide;
2-(4-Chloro-2-fluoro-phenylamino)-3,4-difluoro-N-(1-hydroxymethyl-cyclopropylmethoxy)-benzamide;
5-Chloro-2-(2,4-difluoro-phenylamino)-3,4-difluoro-N-(1-hydroxymethyl-cyclopropylmethoxy)-benzamide;
2-(2,4-Difluoro-phenylamino)-3,4-difluoro-N-(2-hydroxy-3-methoxy-propoxy)-benzamide;
5-Chloro-2-(2,4-difluoro-phenylamino)-3,4-difluoro-N-(2-hydroxy-3-methoxy-propoxy)-benzamide;
2-(4-Bromo-2-fluoro-phenylamino)-3,4-difluoro-N-(2-hydroxy-3-methoxy-propoxy)-benzamide;
2-(4-Chloro-2-fluoro-phenylamino)-3,4-difluoro-N-(2-hydroxy-3-methoxy-propoxy)-benzamide;
3,4,5-Trifluoro-2-(4-iodo-2-methyl-phenylamino)-N-(2-phenylamino-ethoxy)-benzamide;
5-Bromo-3,4-difluoro-2-(4-iodo-2-methyl-phenylamino)-N-(2-phenylamino-ethoxy)-benzamide;
2-(2-Chloro-4-iodo-phenylamino)-3,4-difluoro-N-(2-phenylamino-ethoxy)-benzamide;
2-(2-Chloro-4-iodo-phenylamino)-3,4,5-trifluoro-N-(2-phenylamino-ethoxy)-benzamide;
3,4-Difluoro-2-(4-iodo-2-methyl-phenylamino)-N-(2-phenylamino-ethoxy)-benzamide;
5-Bromo-2-(2-chloro-4-iodo-phenylamino)-3,4-difluoro-N-(2-phenylamino-ethoxy)-benzamide;
3,4-Difluoro-2-(2-fluoro-4-iodo-phenylamino)-N-((S)-3-hydroxy-2-methylamino-propoxy)-benzamide;
3,4-Difluoro-2-(2-fluoro-4-iodo-phenylamino)-N-((R)-3-hydroxy-2-methylamino-propoxy)-benzamide;
(S)-5-Chloro-3,4-Difluoro-2-(2-fluoro-4-iodo-phenylamino)-N-(3-hydroxy-2-methylamino-propoxy)-benzamide;
(R)-5-Chloro-3,4-Difluoro-2-(2-fluoro-4-iodo-phenylamino)-N-(3-hydroxy-2-methylamino-propoxy)-benzamide;
(S)-5-Chloro-2-(2-chloro-4-iodo-phenylamino)-3,4-difluoro-N-(3-hydroxy-2-methylamino-propoxy)-benzamide;
(R)-5-Chloro-2-(2-chloro-4-iodo-phenylamino)-3,4-difluoro-N-(3-hydroxy-2-methylamino-propoxy)-benzamide; and
3,4-Difluoro-2-(2-fluoro-4-iodo-phenylamino)-N-(2-hydroxy-3-methylamino-propoxy)-benzamide.

15. The method according to claim 1, wherein the MEK inhibitor comprises N-[(R)-2,3-Dihydroxy-propoxy]-3,4-difluoro-2-(2-fluoro-4-iodo-phenylamino)-benzamide.

16. The method according to claim 2, wherein the MEK inhibitor comprises N-[(R)-2,3-Dihydroxy-propoxy]-3,4-difluoro-2-(2-fluoro-4-iodo-phenylamino)-benzamide.

17. The method according to claim 2, wherein the neutrophil mediated disease or condition includes ischemia reperfusion injury, chronic obstructive pulmonary disease, acute respiratory disease syndrome, cystic fibrosis, idiopathic pulmonary fibrosis, sepsis, endotoxemia, emphysema, and asbestosis.

* * * * *